(12) United States Patent
Jang et al.

(10) Patent No.: US 11,084,806 B2
(45) Date of Patent: Aug. 10, 2021

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE, AND DISPLAY DEVICE

(71) Applicant: SAMSUNG SDI CO., LTD., Yongin-si (KR)

(72) Inventors: Kipo Jang, Suwon-si (KR); Youngkwon Kim, Suwon-si (KR); Jinhyun Lui, Suwon-si (KR); Eun Sun Yu, Suwon-si (KR); Sung-Hyun Jung, Suwon-si (KR); Ho Kuk Jung, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 294 days.

(21) Appl. No.: 16/097,657

(22) PCT Filed: May 10, 2017

(86) PCT No.: PCT/KR2017/004834
§ 371 (c)(1),
(2) Date: Oct. 30, 2018

(87) PCT Pub. No.: WO2018/012718
PCT Pub. Date: Jan. 18, 2018

(65) Prior Publication Data
US 2020/0317654 A1    Oct. 8, 2020

(30) Foreign Application Priority Data

Jul. 12, 2016    (KR) .................... 10-2016-0088232

(51) Int. Cl.
*C07D 409/14* (2006.01)
*C07D 407/14* (2006.01)
(Continued)

(52) U.S. Cl.
CPC ......... *C07D 409/14* (2013.01); *C07D 407/14* (2013.01); *H01L 51/0067* (2013.01);
(Continued)

(58) Field of Classification Search
CPC . C07D 409/14; C07D 407/14; H01L 51/0073; H01L 51/0074; H01L 51/0067
See application file for complete search history.

(56) References Cited

U.S. PATENT DOCUMENTS 6,229,012 B1    5/2001  Hu et al.
9,209,406 B2   12/2015  Mizutani et al.
(Continued)

FOREIGN PATENT DOCUMENTS

CN    102850329 A    1/2013
CN    103380508 A    10/2013
(Continued)

OTHER PUBLICATIONS

U.S. Appl. No. 16/321,228, filed Jan. 28, 2019.
(Continued)

*Primary Examiner* — Anthony Ho
(74) *Attorney, Agent, or Firm* — Lee IP Law, PC

(57) ABSTRACT

A compound for an organic optoelectronic device represented by Chemical Formula 1, a composition for an organic optoelectronic device, an organic optoelectronic device including the same, and a display device are disclosed. Details of Chemical Formula 1 are the same as described in the detailed description.

14 Claims, 1 Drawing Sheet

(51) Int. Cl.
*H01L 51/00* (2006.01)
*H01L 51/42* (2006.01)
*H01L 51/50* (2006.01)

(52) U.S. Cl.
CPC ...... *H01L 51/0073* (2013.01); *H01L 51/0074* (2013.01); *H01L 51/4273* (2013.01); *H01L 51/5056* (2013.01); *H01L 51/5072* (2013.01); *H01L 51/5092* (2013.01)

(56) References Cited

U.S. PATENT DOCUMENTS

| | | | |
|---|---|---|---|
| 9,893,290 | B2 | 2/2018 | Min |
| 2004/0164292 | A1 | 8/2004 | Tung |
| 2006/0046342 | A1 | 3/2006 | Karg et al. |
| 2007/0141387 | A1 | 6/2007 | Nakano et al. |
| 2013/0264560 | A1 | 10/2013 | Dobbs et al. |
| 2014/0001456 | A1 | 1/2014 | Mizutani et al. |
| 2014/0361258 | A1 | 12/2014 | Hwang et al. |
| 2015/0028320 | A1 | 1/2015 | Kinoshita et al. |
| 2015/0171336 | A1 | 6/2015 | Park et al. |
| 2015/0171340 | A1 | 6/2015 | Lee |
| 2015/0207082 | A1 | 7/2015 | Dyatkin |
| 2015/0349268 | A1 | 12/2015 | Zeng et al. |
| 2016/0028021 | A1 | 1/2016 | Zeng |
| 2016/0329502 | A1 | 11/2016 | Dyatkin et al. |
| 2017/0025618 | A1 | 1/2017 | Zheng et al. |
| 2017/0117488 | A1 | 4/2017 | Ahn |
| 2018/0033975 | A1 | 2/2018 | Kim |

FOREIGN PATENT DOCUMENTS

| | | | |
|---|---|---|---|
| CN | 104271703 | A | 1/2015 |
| CN | 103232843 | B | 2/2015 |
| CN | 104812750 | A | 7/2015 |
| CN | 104885247 | A | 9/2015 |
| CN | 104995187 | A | 10/2015 |
| CN | 105153130 | A | 12/2015 |
| CN | 105315219 | A | 2/2016 |
| CN | 105315265 | A | 2/2016 |
| CN | 105359290 | A | 2/2016 |
| CN | 105473684 | A | 4/2016 |
| CN | 107093677 | A | 8/2017 |
| CN | 107325090 | A | 11/2017 |
| CN | 108290854 | A | 7/2018 |
| EP | 2 966 706 | A2 | 1/2016 |
| EP | 3 268 449 | A1 | 2/2016 |
| JP | 2014/040423 | A | 3/2014 |
| JP | 2014-123687 | A | 7/2014 |
| JP | 5541167 | B2 | 7/2014 |
| JP | 2014-157947 | A | 8/2014 |
| JP | 5847420 | B2 | 1/2016 |
| JP | 2016/019002 | A | 2/2016 |
| JP | 2016-506414 | A | 3/2016 |
| JP | 2016-525081 | A | 8/2016 |
| JP | 2018-514081 | A | 5/2018 |
| KR | 10-2011-0096453 | | 8/2011 |
| KR | 10-2010-0118690 | | 11/2011 |
| KR | 10-2012-0129733 | A | 11/2012 |
| KR | 10-2013-0036048 | A | 4/2013 |
| KR | 10-2013-0061371 | | 6/2013 |
| KR | 10-2014-0005804 | A | 1/2014 |
| KR | 10-2014-0010133 | | 1/2014 |
| KR | 10-1423067 | B1 | 7/2014 |
| KR | 10-2014-0144550 | A | 12/2014 |
| KR | 10-2015-0036736 | | 4/2015 |
| KR | 10-2015-0042335 | A | 4/2015 |
| KR | 10-2015-0070860 | A | 6/2015 |
| KR | 10-1542714 | B1 | 7/2015 |
| KR | 10-2015-0116776 | A | 10/2015 |
| KR | 10-2015-0129282 | A | 11/2015 |
| KR | 10-2015-0131998 | A | 11/2015 |
| KR | 10-2015-0136942 | | 12/2015 |
| KR | 10-2016-0006633 | A | 1/2016 |
| KR | 10-1593465 | B1 | 2/2016 |
| KR | 10-2016-0028524 | A | 3/2016 |
| KR | 10-2016-0034528 | A | 3/2016 |
| KR | 2016-37909 | | 3/2016 |
| KR | 10-2016-0038006 | A | 4/2016 |
| KR | 10-2016-0055556 | A | 5/2016 |
| KR | 10-2016-0080090 | A | 7/2016 |
| KR | 10-2016-0110078 | A | 9/2016 |
| KR | 10-2017-0022865 | | 3/2017 |
| KR | 10-2017-0089599 | A | 8/2017 |
| KR | 10-2017-0116992 | A | 10/2017 |
| KR | 10-2017-0141144 | A | 12/2017 |
| TW | 201609712 | A | 3/2016 |
| TW | 201619152 | A | 6/2016 |
| WO | WO 2010/044342 | A1 | 4/2010 |
| WO | WO 2013/077352 | A1 | 5/2013 |
| WO | WO 2014/054912 | A1 | 4/2014 |
| WO | WO 2014208755 | A1 | 12/2014 |
| WO | WO 2015/000549 | A1 | 1/2015 |
| WO | WO 2015/156587 | A1 | 10/2015 |
| WO | WO 2015/160224 | A1 | 10/2015 |
| WO | WO 2016/076384 | A1 | 5/2016 |
| WO | WO 2016084962 | A1 | 6/2016 |
| WO | WO 2016 148390 | A1 | 9/2016 |
| WO | WO 2016/172414 | A1 | 10/2016 |
| WO | WO 2017/016630 | A1 | 2/2017 |
| WO | WO 2017/146466 | A1 | 8/2017 |
| WO | WO 2017/171420 | A1 | 10/2017 |
| WO | WO 2018/016742 | A1 | 1/2018 |
| WO | WO 2018/021663 | A1 | 2/2018 |
| WO | WO 2018/062659 | A1 | 4/2018 |
| WO | WO 2018/093026 | A1 | 5/2018 |
| WO | WO 2018/097461 | A1 | 5/2018 |
| WO | WO 2018/128255 | A1 | 7/2018 |

OTHER PUBLICATIONS

Extended European Search Report dated Feb. 17, 2020, corresponding European Patent Application No. 17827792.7.
Extended European Search Report dated Feb. 28, 2020, European Patent Application No. 17834608.6.
International Search Report dated Apr. 24, 2017.
U.S. Appl. No. 16/468,779, filed Jun. 12, 2019.
U.S. Appl. No. 16/099,507, filed Nov. 7, 2018.
U.S. Appl. No. 16/099,523, filed Nov. 7, 2018.
European Search Report dated Dec. 19, 2019, Application No. 17820373.3.
European Search Report dated Jan. 8, 2020, Application No. 17820372.5.
U.S. Office Action dated Jan. 13, 2021 from Co-pending U.S. Appl. No. 16/468,779.
Japanese Office action dated Sep. 29, 2020, received in Japanese Application No. 2018-568699.
Japanese Notice of Allowance dated Oct. 6, 2020, received in Japanese Application No. 2019-503551.
Yu, Organic Electronics, 38, 2016, 301-306.
U.S. Office action received in co pending application U.S. Appl. No. 16/099,507, dated Apr. 16, 2021.
U.S. Office action received in co pending application U.S. Appl. No. 16/099,523, dated Apr. 19, 2021.
European Office action dated Mar. 25, 2021.
US. Office Action received in Co Pending U.S. Appl. No. 16/321,228 dated Jun. 25, 2021.

【Figure 1】
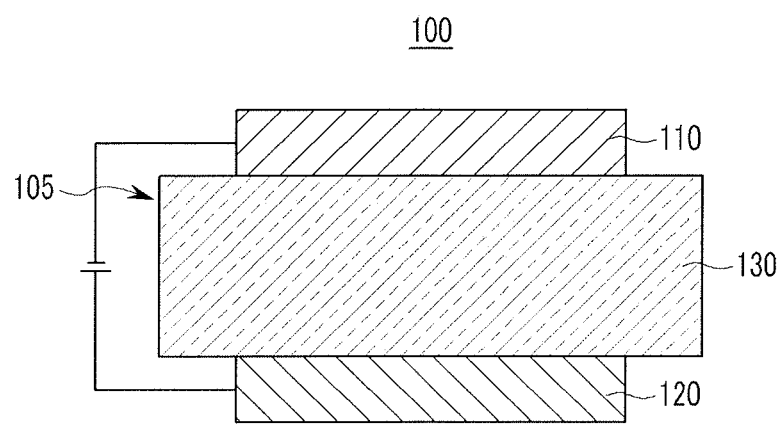
【Figure 2】
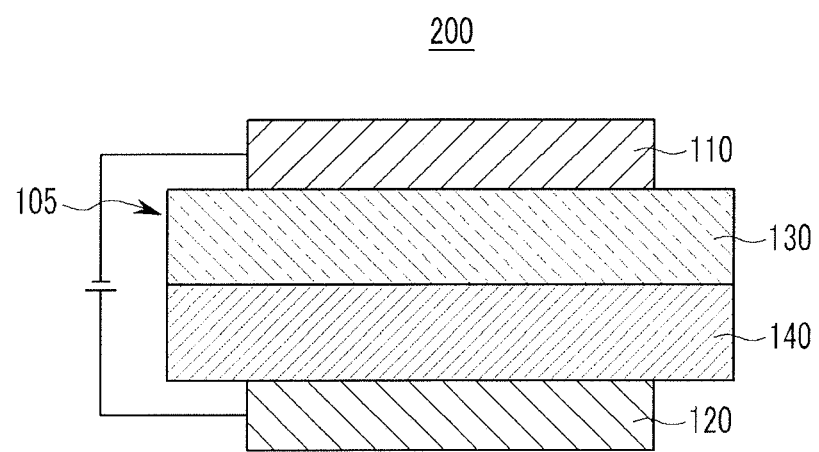

COMPOUND FOR ORGANIC OPTOELECTRONIC DEVICE, COMPOSITION FOR ORGANIC OPTOELECTRONIC DEVICE, ORGANIC OPTOELECTRONIC DEVICE, AND DISPLAY DEVICE

CROSS-REFERENCE TO THE RELATED APPLICATION

This is the U.S. national phase application based on PCT Application No. PCT/KR2017/004834, filed May 10, 2017, which is based on Korean Patent Application No. 10-2016-0088232, filed Jul. 12, 2016, the entire contents of all of which are hereby incorporated by reference.

TECHNICAL FIELD

A compound for an organic optoelectronic device, a composition for an organic optoelectronic device, an organic optoelectronic device, and a display device are disclosed.

BACKGROUND ART

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectronic device capable of realizing an organic optoelectronic device having high efficiency and a long life-span.

Another embodiment provides a composition for an organic optoelectronic device including the compound for an organic optoelectronic device.

Yet another embodiment provides an organic optoelectronic device including the compound.

Still another embodiment provides a display device including the organic optoelectronic device.

Technical Solution

According to an embodiment, a compound for an organic optoelectronic device represented by Chemical Formula 1 is provided.

[Chemical Formula 1]

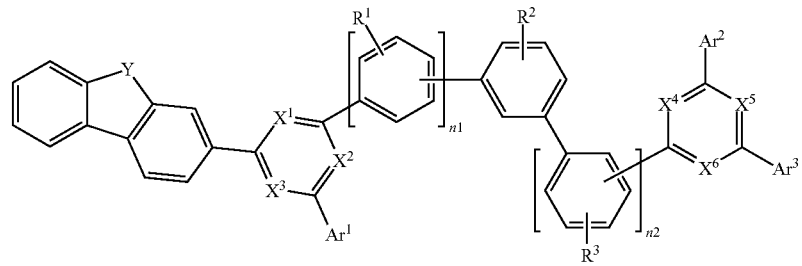

In Chemical Formula 1, $X^1$ to $X^6$ are independently N or $CR^a$, at least two of $X^1$ to $X^3$ are N, at least two of $X^4$ to $X^6$ are N, Y is O or S, $Ar^1$ to $Ar^3$ are independently a substituted or unsubstituted C6 to C30 aryl group, $R^a$ and $R^1$ to $R^3$ are independently hydrogen, deuterium, a substituted or unsubstituted C1 to C10 alkyl group, a substituted or unsubstituted C6 to C30 aryl group, or a combination thereof, n1 and n2 are independently one of integers of 0 to 2, and the "substituted" refers to replacement of at least one hydrogen by deuterium, a C1 to C20 alkyl group, a C6 to C30 aryl group, or a C2 to C30 heteroaryl group.

According to another embodiment, a composition for an organic optoelectronic device includes the first compound for an organic optoelectronic device; and a second compound for an organic optoelectronic device represented by Chemical Formula 2.

[Chemical Formula 2]

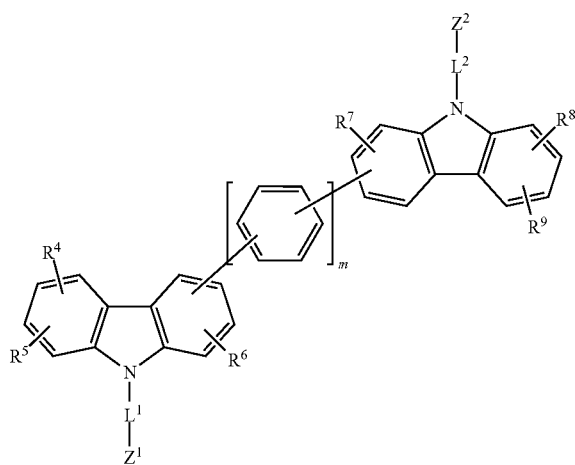

In Chemical Formula 2, $L^1$ and $L^2$ are independently a single bond, a substituted or unsubstituted C6 to C30 arylene group, a substituted or unsubstituted C2 to C30 heteroarylene group, or a combination thereof, $Z^1$ and $Z^2$ are independently a substituted or unsubstituted C6 to C30 aryl group, a substituted or unsubstituted C2 to C30 heterocyclic group, or a combination thereof, $R^4$ to $R^9$ are independently hydrogen, deuterium, a substituted or unsubstituted C1 to C20 alkyl group, a substituted or unsubstituted C6 to O30 aryl group, a substituted or unsubstituted C2 to C30 heterocyclic group, or a combination thereof, m is one of integers of 0 to 2; and the "substituted" refers to replacement of at least one hydrogen by deuterium, a C1 to C4 alkyl group, a C6 to C18 aryl group, or a C2 to C30 heteroaryl group.

According to another embodiment, an organic optoelectronic device includes an anode and a cathode facing each other and at least one organic layer disposed between the anode and the cathode, wherein the organic layer includes the compound for an organic optoelectronic device, or the composition for an organic optoelectronic device.

According to yet another embodiment, a display device includes the organic optoelectronic device.

Advantageous Effects

An organic optoelectronic device having high efficiency and a long life-span may be realized.

DESCRIPTION OF THE DRAWINGS

FIGS. 1 and 2 are cross-sectional views showing organic light emitting diodes according embodiments.

DESCRIPTION OF SYMBOLS

100, 200: organic light emitting diode
105: organic layer
110: cathode
120: anode
130: light emitting layer
140: hole auxiliary layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to 010 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to 010 trifluoroalkyl group, a cyano group, or a combination thereof.

In examples of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, the "substituted" refers to replacement of at least one hydrogen of a substituent or a compound by deuterium, a C1 to C20 alkyl group, a C6 to C30 aryl group, or a C2 to C30 heteroaryl group. In addition, in specific examples of the present invention, the "substituted" refers to replacement of at least one hydrogen of a substituent or a compound by deuterium, a C1 to C5 alkyl group, a C6 to C18 aryl group, a pyridinyl group, a quinolinyl group, an isoquinolinyl group, a dibenzofuranyl group, a dibenzothiophenyl group, or a carbazolyl group. In addition, in specific examples of the present invention, the "substituted" refers to replacement of at least one hydrogen of a substituent or a compound by deuterium, a C1 to C5 alkyl group, a C6 to C18 aryl group, a dibenzofuranyl group, or a dibenzothiophenyl group. In addition, in specific examples of the present invention, the "substituted" refers to replacement of at least one hydrogen of a substituent or a compound by deuterium, a methyl group, an ethyl group, a propanyl group, a butyl group, a phenyl group, a biphenyl group, a terphenyl group, a naphthyl group, a triphenyl group, a dibenzofuranyl group, or a dibenzothiophenyl group.

In the present specification when a definition is not otherwise provided, "hetero" refers to one including one to three heteroatoms selected from N, O, S, P, and Si, and remaining carbons in one functional group.

In the present specification, when a definition is not otherwise provided, "an alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "an aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment is represented by Chemical Formula 1.

[Chemical Formula 1]

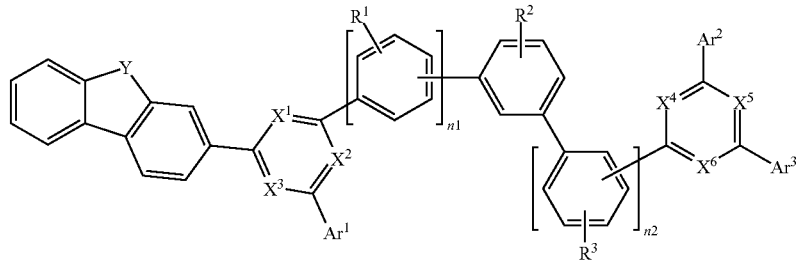

In Chemical Formula 1, $X^1$ to $X^6$ are independently N or $CR^a$, at least two of $X^1$ to $X^3$ are N, at least two of $X^4$ to $X^6$ are N, Y is O or S, $Ar^1$ to $Ar^3$ are independently a substituted or unsubstituted C6 to C30 aryl group, $R^a$ and $R^1$ to $R^3$ are independently hydrogen, deuterium, a substituted or unsubstituted C1 to C10 alkyl group, a substituted or unsubstituted C6 to C30 aryl group, or a combination thereof, n1 and n2 are independently one of integers of 0 to 2, and the "substituted" refers to replacement of at least one hydrogen by deuterium, a C1 to C20 alkyl group, a C6 to C30 aryl group, or a C2 to C30 heteroaryl group. In a specific example of the present invention, the "substituted" refers to replacement of at least one hydrogen by deuterium, a C1 to C20 alkyl group, a C6 to C30 aryl group, a pyridinyl group, a quinolinyl group, an isoquinolinyl group, a dibenzofuranyl group, or a dibenzothiophenyl group.

In one example of the present invention, the "substituted" refers to replacement of at least one hydrogen by deuterium, a phenyl group, a biphenyl group, or a naphthyl group.

A compound for an organic optoelectronic device according to the present invention includes an ET core including an N-containing 6-membered ring that includes a substituent directly linked with dibenzofuran or dibenzothiophene at a position No. 3 without a linking group, and thereby a LUMO energy band is effectively expanded, planarity of a molecular structure is increased, and the compound may become a structure capable of accepting electrons when an electric field is applied, and accordingly an organic optoelectronic device including the compound for an organic optoelectronic device may exhibit a lowered driving voltage. Such a LUMO expansion and ring fusion increase stability for electrons of the ET core and life-span of a device is effectively improved.

In addition, interactions with adjacent molecules may be suppressed and crystallization is decreased due to steric hindrance characteristics by at least one meta-bound arylene and accordingly efficiency and life-span characteristics of an organic optoelectronic device including the compound for an organic optoelectronic device may be improved.

A kinked moiety such as the meta-bound arylene increases a glass transition temperature (Tg) of a compound and stability of a compound may be increased and degradation may be suppressed when it is applied to a device.

The glass transition temperature (Tg) may have a relation with thermal stability of a compound and a device including the same. That is, a compound for an organic optoelectronic device having a high glass transition temperature (Tg) is applied to an organic light emitting diode in a thin film form, in subsequent processes after depositing the compound for an organic optoelectronic device, for example in an encapsulation process, degradation by a temperature may be prevented and thus life-span characteristics of an organic compound and a device may be ensured.

Particularly, a driving voltage may be further lowered by an ET-dimer including an additional ET group (triazine or pyrimidine) including a linker in one direction of substitutents and such a structure increases electron transport capability and realizes a fast electron transport layer or low-driving host device effectively.

In one example embodiment of the present invention, $Ar^1$ to $Ar^3$ may be independently a substituted or unsubstituted phenyl group, a substituted or unsubstituted biphenyl group, a substituted or unsubstituted terphenyl group, a substituted or unsubstituted naphthyl group, or a substituted or unsubstituted fluorenyl group. Specifically, $Ar^1$ to $Ar^3$ are independently a phenyl group, or a biphenyl group, and more specifically, $Ar^1$ may be a phenyl group and $Ar^2$ and $Ar^3$ are independently a phenyl group or a biphenyl group. For example, $Ar^2$ and $Ar^3$ may be a phenyl group or one of $Ar^2$ and $Ar^3$ may be a phenyl group and the remainder may be a biphenyl group. The biphenyl group may be more specifically an ortho-biphenyl group, a meta-biphenyl group, or a para-biphenyl group.

In an example embodiment of the present invention, the $R^a$ and $R^1$ to $R^3$ may independently be hydrogen, deuterium, a methyl group, an ethyl group, a n-propyl group, an iso-propyl group, a substituted or unsubstituted phenyl group, or a substituted or unsubstituted naphthyl group, specifically the $R^a$ and $R^1$ to $R^3$ may independently be hydrogen, a methyl group, an ethyl group, or a phenyl group, and in the most specific embodiment of the present invention, the $R^a$ may be hydrogen, $R^1$ to $R^3$ may be hydrogen or a phenyl group, and more specifically the $R^a$, $R^1$, and $R^3$ may be hydrogen and $R^2$ may be hydrogen or a phenyl group. For example, the $R^a$ and $R^1$ to $R^3$ may be all hydrogen.

For example, when $R^2$ is the substituent except hydrogen, Chemical Formula 1 may be represented by Chemical Formula 1a including a kinked terphenyl.

[Chemical Formula 1a]

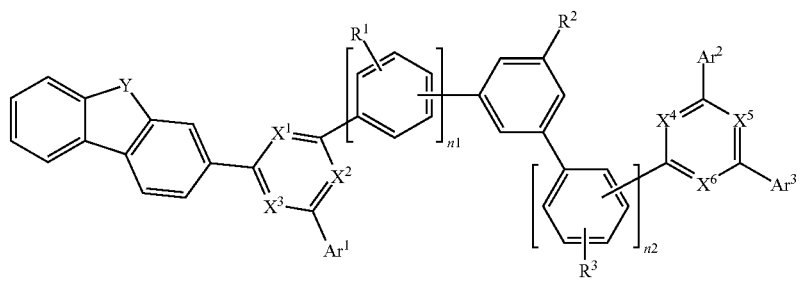

In Chemical Formula 1a, Y, $X^1$ to $X^6$, $R^1$ to $R^3$, $Ar^1$ to $Ar^a$, n1, and n2 are the same as described above.

When the kinked terphenyl structure is included, a glass transition temperature (Tg) may be increased very effectively and a compound having a low molecular weight and a high glass transition temperature (Tg) may be designed and thereby thermal characteristics may be improved and stability may be ensured.

In an example embodiment of the present invention, an ET core formed by the $X^1$ to $X^3$ and an ET group formed by additional $X^4$ to $X^6$ may be pyrimidine or triazine, and Chemical Formula 1 may be for example represented by one of Chemical Formula 1-I, Chemical Formula 1-II, Chemical Formula 1-III, Chemical Formula 1-IV, Chemical Formula 1-V, and Chemical Formula 1-VI, and may specifically be represented by one of Chemical Formula 1-I, Chemical Formula 1-VI, Chemical Formula 1-IV, and Chemical Formula 1-VI. More specifically, Chemical Formula 1 may be represented by Chemical Formula 1-VI.

[Chemical Formula 1-I]
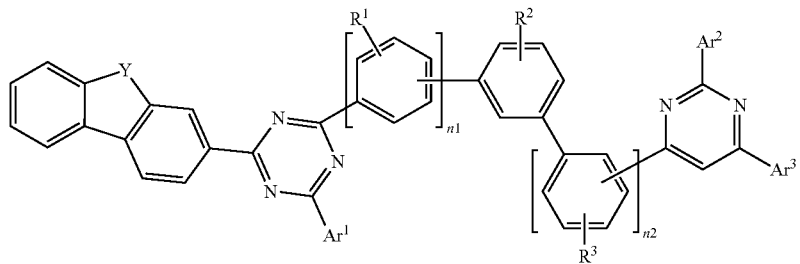
[Chemical Formula 1-II]
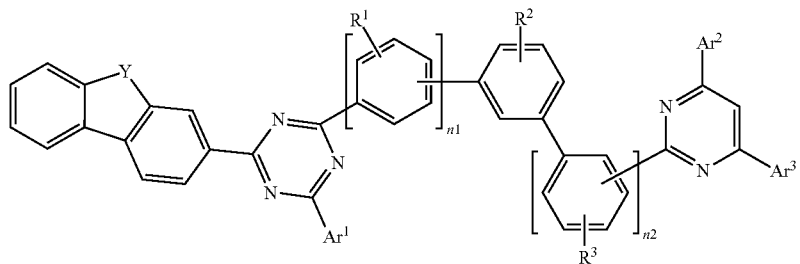
[Chemical Formula 1-III]
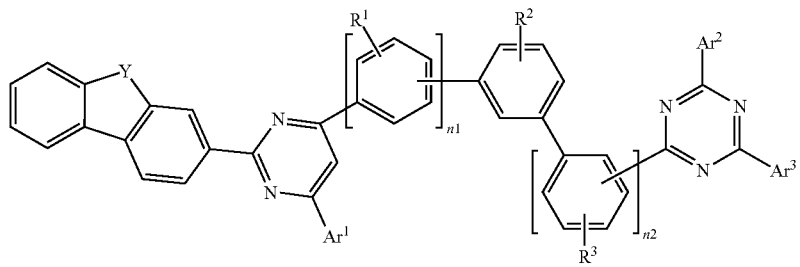
[Chemical Formula 1-IV]
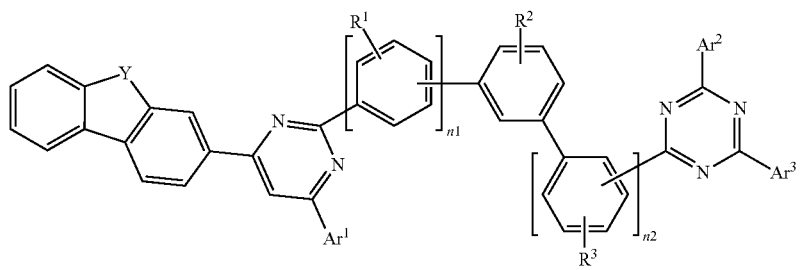
[Chemical Formula 1-V]
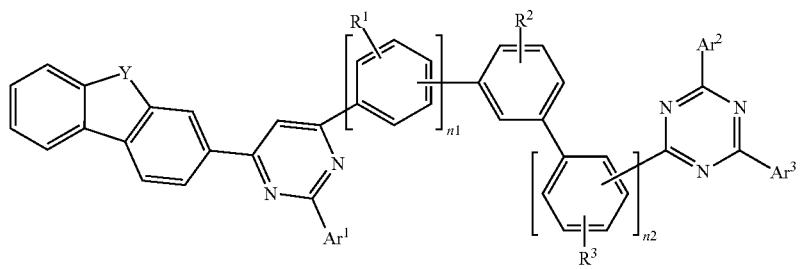
[Chemical Formula 1-VI]
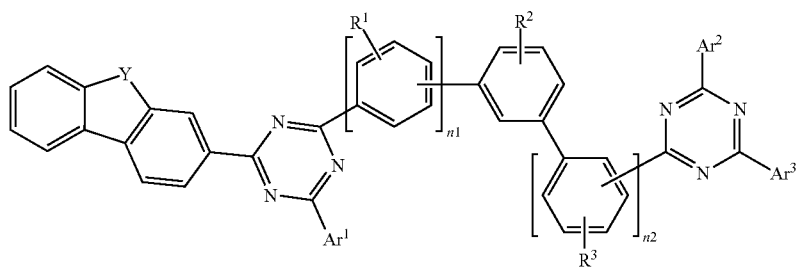

In Chemical Formula 1-I, Chemical Formula 1-II, Chemical Formula 1-III, Chemical Formula 1-IV, Chemical Formula 1-V, and Chemical Formula 1-VI, Y, $Ar^1$ to $Ar^3$, $R^1$ to $R^3$, n1, and n2 are the same as described above.

In an example embodiment of the present invention, n1 may be an integer ranging from 0 to 2 and n2 may be an integer of 0 or 1. When n1 is 2, each $R^1$ may be the same or different. Specifically, n1 may be an integer of 0 or 1.

In another example embodiment of the present invention, n2 may be an integer ranging from 0 to 2 and n1 may be an integer of 0 or 1. When n2 is 2, each $R^3$ may be the same or different. Specifically, n2 may be an integer of 0 or 1.

In the most specific example embodiment of the present invention, the n1 and n2 may independently be an integer of 0 or 1, for example n1 and n2 are 0 or at least one of n1 and n2 may be 1.

Specifically, each of linking groups represented by

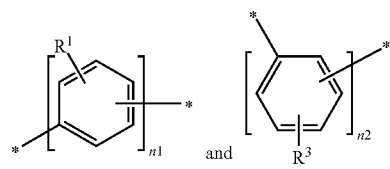

may have a meta bond or a para bond, and Chemical Formulae 1 may be for example represented by one of Chemical Formulae 1-1 to 1-3.

[Chemical Formula 1-1]

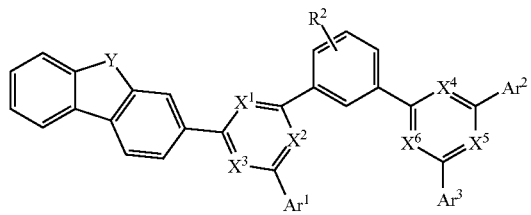

[Chemical Formula 1-2]

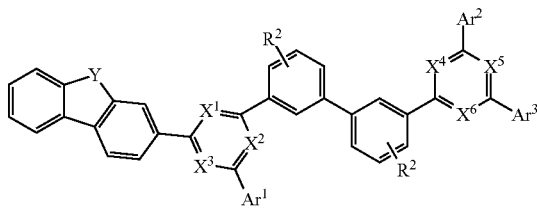

[Chemical Formula 1-3]

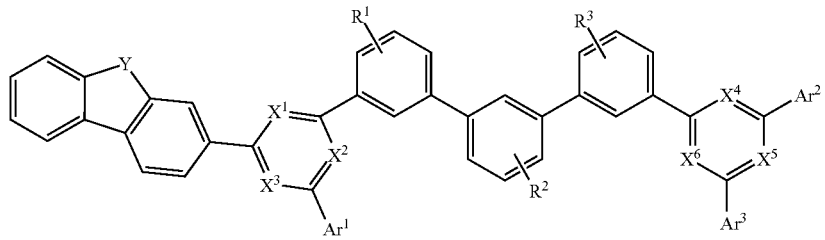

In Chemical Formulae 1-1 to 1-3, Y, $X^1$ to $X^6$, $Ar^1$ to $Ar^a$, and $R^1$ to $R^3$ are the same as described above.

$X^1$ to $X^6$ may independently be N or CH and at least two of $X^1$ to $X^3$ and $X^4$ to $X^6$ may be N.

A specific example embodiment of the present invention may be represented by Chemical Formula 1-1 or Chemical Formula 1-2, and may be for example represented by Chemical Formula 1-1.

The compound for an organic optoelectronic device represented by Chemical Formula 1 may be for example selected from compounds of Group 1, but is not limited thereto.

[Group 1]

[A-1]

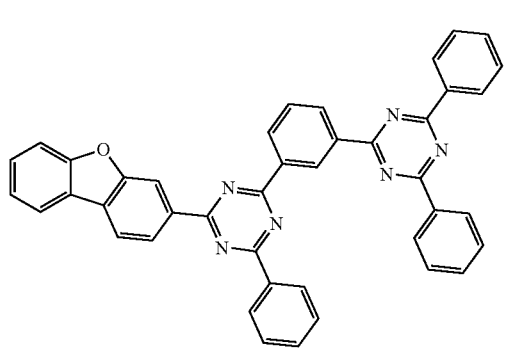

[A-2]

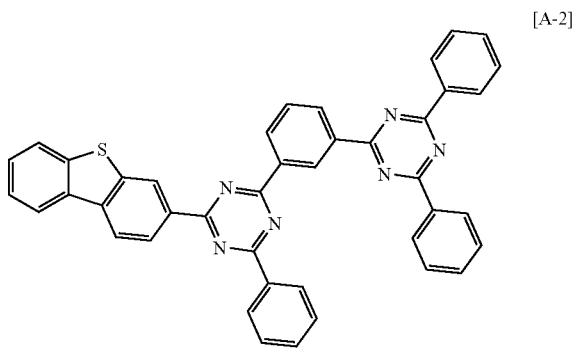

-continued
[A-3]
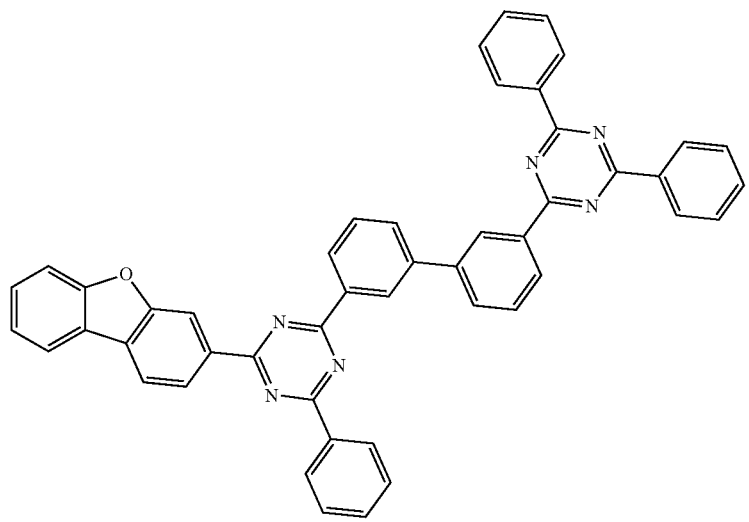
[A-4]
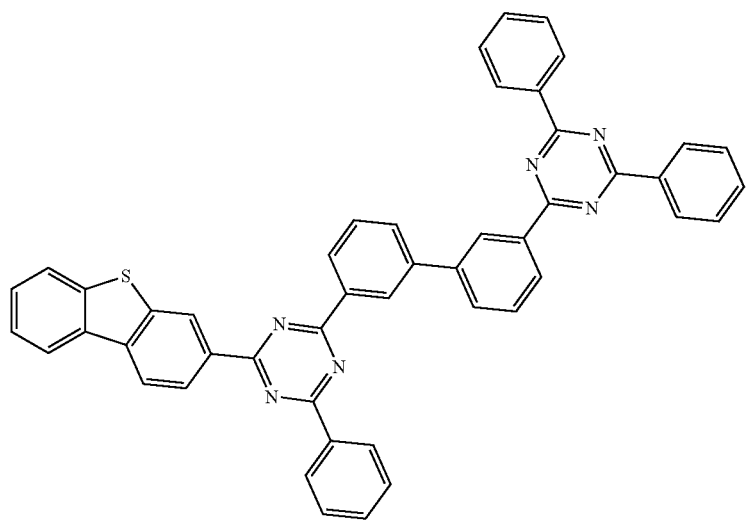
[A-5]
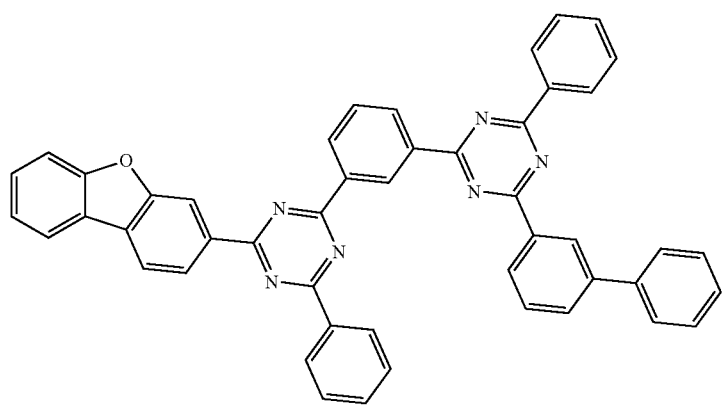

-continued
[A-6]
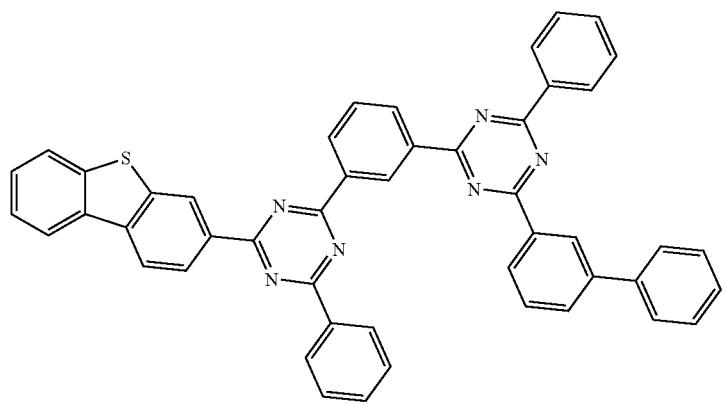
[A-7]
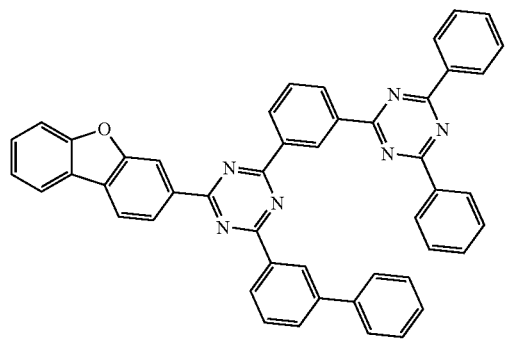
[A-8]
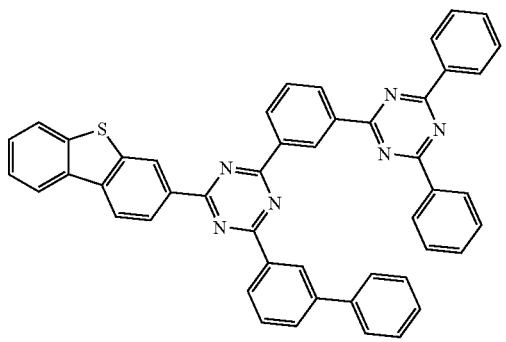
[A-9]
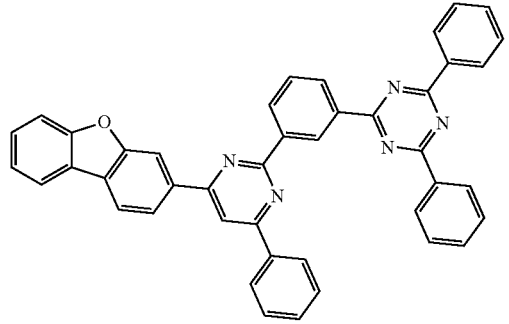
[A-10]
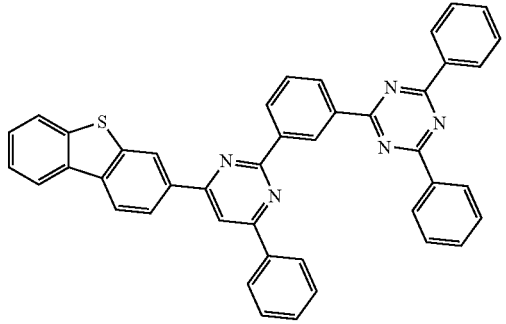
[A-11]
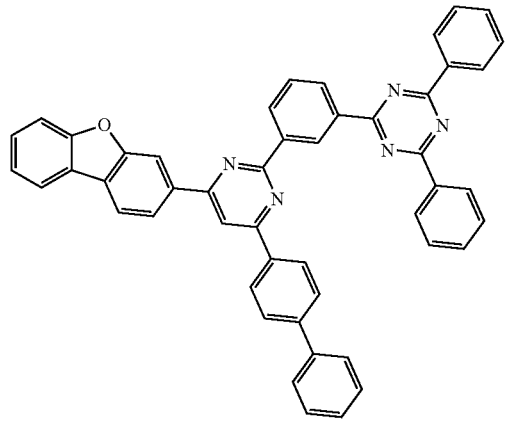
[A-12]
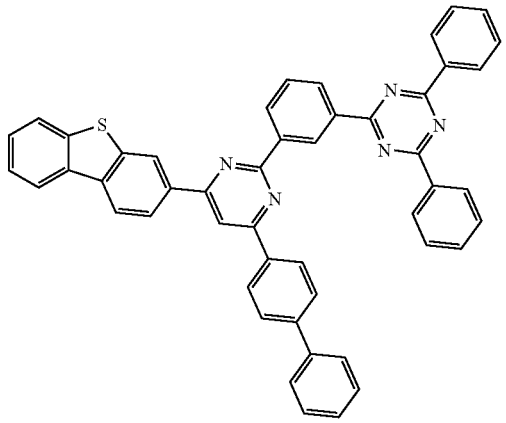

-continued
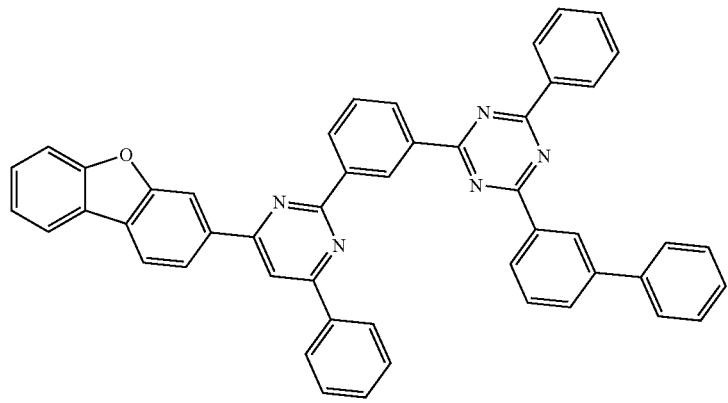
[A-13]
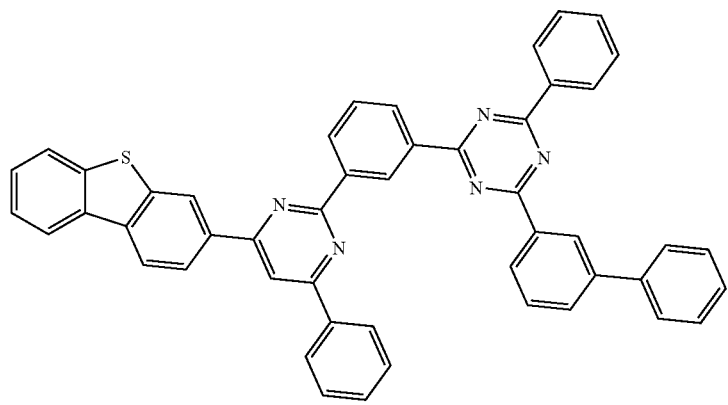
[A-14]
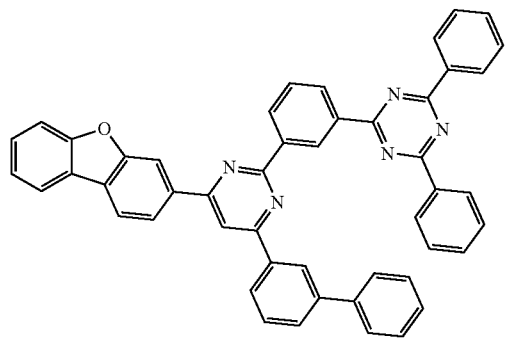
[A-15]
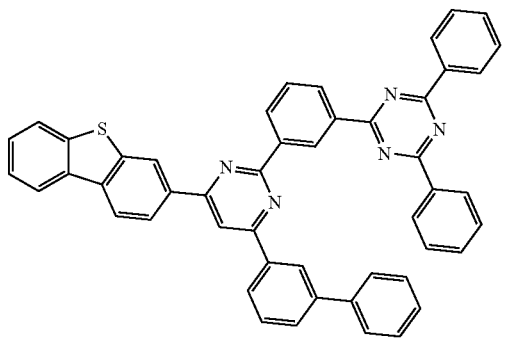
[A-16]
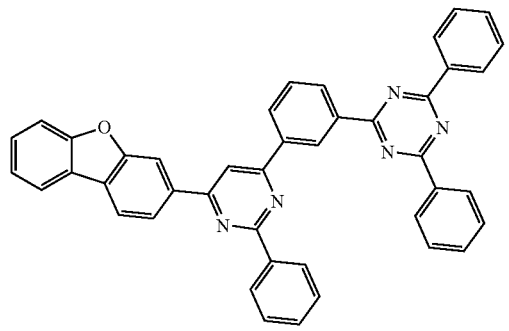
[A-17]
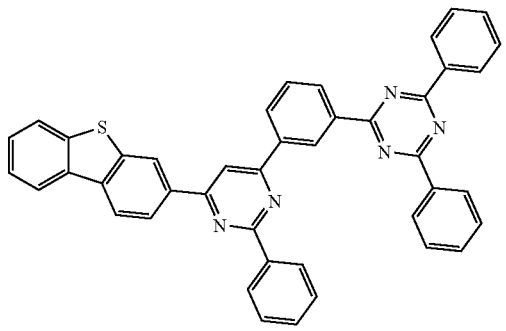
[A-18]

-continued
[A-19]
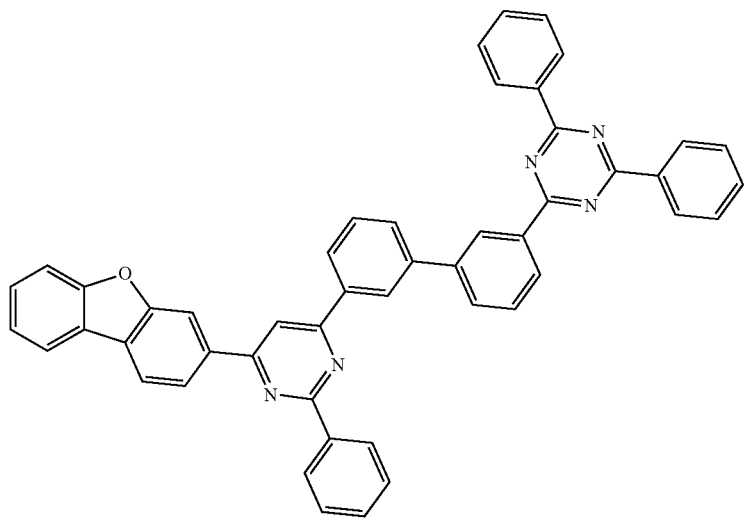
[A-20]
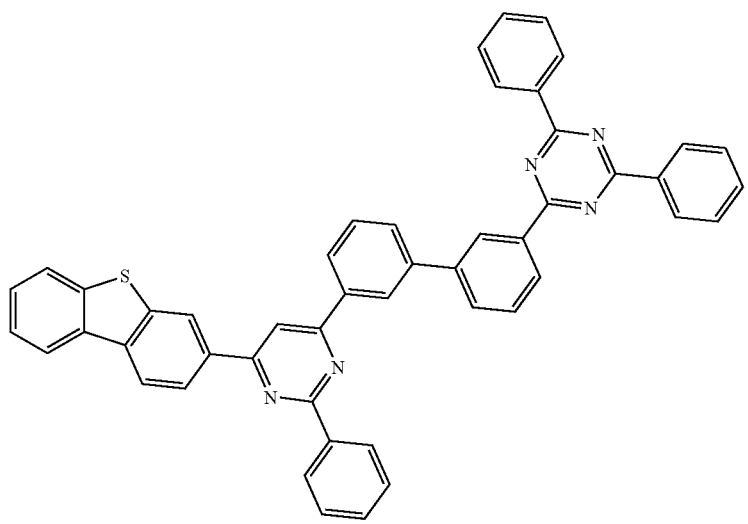
[A-21]
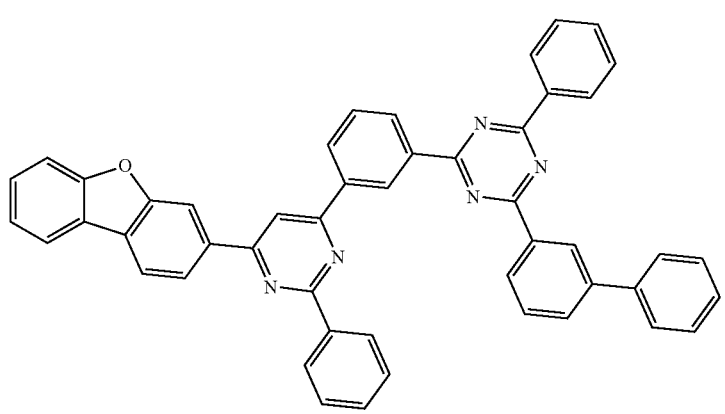

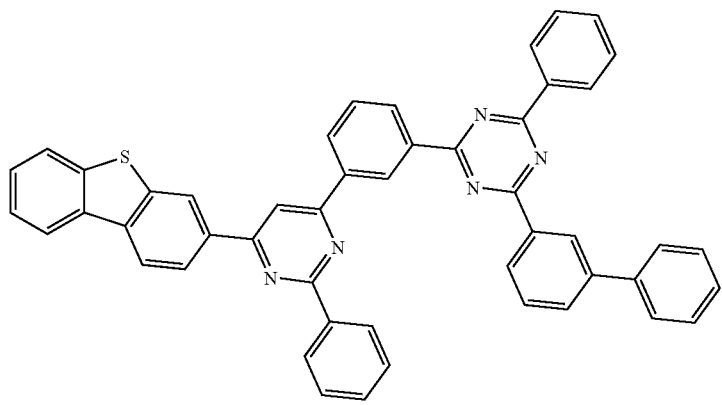
[A-22]
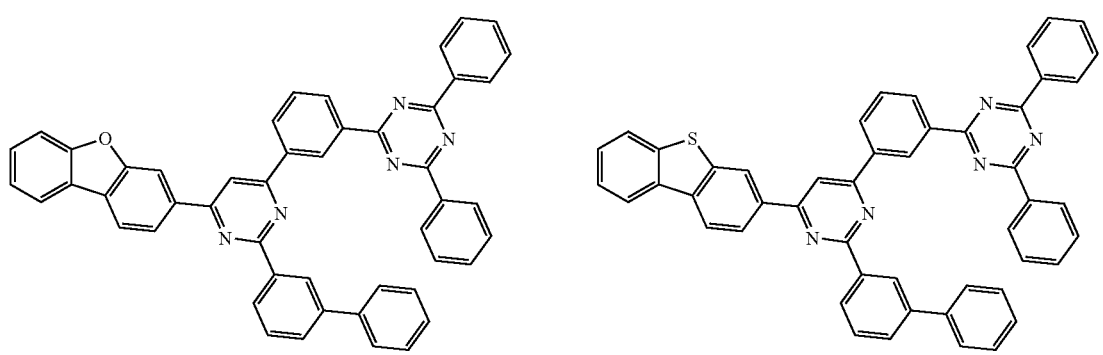
[A-23] [A-24]
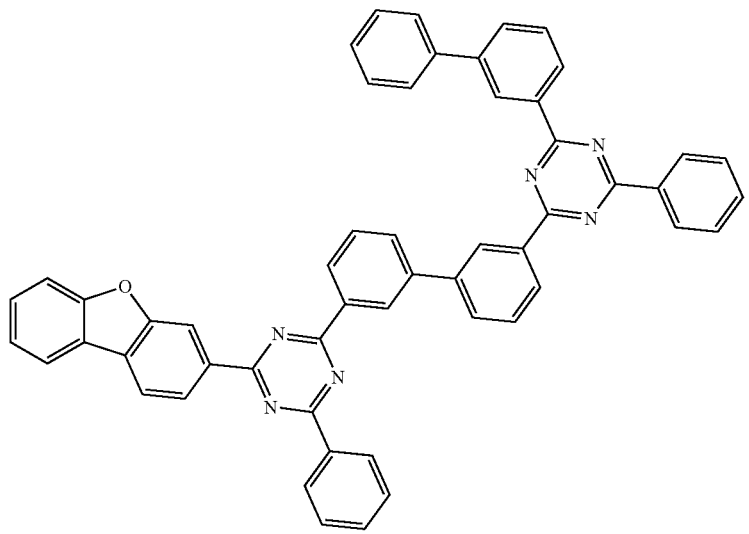
[A-25]

-continued
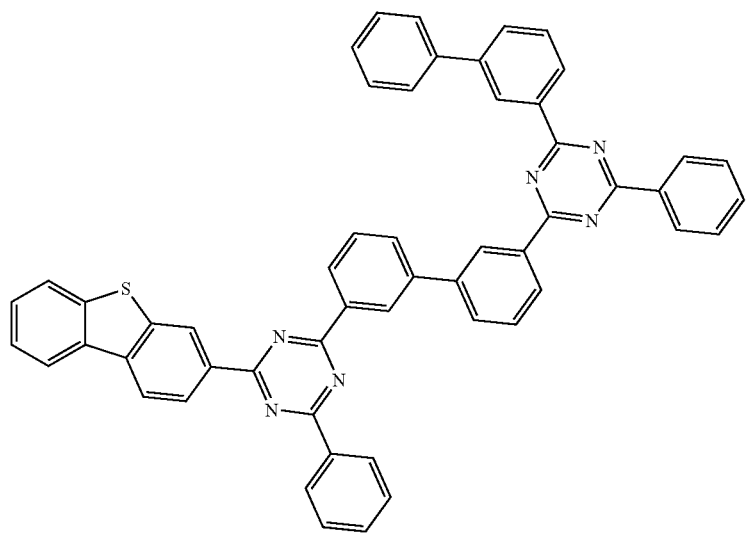
[A-26]
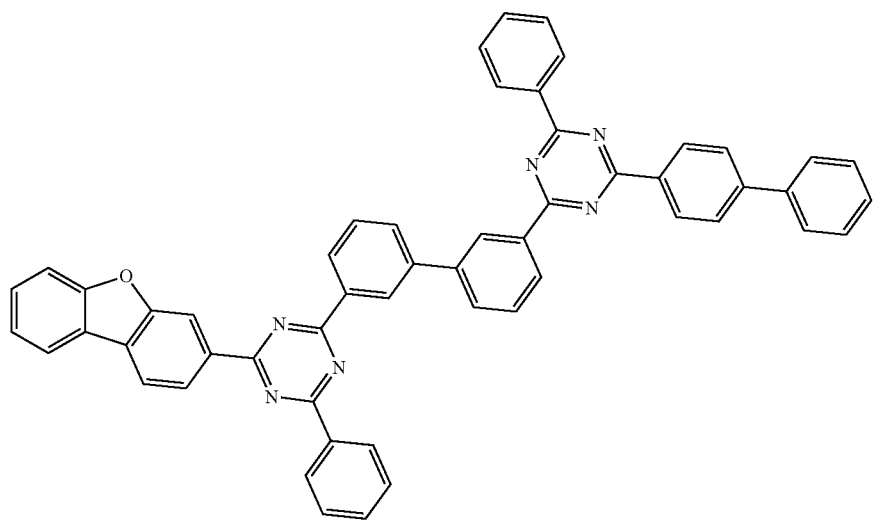
[A-27]
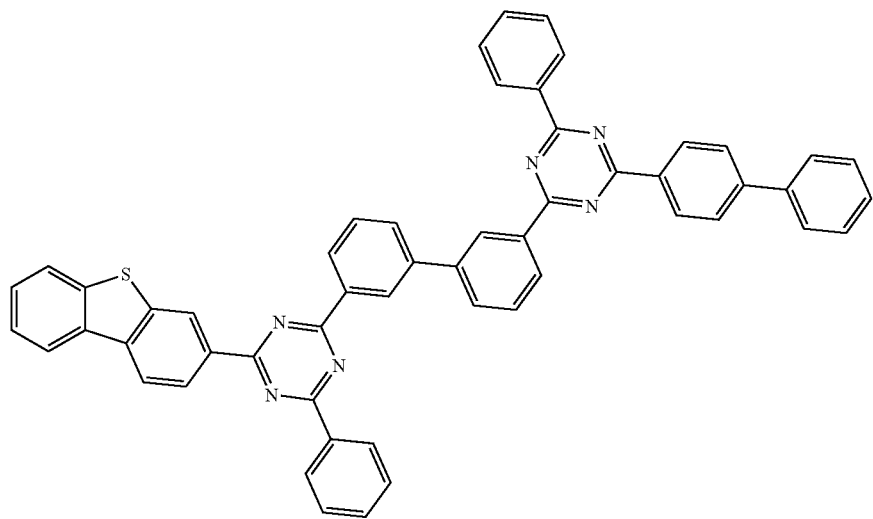
[A-28]

-continued
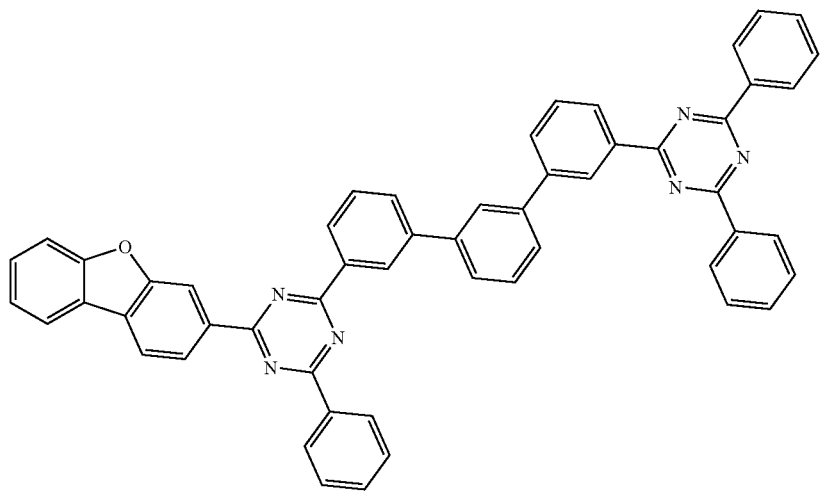
[A-29]
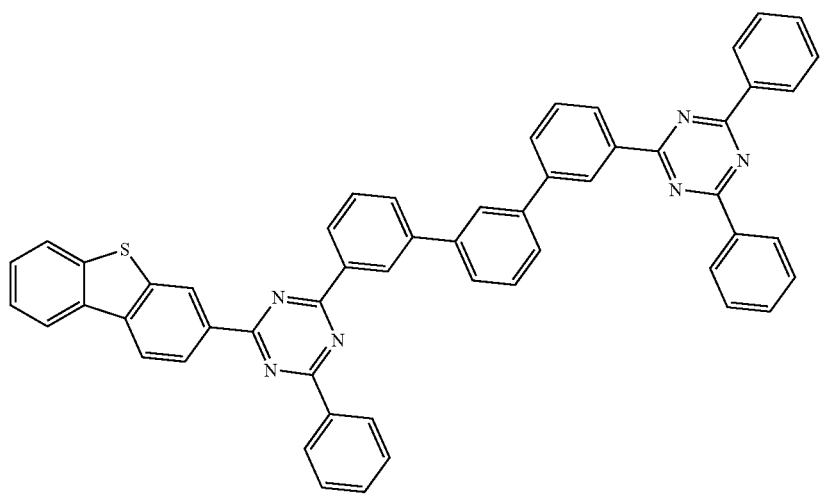
[A-30]
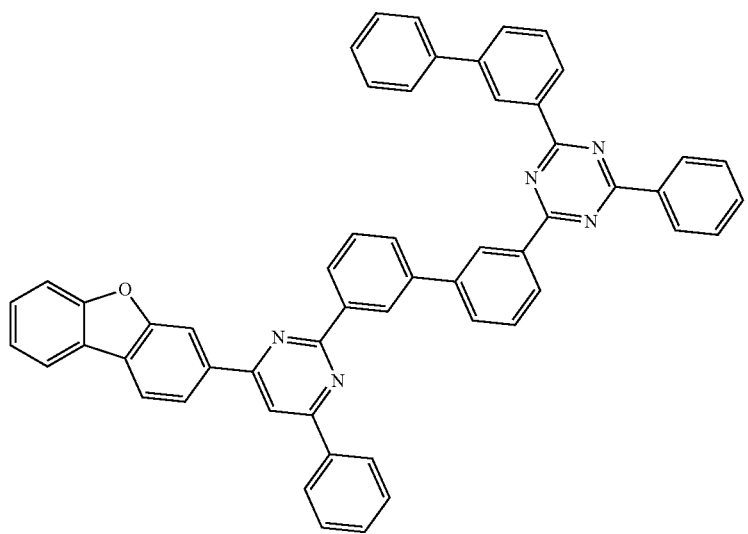
[A-31]

[A-32]
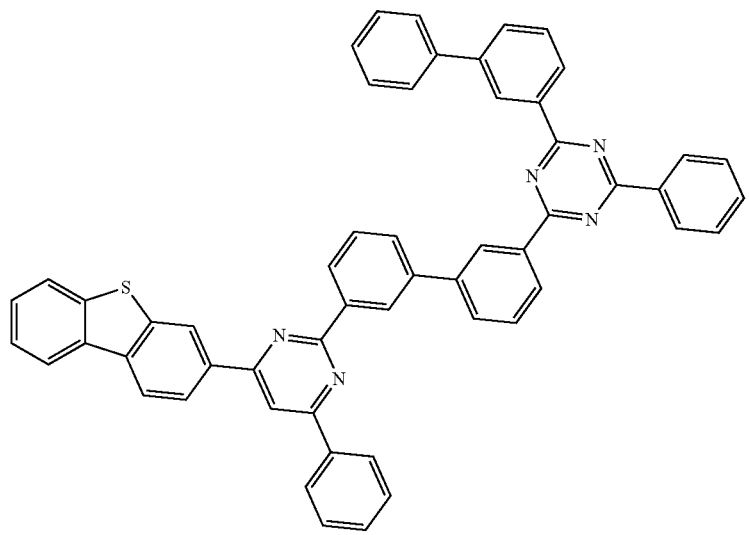
[A-33]
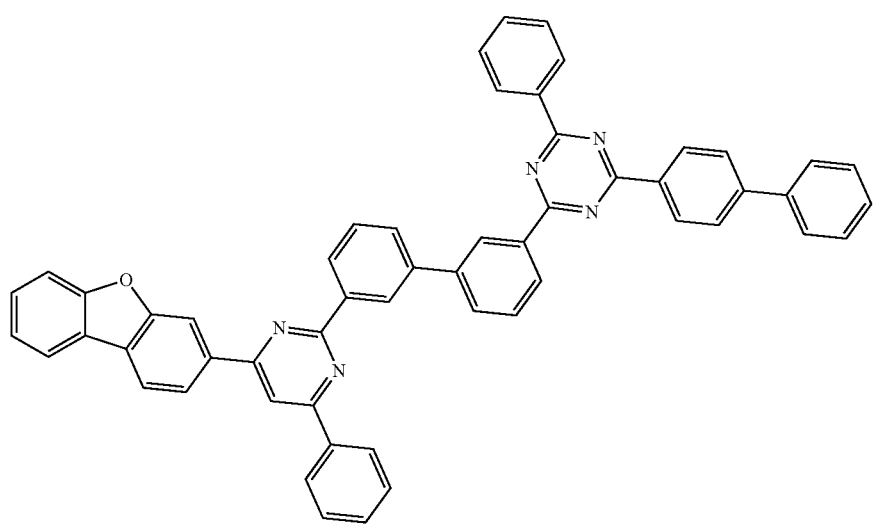
[A-34]
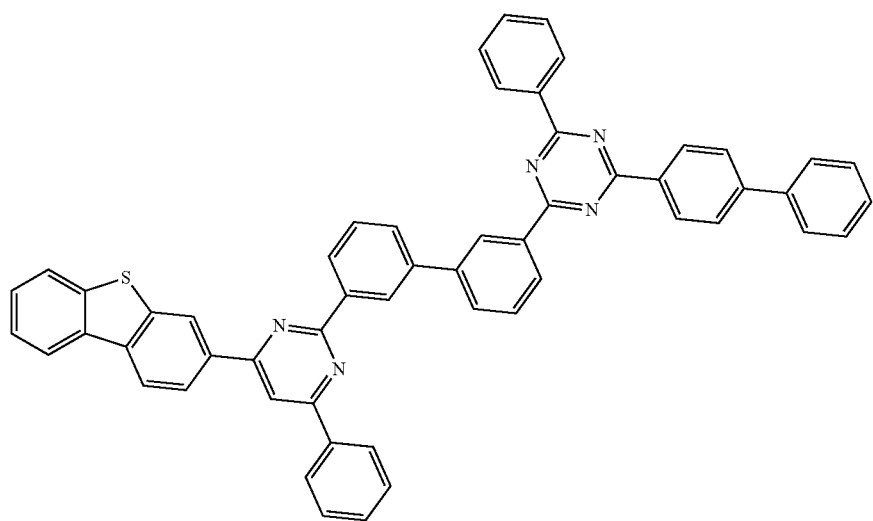

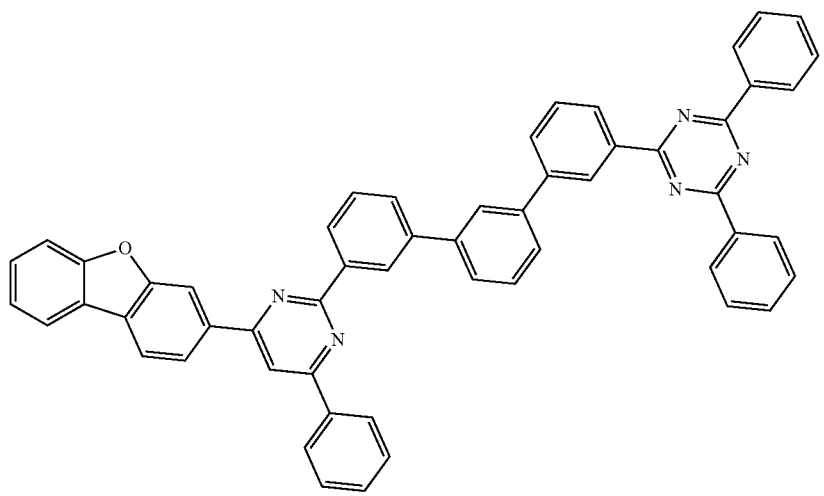
[A-35]
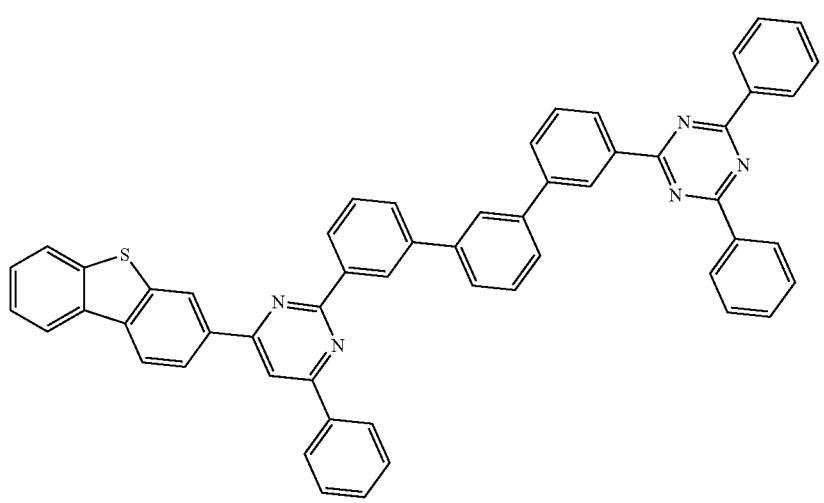
[A-36]
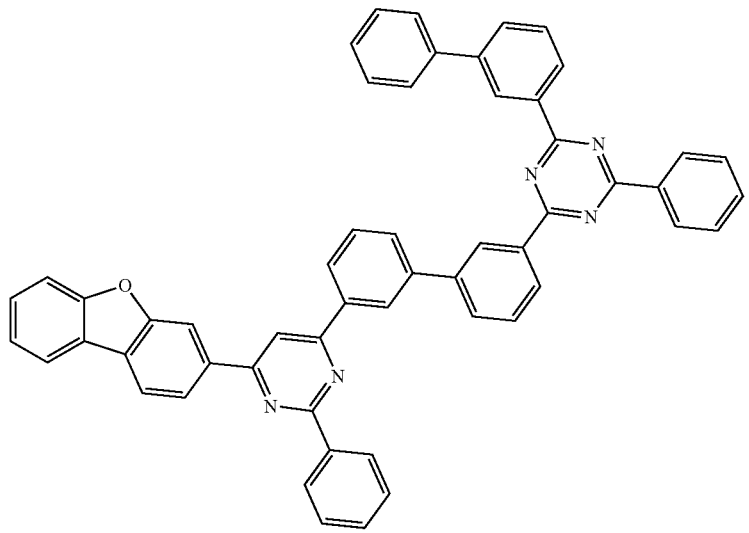
[A-37]

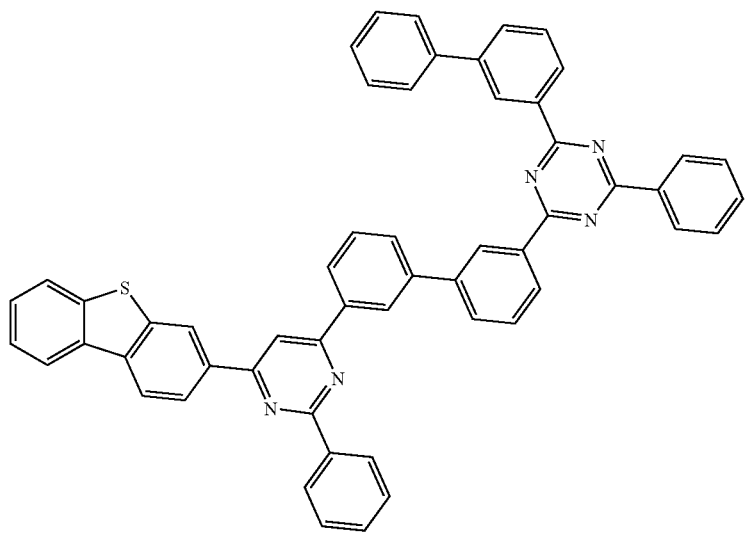
[A-38]
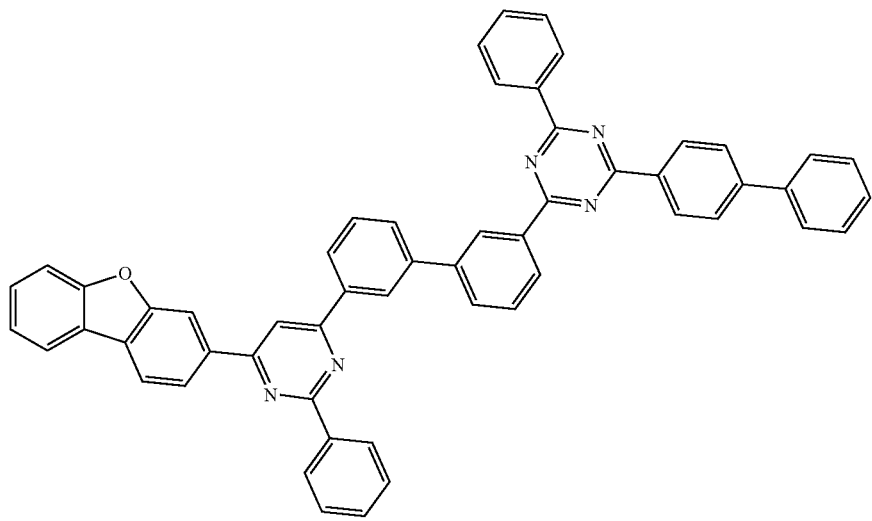
[A-39]
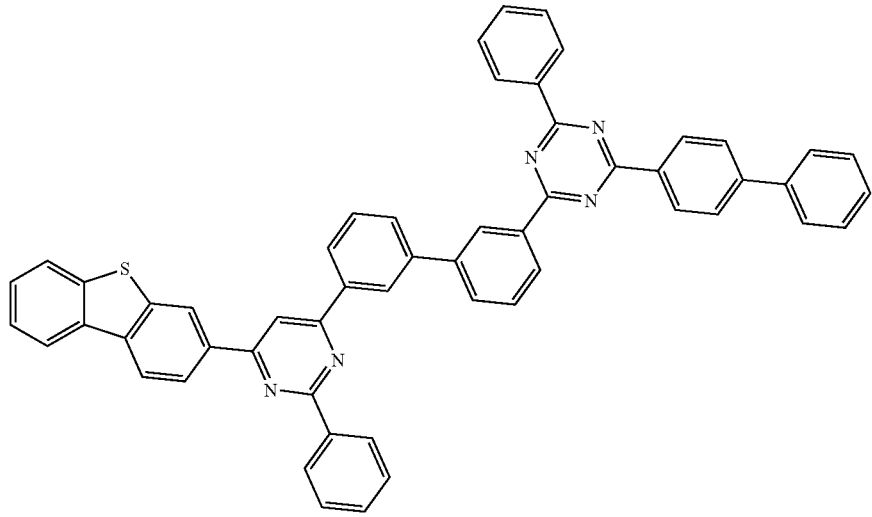
[A-40]

[A-41]
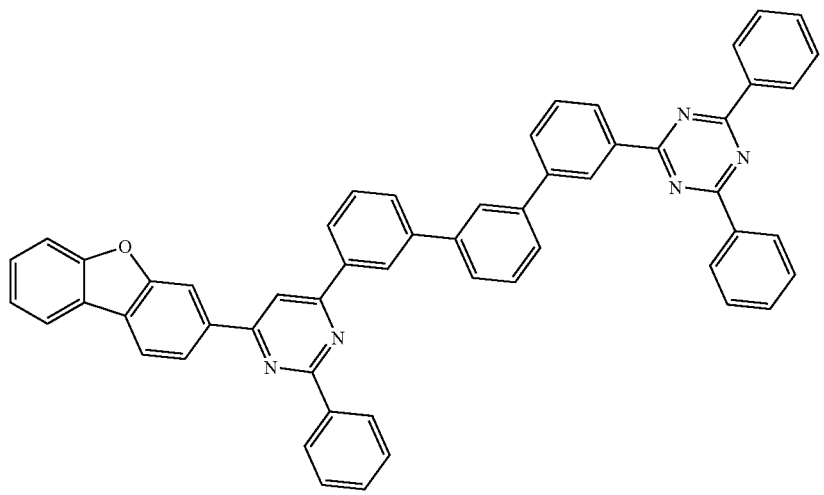
[A-42]
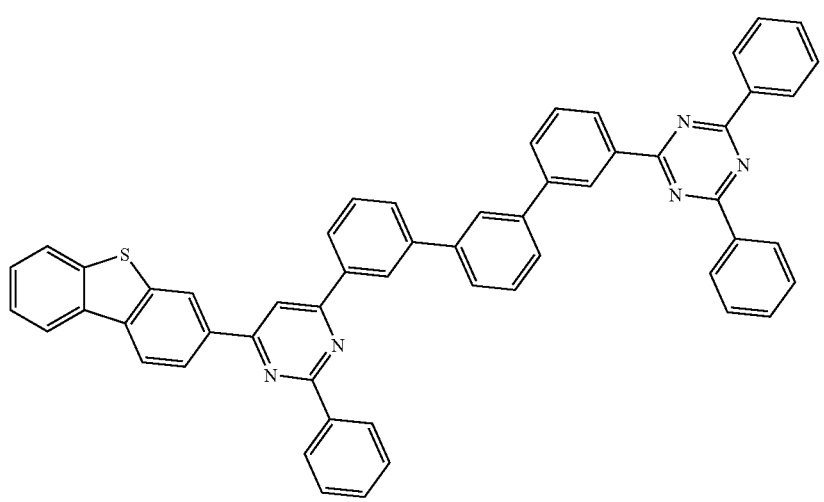
[A-43]
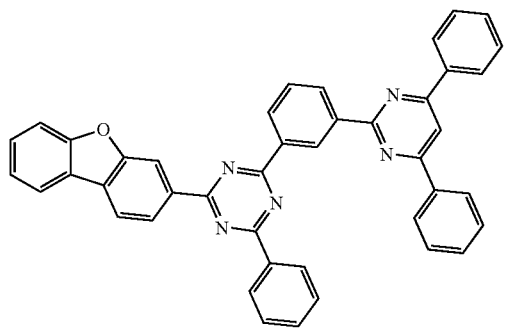
[A-44]
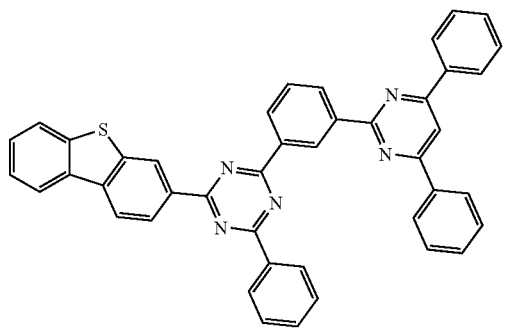
[A-45]
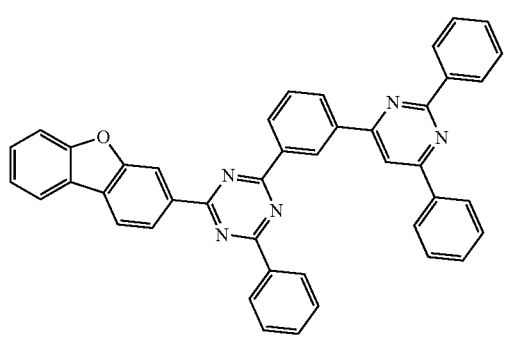
[A-46]
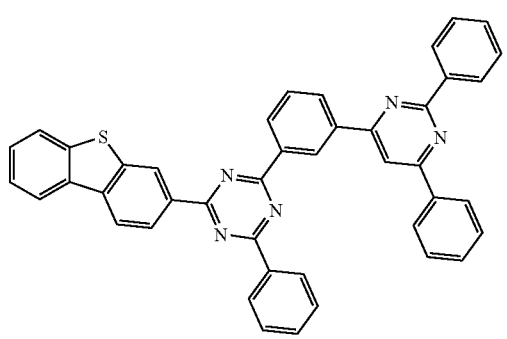

-continued
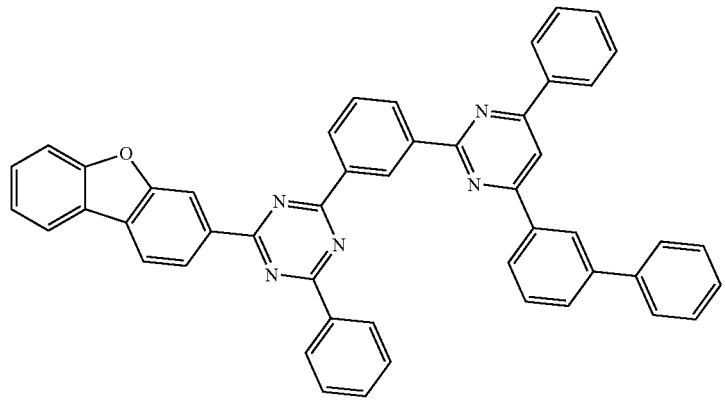
[A-47]
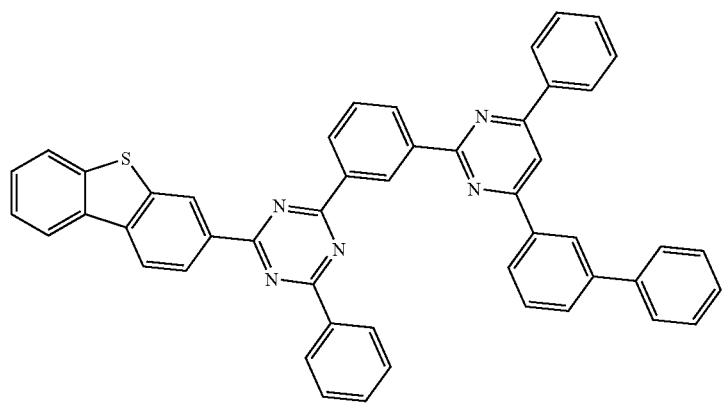
[A-48]
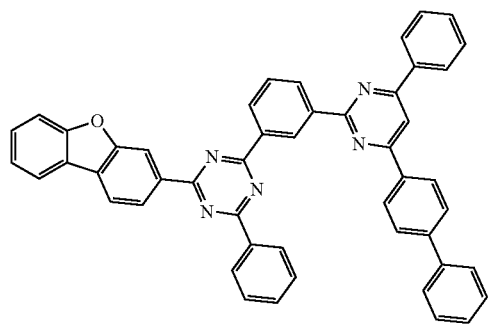
[A-49]
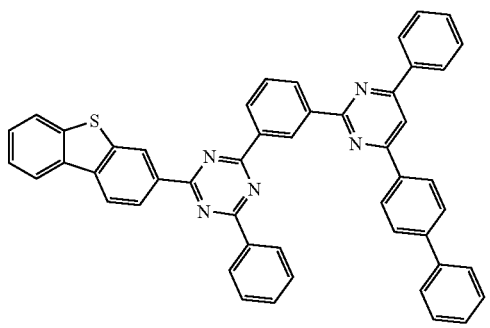
[A-50]
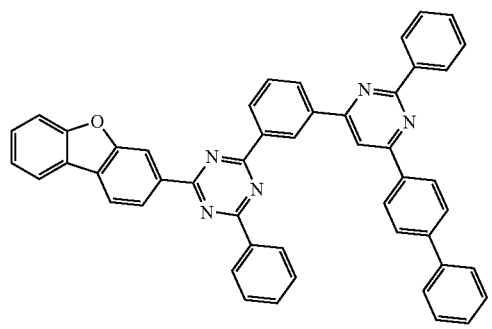
[A-51]
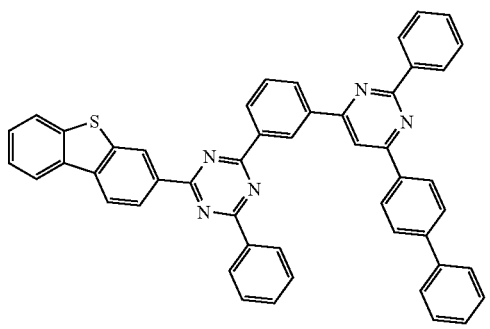
[A-52]

-continued
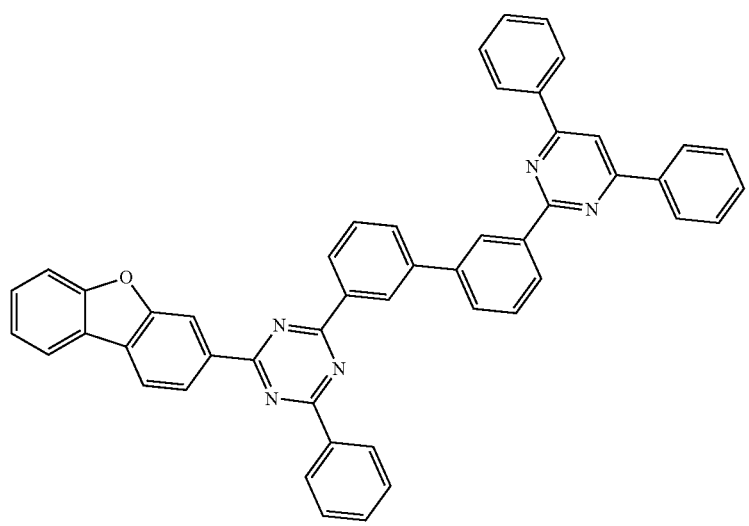
[A-53]
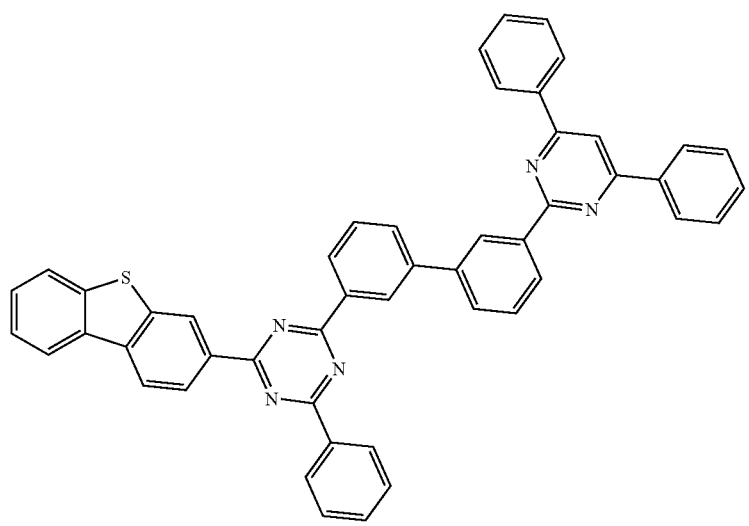
[A-54]
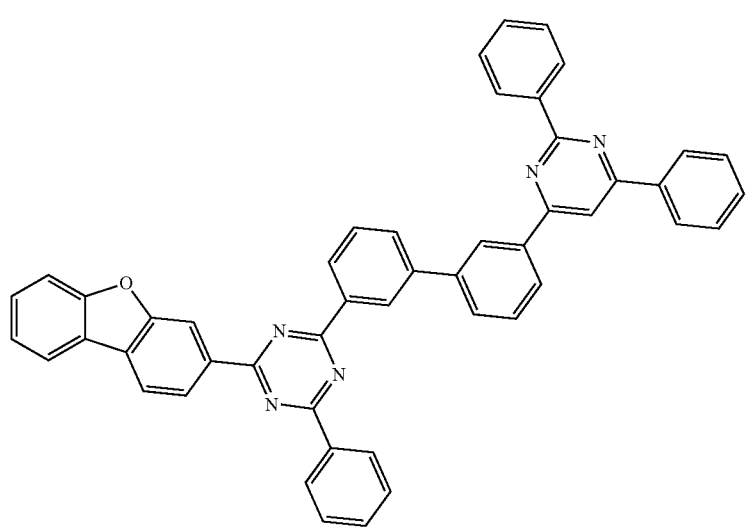
[A-55]

[A-56]

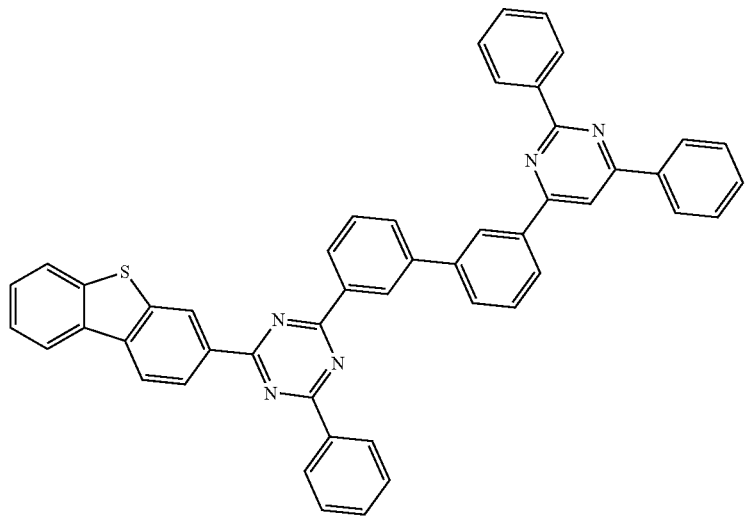

The first compound for an organic optoelectronic device may be applied to an organic optoelectronic device and may be applied in an organic optoelectronic device alone or with other compounds for an organic optoelectronic device. When the compound for an organic optoelectronic device is applied with other compounds for an organic optoelectronic device, it may be applied in a form of a composition.

Hereinafter, one example of a composition for an organic optoelectronic device including the first compound for an organic optoelectronic device is described.

The composition for an organic optoelectronic device according to another embodiment of the present invention includes the first compound for an organic optoelectronic device; and a second compound for an organic optoelectronic device represented by Chemical Formula 2.

[Chemical Formula 2]

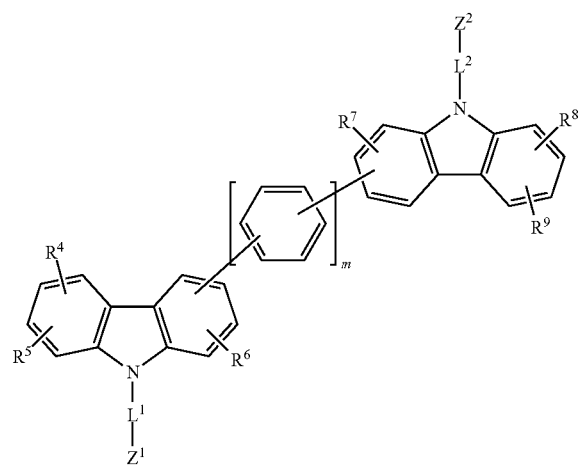

In Chemical Formula 2, $L^1$ and $L^2$ are independently a single bond, a substituted or unsubstituted C6 to C30 arylene group, a substituted or unsubstituted C2 to C30 heteroarylene group, or a combination thereof, $Z^1$ and $Z^2$ are independently a substituted or unsubstituted C6 to C30 aryl group, a substituted or unsubstituted C2 to C30 heterocyclic group, or a combination thereof, $R^4$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, m is one of integers of 0 to 2, and the "substituted" refers to replacement of at least one hydrogen by deuterium, a C1 to C4 alkyl group, a C6 to C18 aryl group, or a C2 to C30 heteroaryl group. In a more specific example embodiment of the present invention, the "substituted" refers to replacement of at least one hydrogen by deuterium, a phenyl group, an ortho-biphenyl group, a meta-biphenyl group, a para-biphenyl group, a terphenyl group, a naphthyl group, a dibenzofuranyl group, or a dibenzothiophenyl group.

In an example embodiment of the present invention, $L^1$ and $L^2$ of Chemical Formula 2 may independently be a single bond, or a substituted or unsubstituted C6 to C18 arylene group. Specifically, $L^1$ and $L^2$ may be a single bond, a meta-phenylene group, or a para-phenylene group.

In an example embodiment of the present invention, $Z^1$ and $Z^2$ of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylene group, a substituted or unsubstituted pyridinyl group, a substituted or unsubstituted pyrimidinyl group, a substituted or unsubstituted quinazolyl group, a substituted or unsubstituted dibenzothiophenyl group, a substituted or unsubstituted dibenzofuranyl group, a substituted or unsubstituted triazinyl group, a substituted or unsubstituted quinolinyl group, a substituted or unsubstituted isoquinolinyl group, a substituted or unsubstituted carbazolyl group, a substituted or unsubstituted fluorenyl group, or a combination thereof. Specifically, $Z^1$ and $Z^2$ may be a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted dibenzothiophenyl group, or a substituted or unsubstituted dibenzofuranyl group.

In an example embodiment of the present invention, $R^4$ to $R^9$ of Chemical Formula 2 may independently be hydrogen, deuterium, or a substituted or unsubstituted C6 to C12 aryl group. Specifically, $R^4$ to $R^9$ may be hydrogen or a phenyl group, and for example one of $R^4$ to $R^9$ may be a phenyl group and the remainder may be hydrogen.

In an example embodiment of the present invention, m of Chemical Formula 2 may be 0 or 1.

In a specific example embodiment of the present invention, Chemical Formula 2 may have one of structures of Group I and the $*$-$L^1$-$Z^1$ and $*$-$L^2$-$Z^2$ may be one of substituents of Group II.

[Group I]

C-1
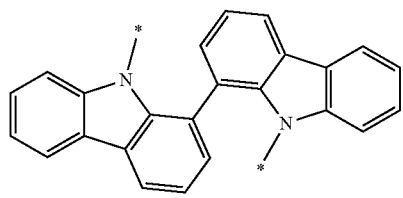

C-2
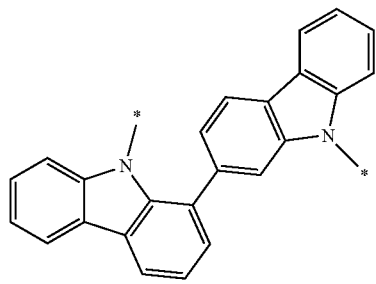

C-3
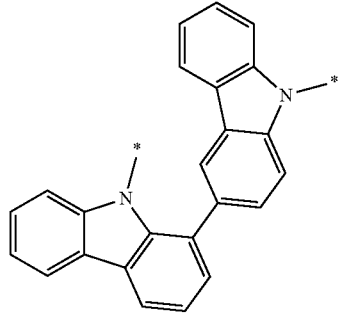

C-4
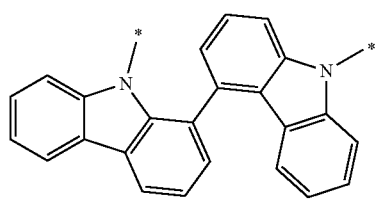

C-5
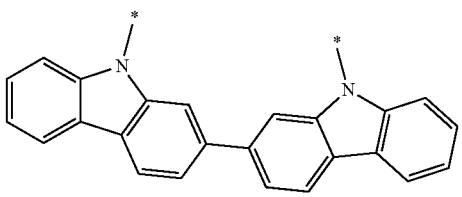

C-6
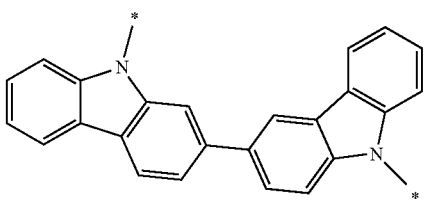

C-7
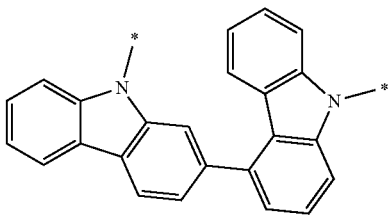

C-8
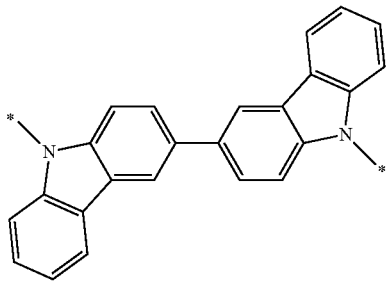

C-9
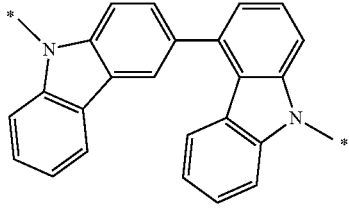

C-10
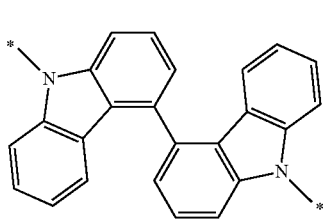

C-11
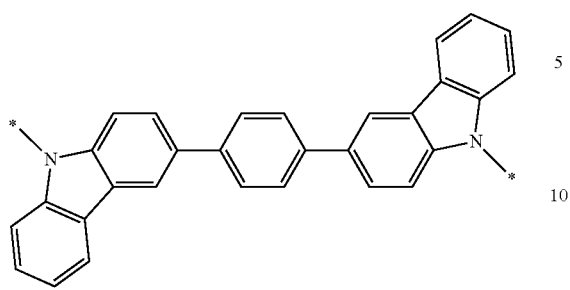
C-12
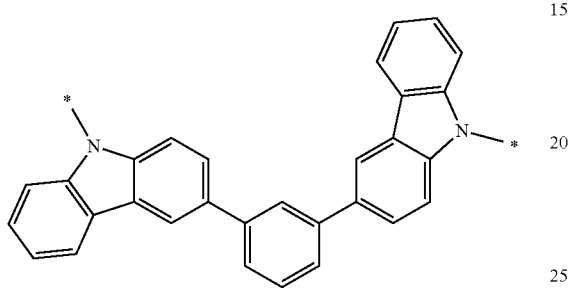
C-13
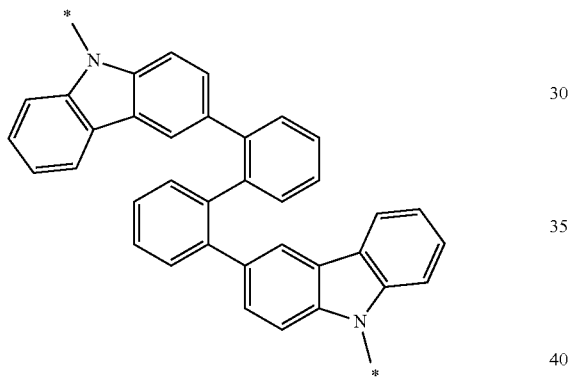
C-14
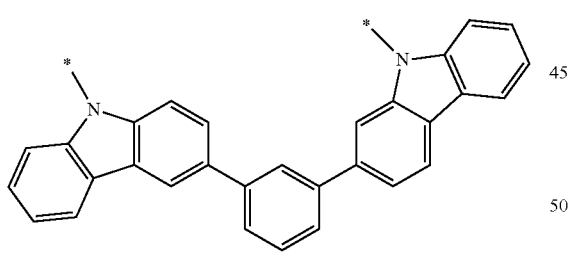
C-15
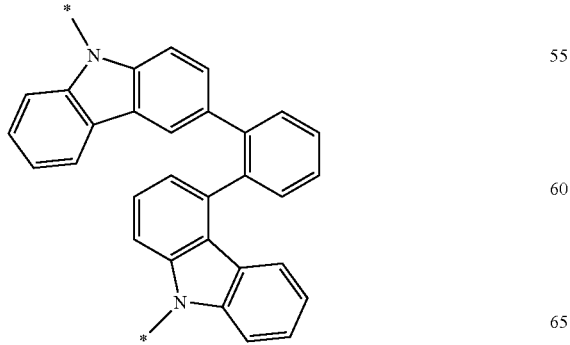
C-16
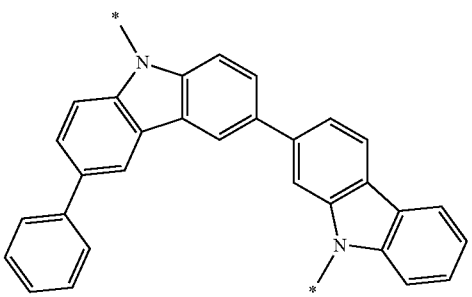
C-17
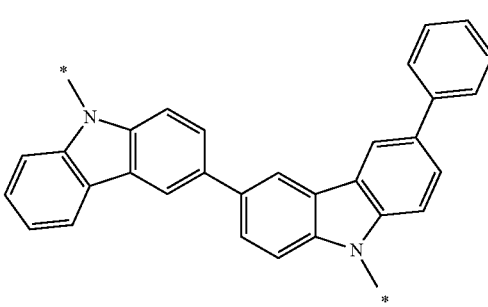
C-18
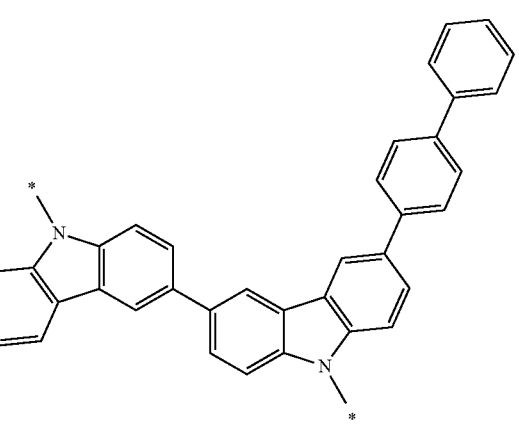
[Group II]
B-1
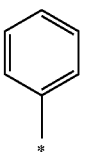

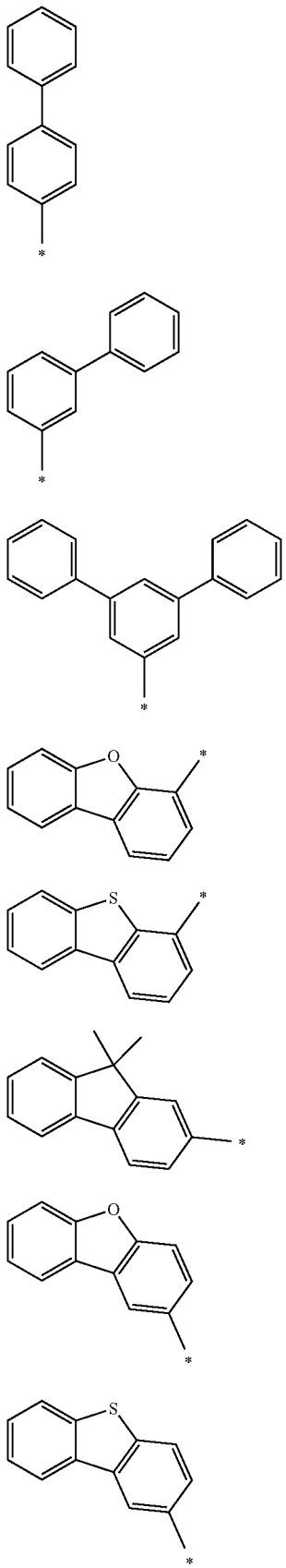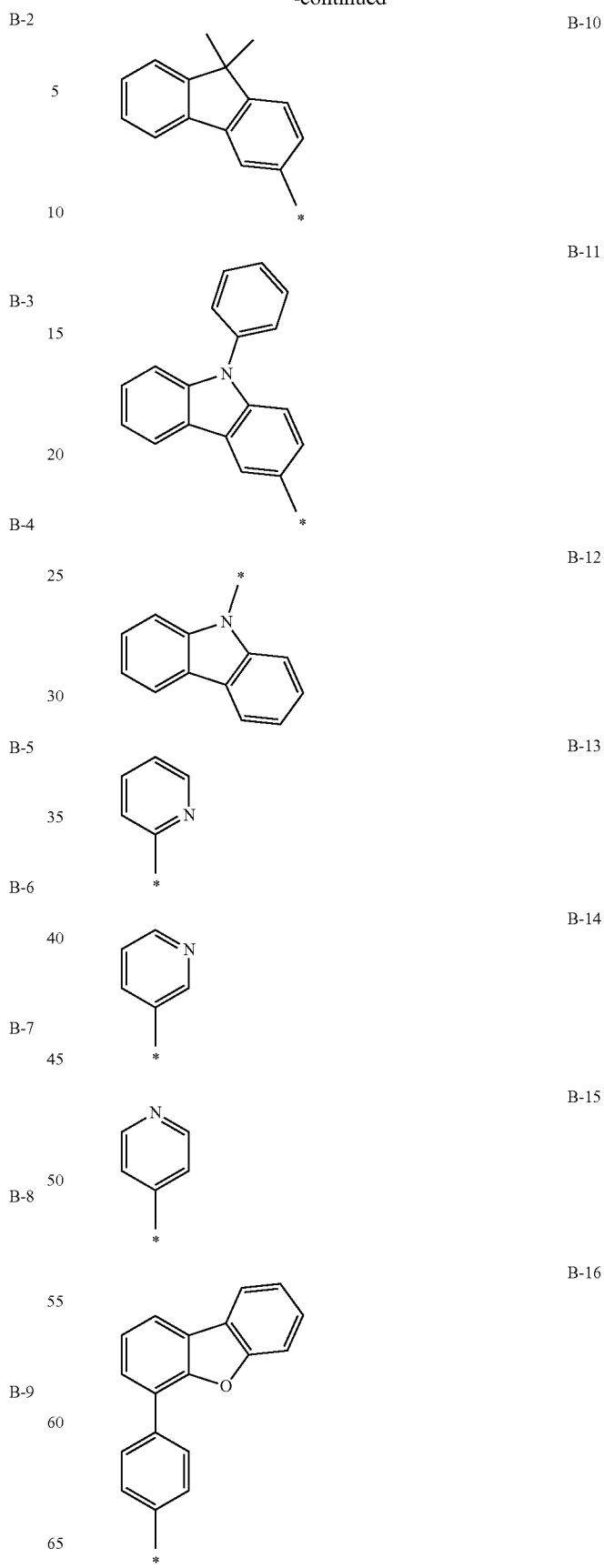

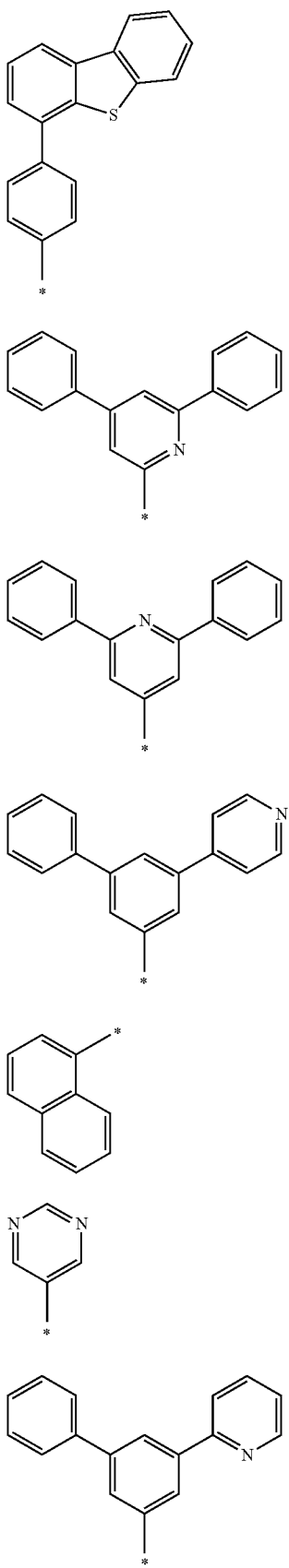
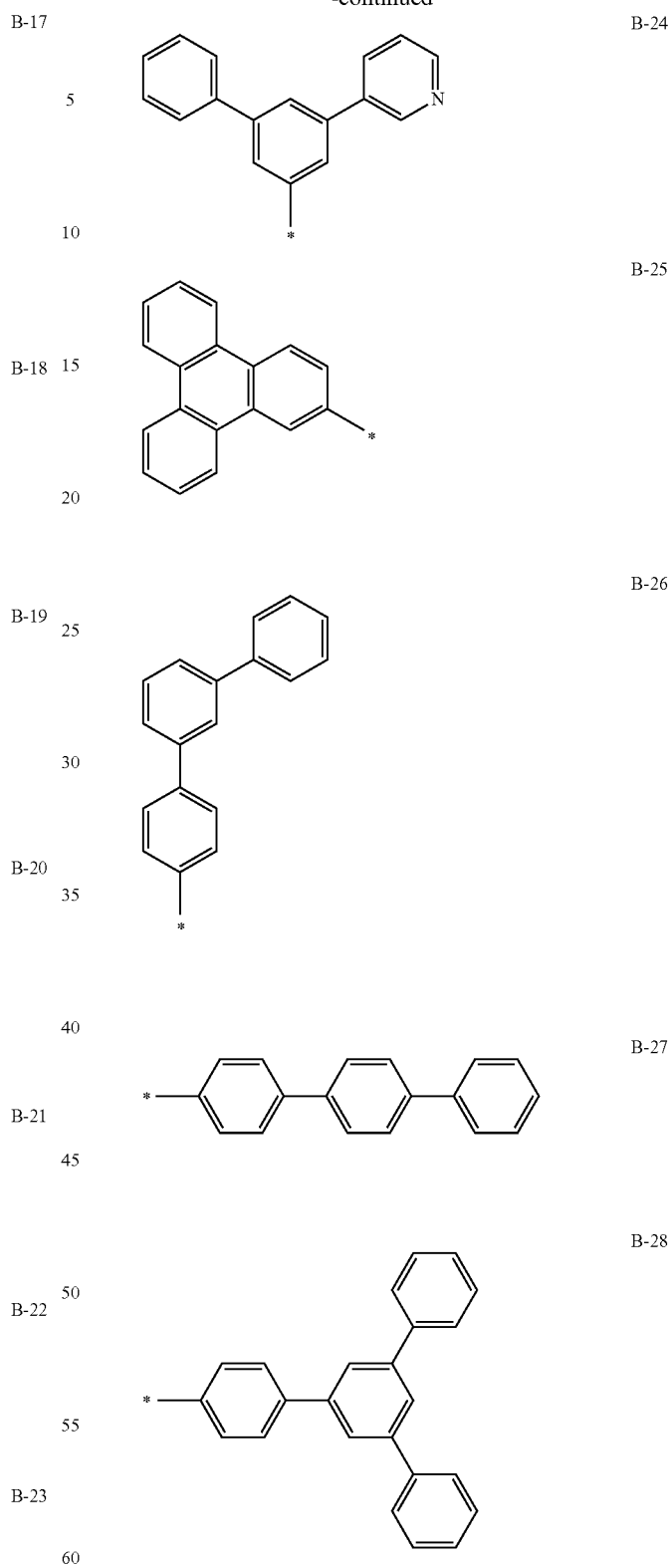
In Groups I and II, * is a linking point.
The second compound for an organic optoelectronic device represented by Chemical Formula 2 may be for example selected from compounds of Group 2.

[Group 2]
[E-1]
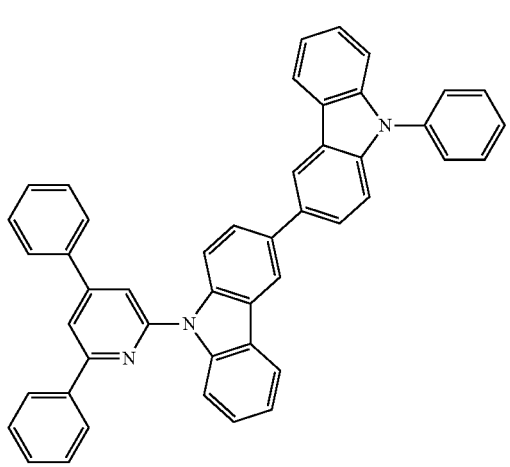
[E-2]
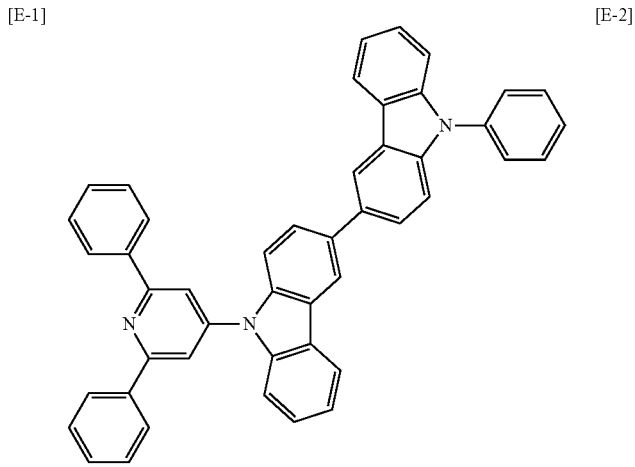
[E-3]
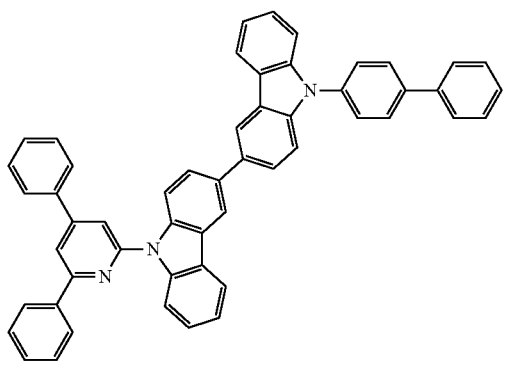
[E-4]
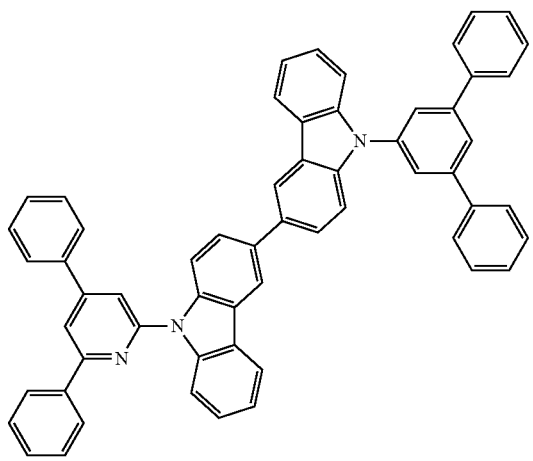
[E-5]
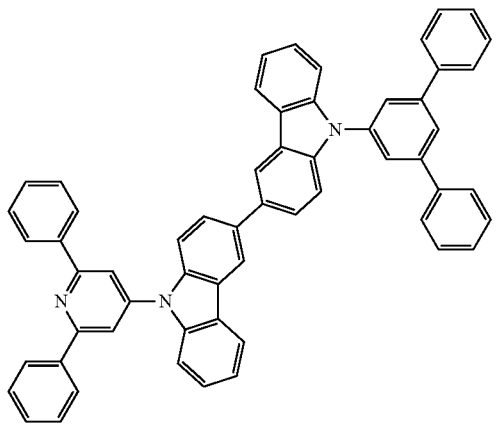
[E-6]
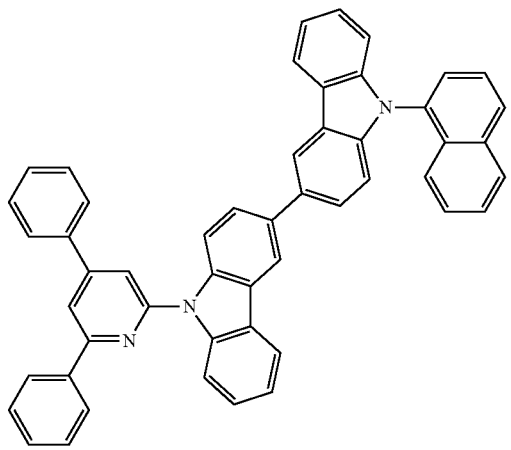

-continued
[E-7]
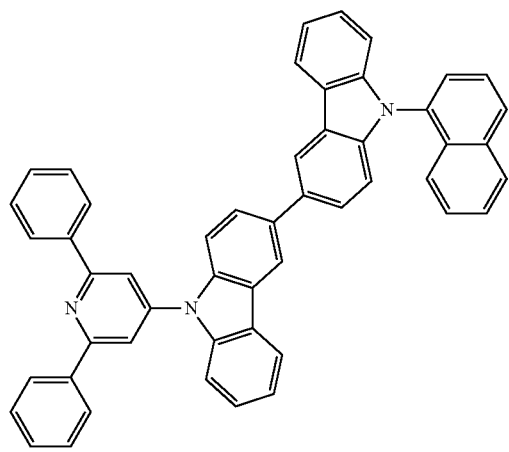
[E-8]
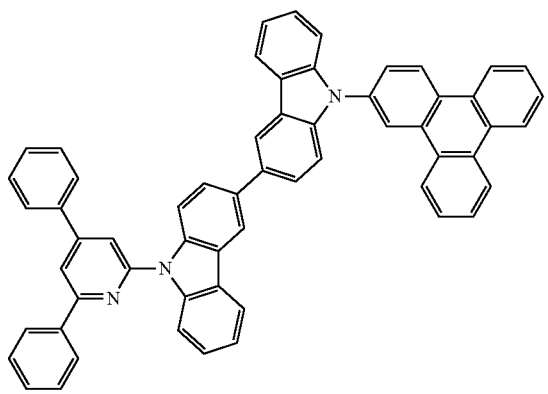
[E-9]
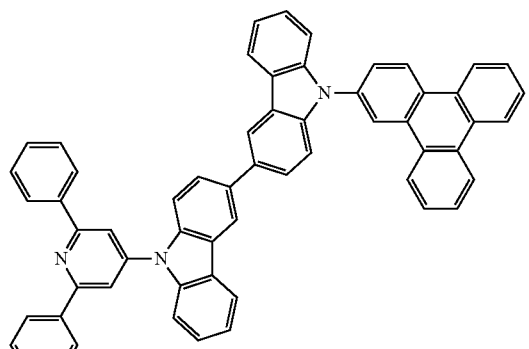
[E-10]
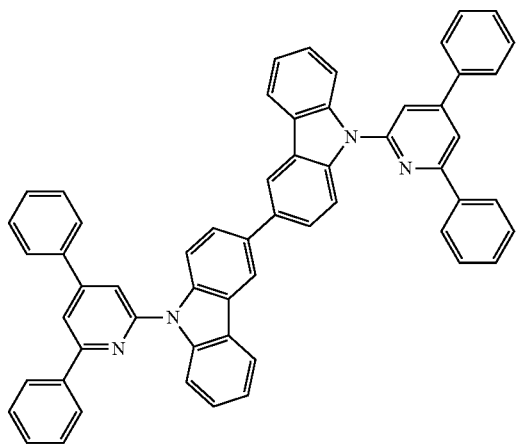
[E-11]
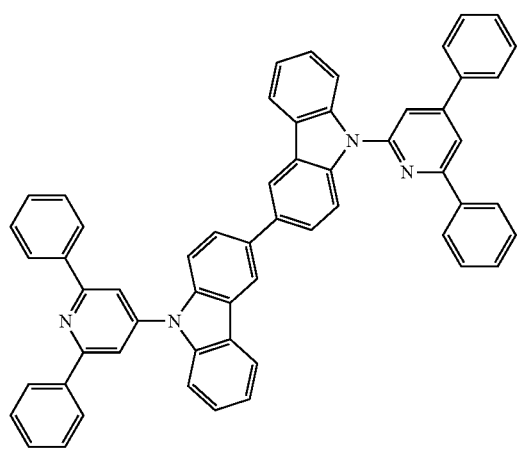
[E-12]
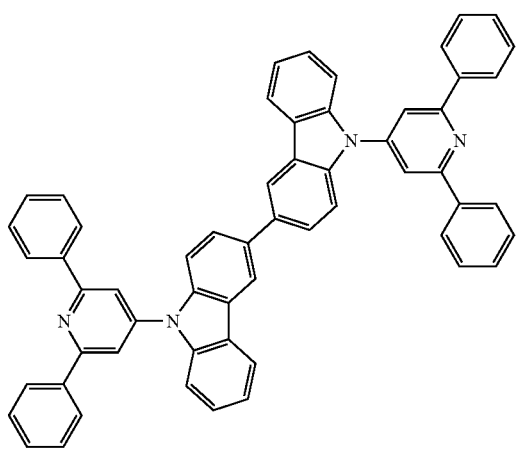

-continued
[E-13]
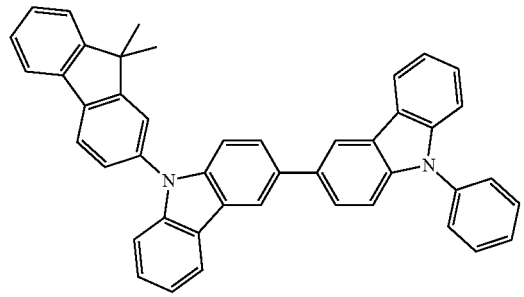
[E-14]
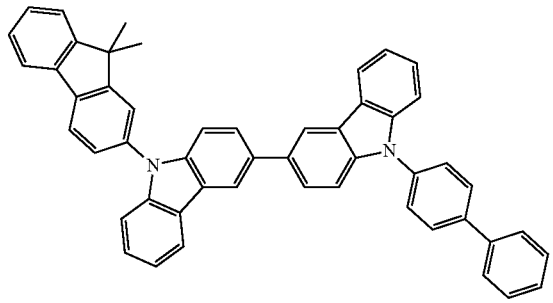
[E-15]
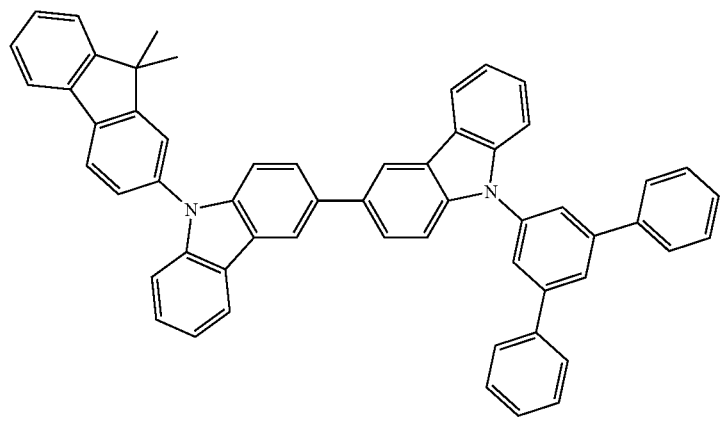
[E-16]
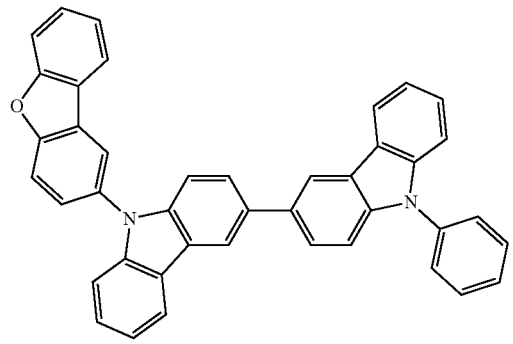
[E-17]
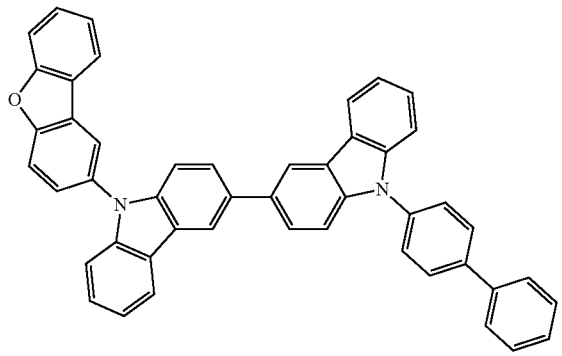
[E-18]
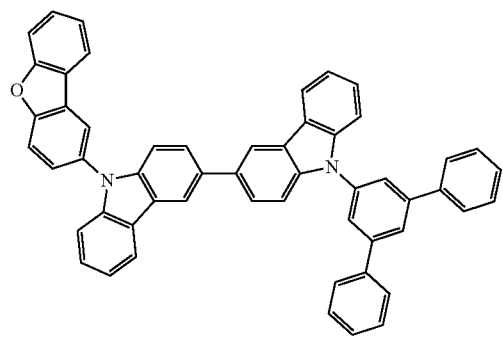
[E-19]
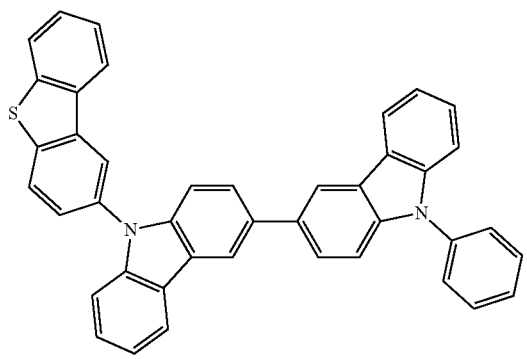

-continued
[E-20]
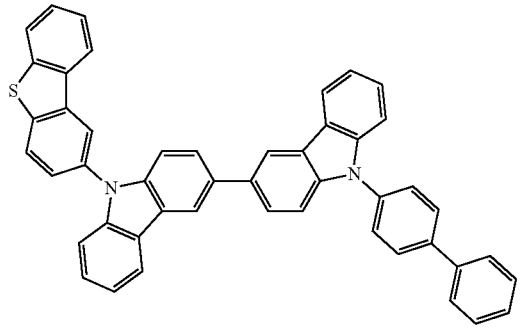
[E-21]
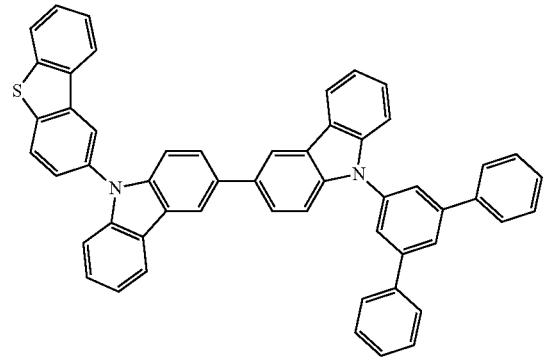
[E-22]
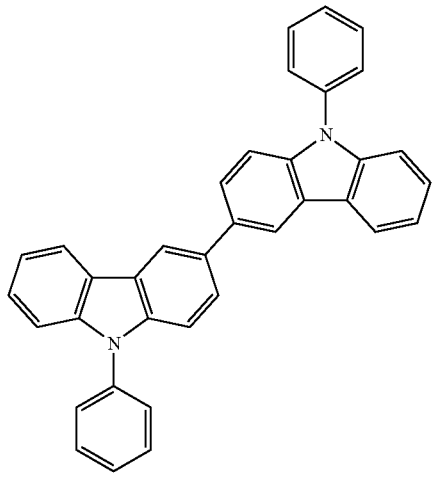
[E-23]
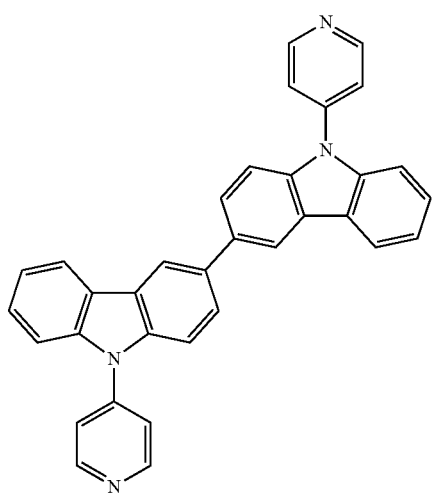
[E-24]
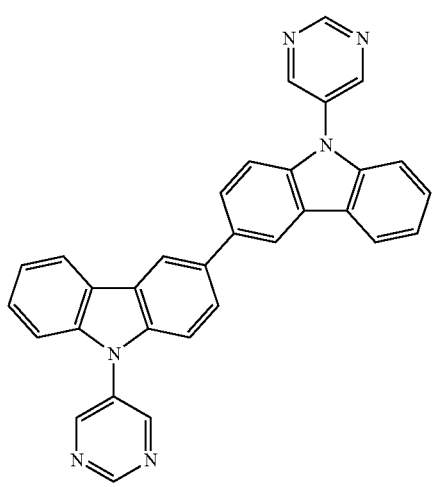
[E-25]
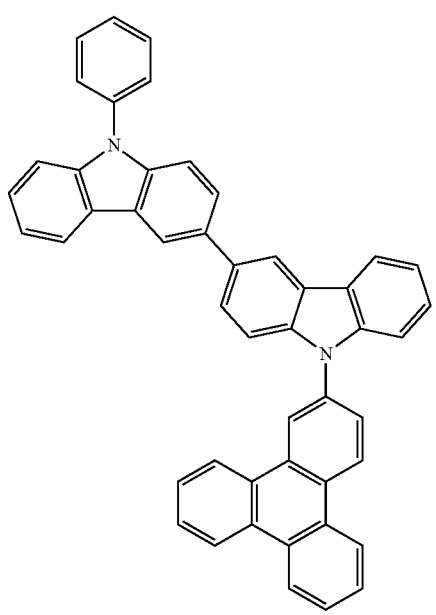

-continued
[E-26]
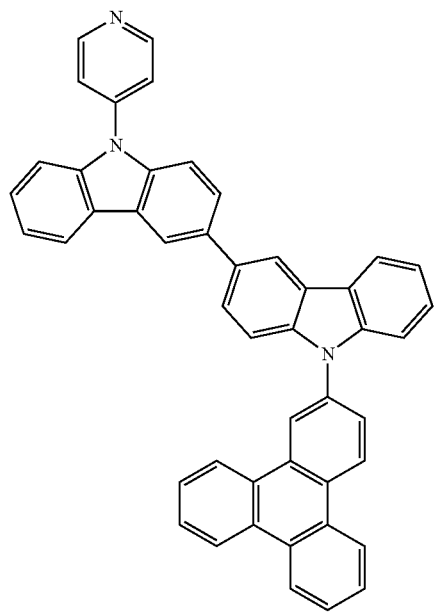
[E-27]
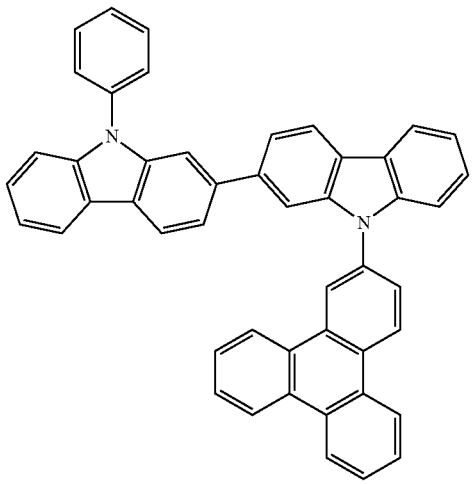
[E-28]
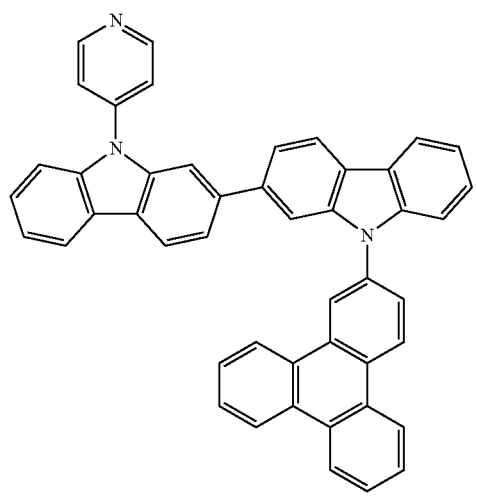
[E-29]
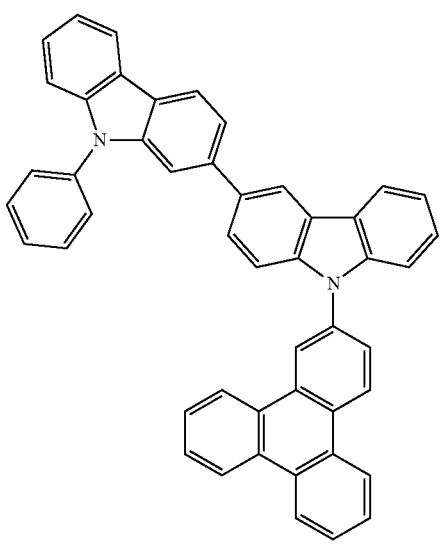

[E-30]
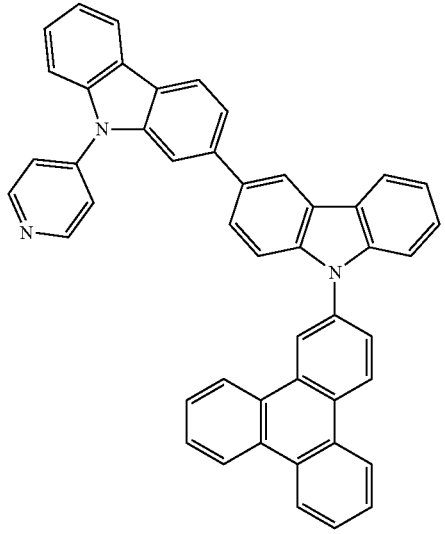
[E-31]
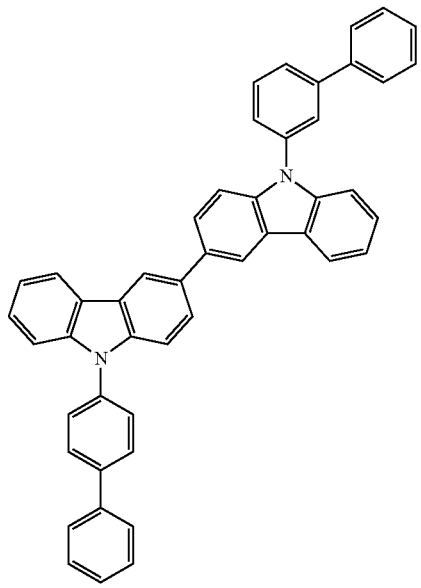
[E-32]
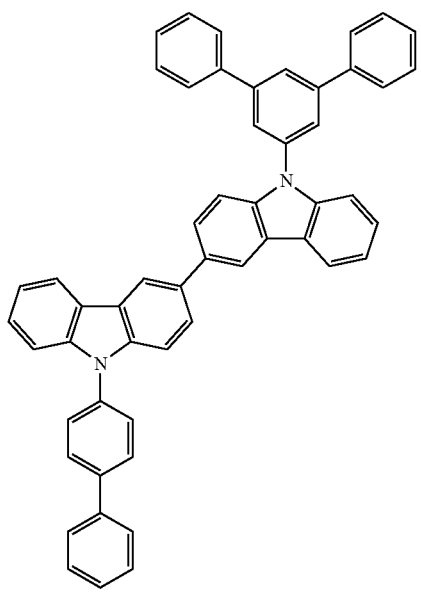
[E-33]
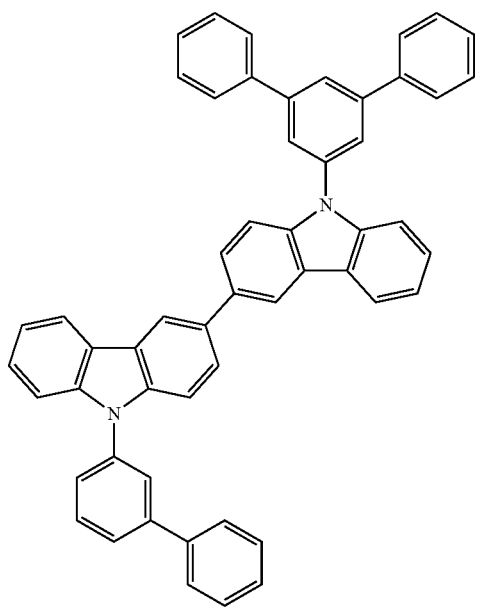

-continued
[E-34]
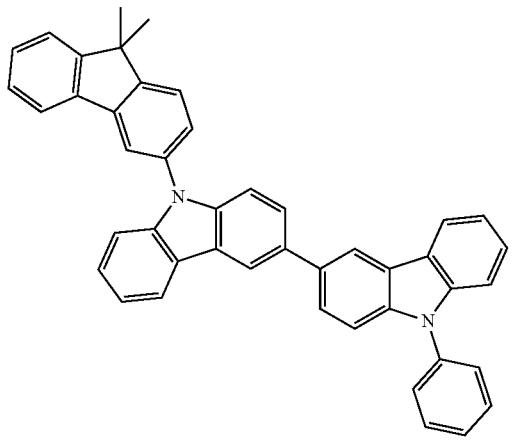
[E-35]
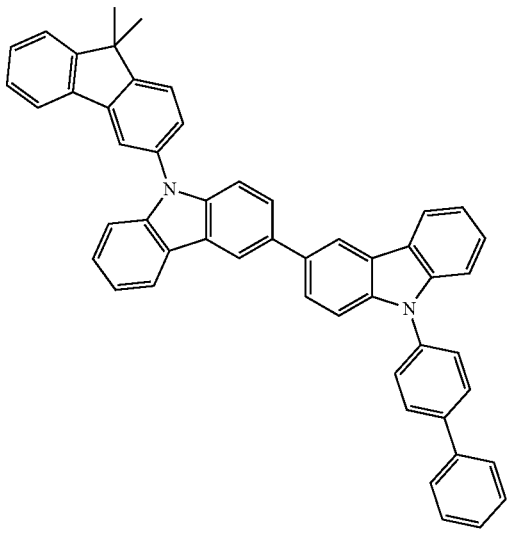
[E-36]
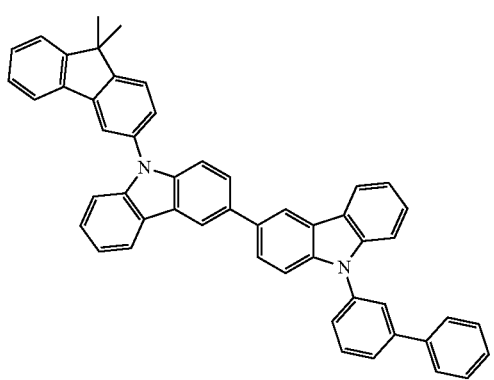
[E-37]
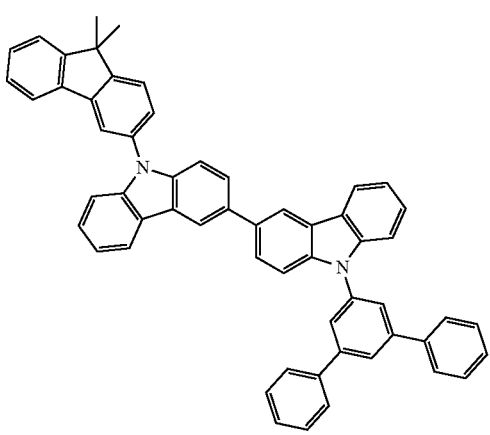
[E-38]
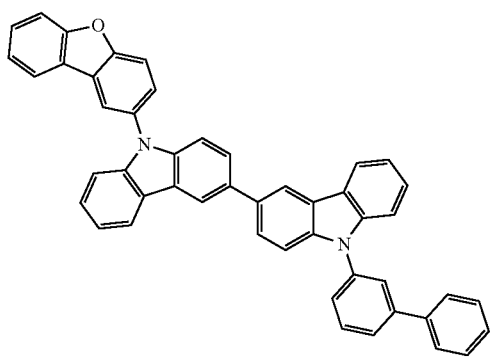
[E-39]
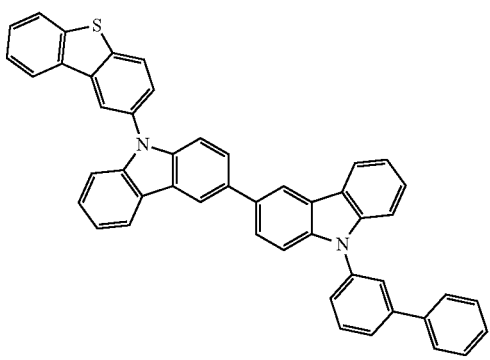

-continued
[E-40]
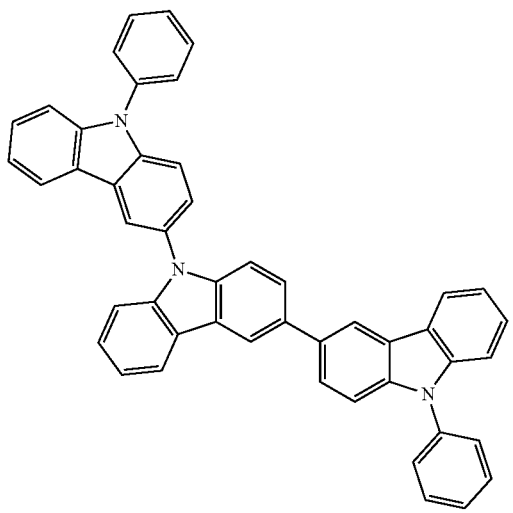
[E-41]
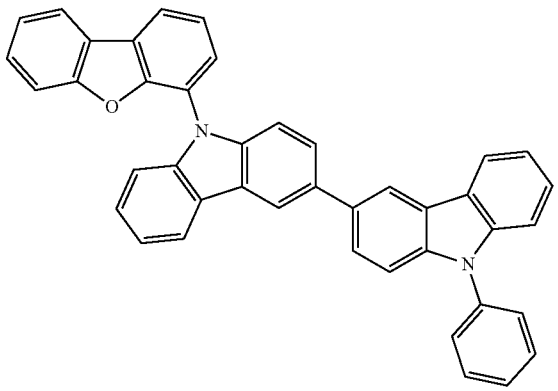
[E-42]
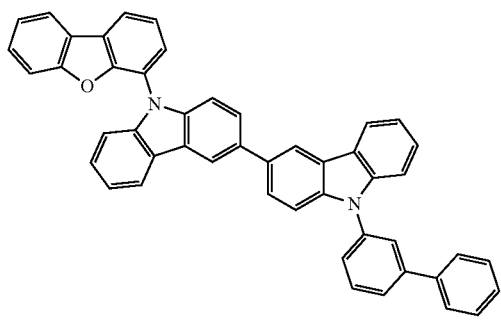
[E-43]
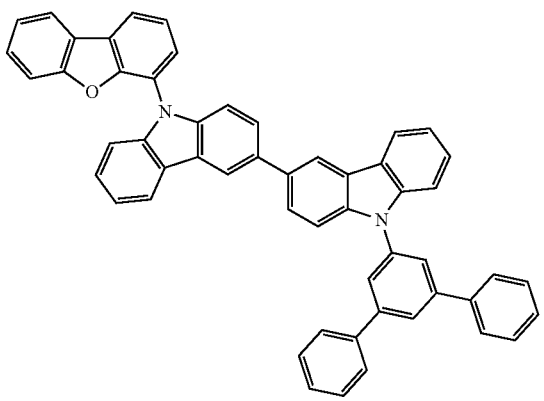
[E-44]
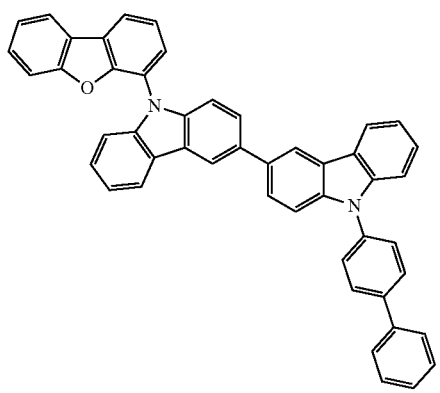
[E-45]
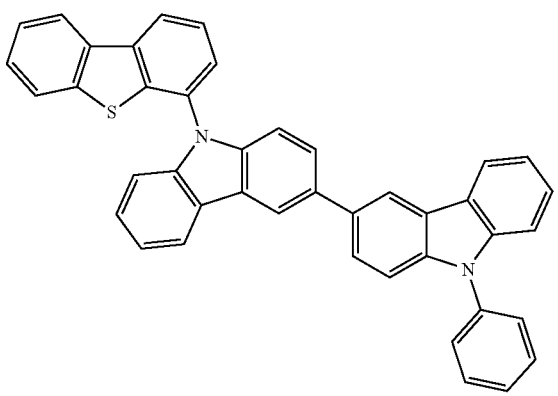

-continued
[E-46]
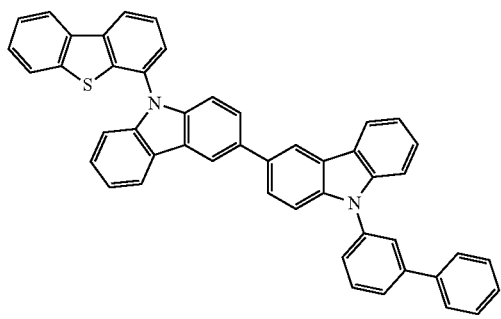
[E-47]
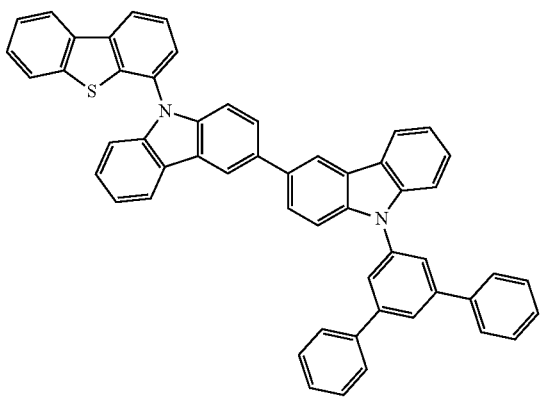
[E-48]
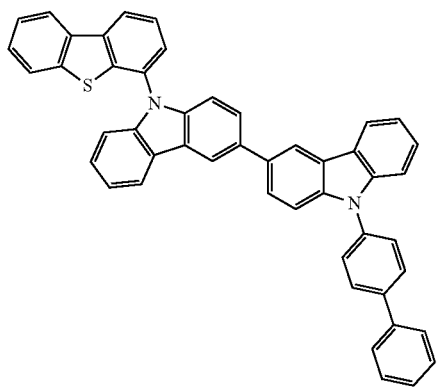
[E-49]
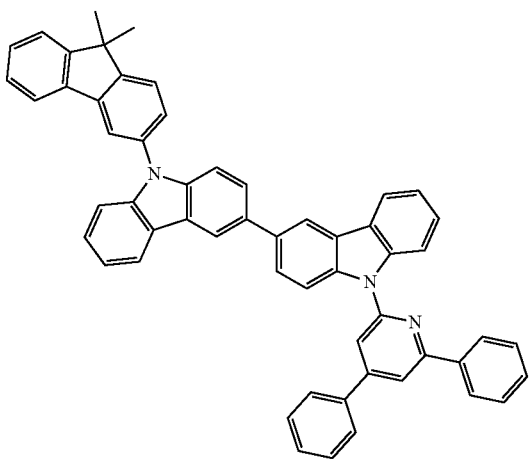
[E-50]
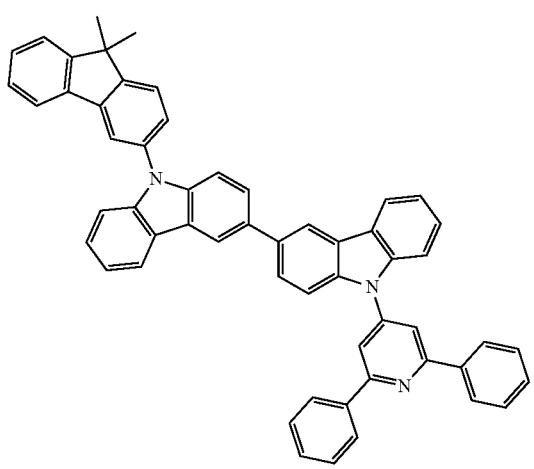
[E-51]
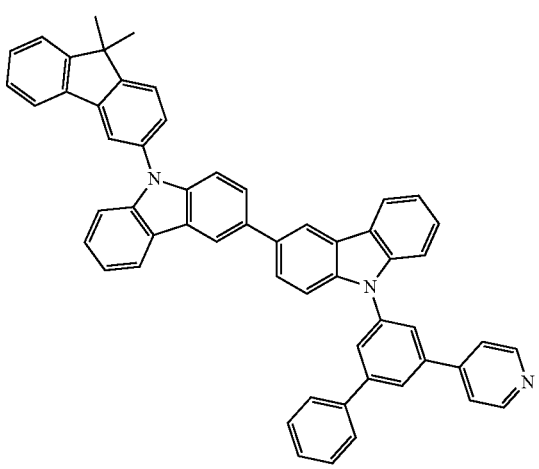

[E-52]
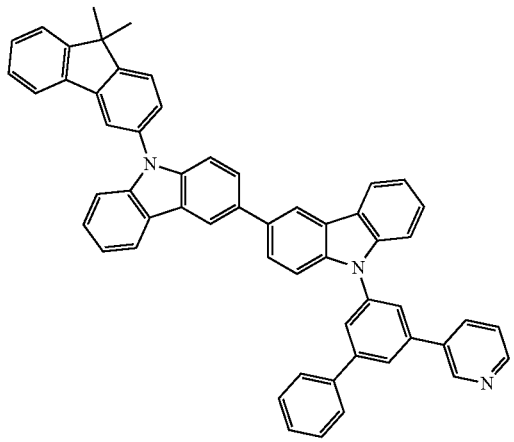
[E-53]
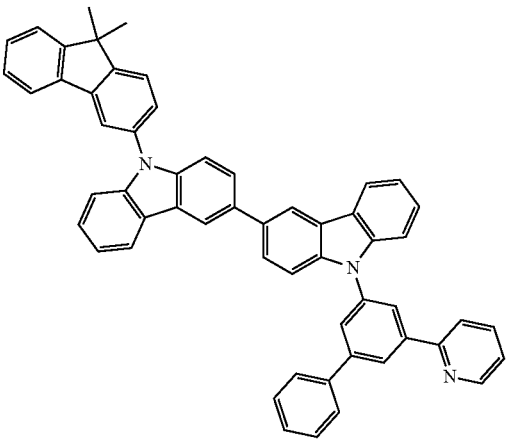
[E-54]
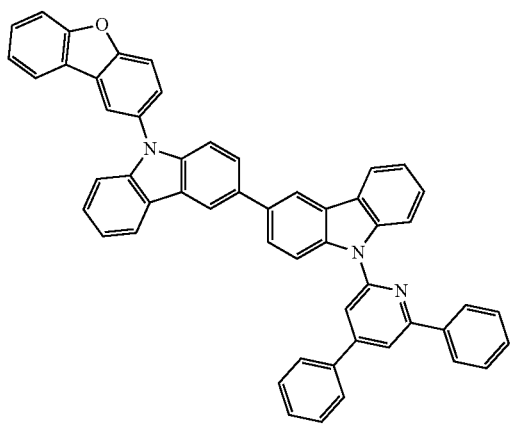
[E-55]
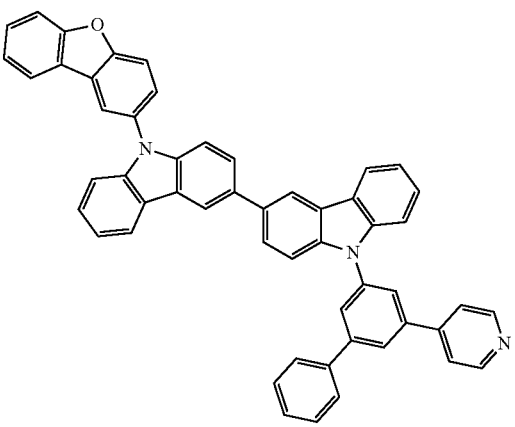
[E-56]
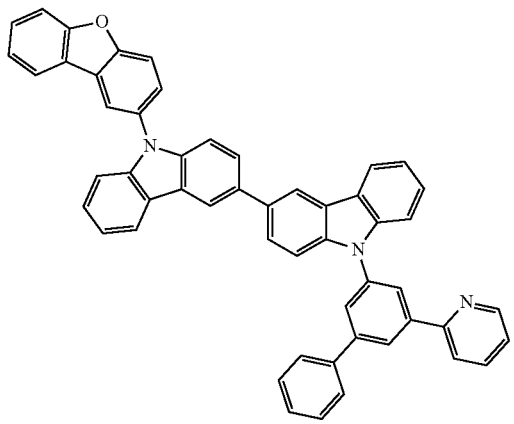
[E-57]
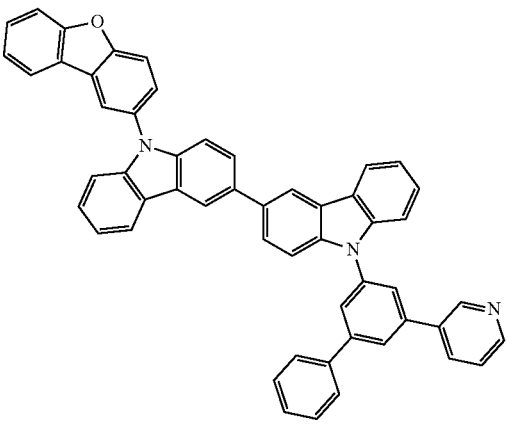

-continued
[E-58]
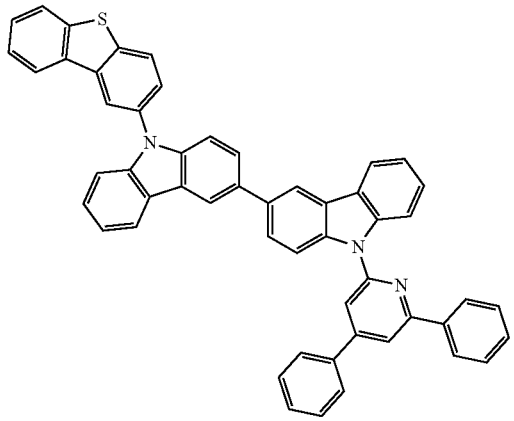
[E-59]
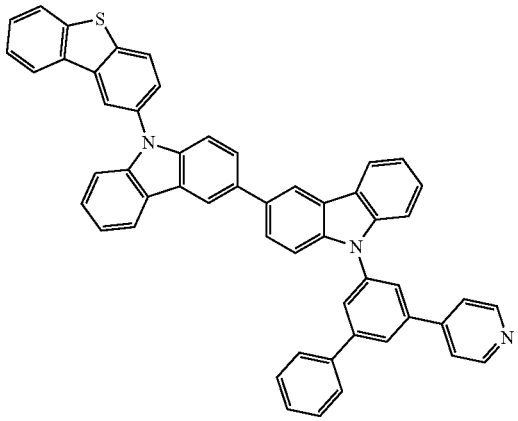
[E-60]
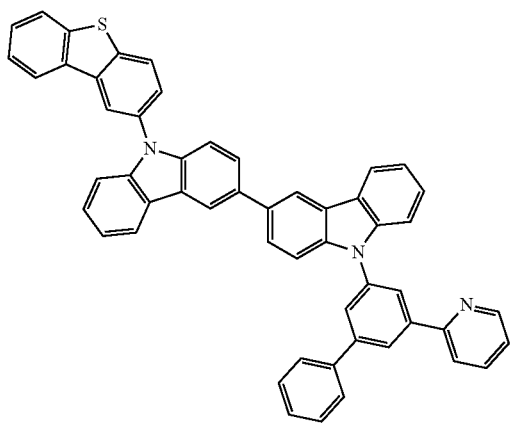
[E-61]
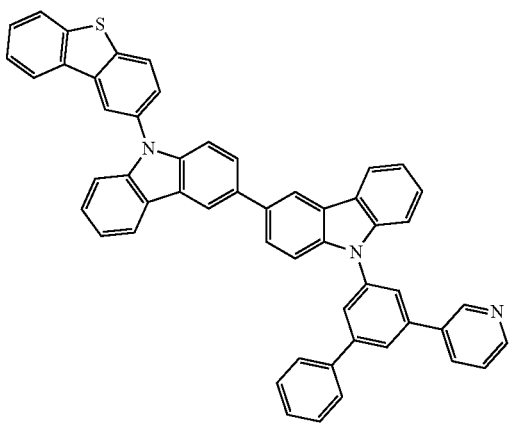
[E-62]
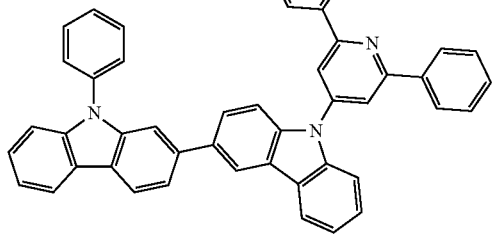
[E-63]
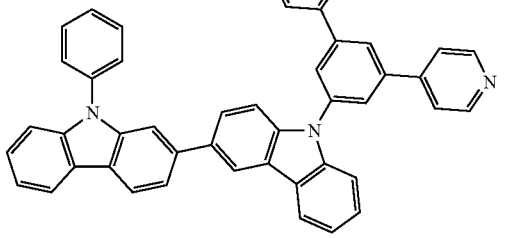
[E-64]
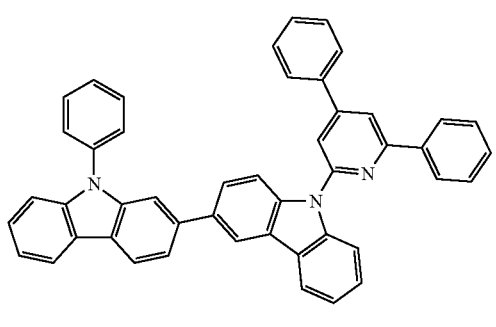
[E-65]

-continued
[E-66]
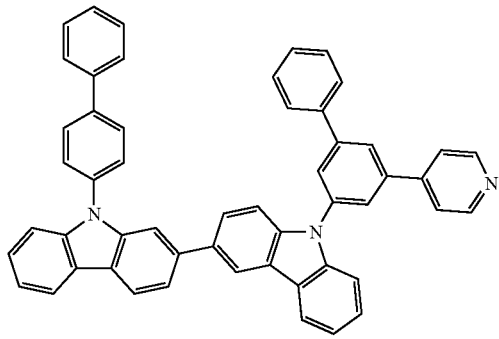
[E-67]
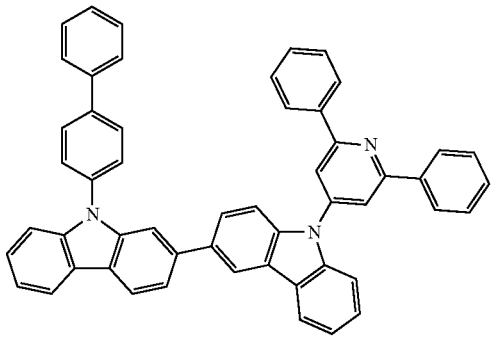
[E-68]
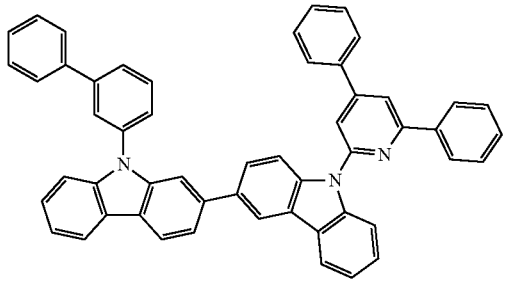
[E-69]
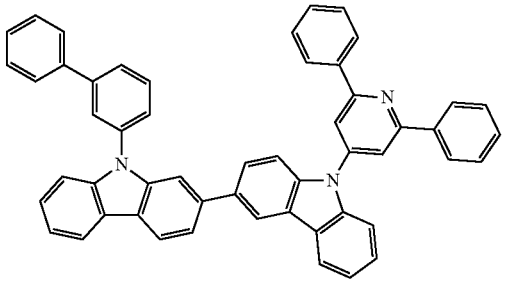
[E-70]
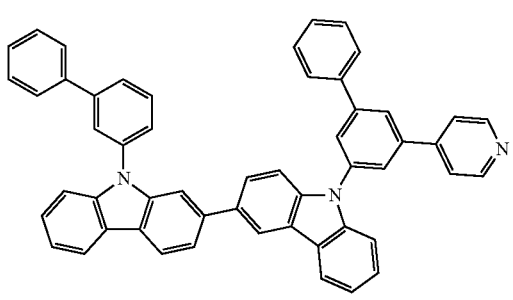
[E-71]
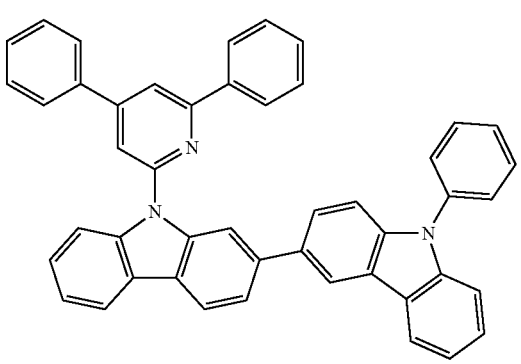
[E-72]
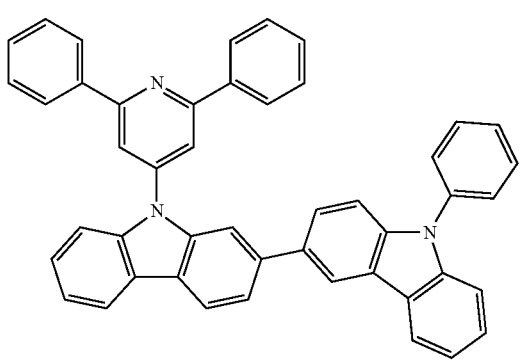
[E-73]
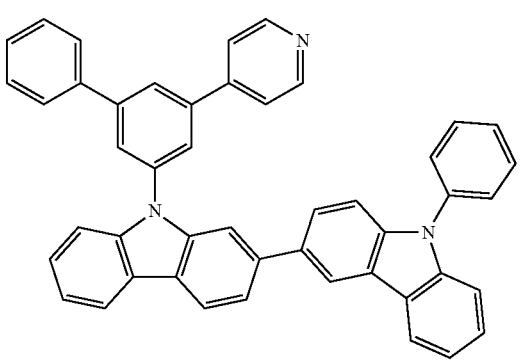

-continued
[E-74]
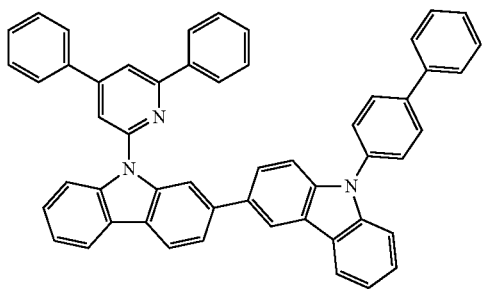
[E-75]
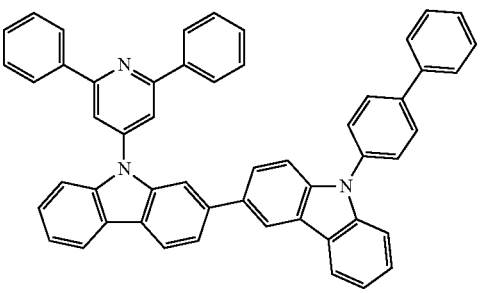
[E-76]
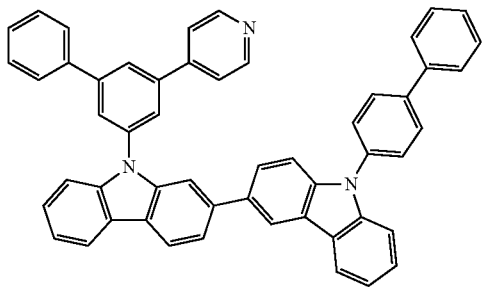
[E-77]
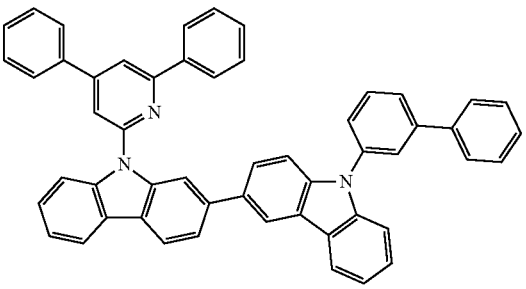
[E-78]
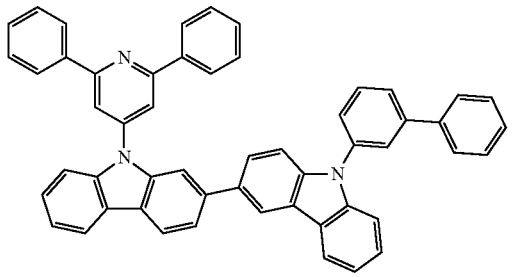
[E-79]
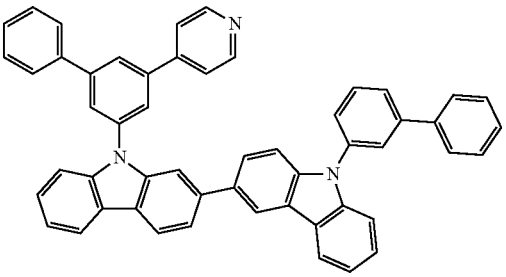
[E-80]
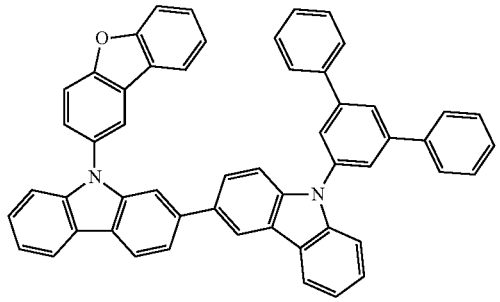
[E-81]
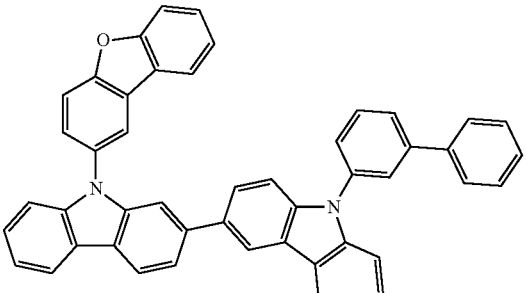
[E-82]
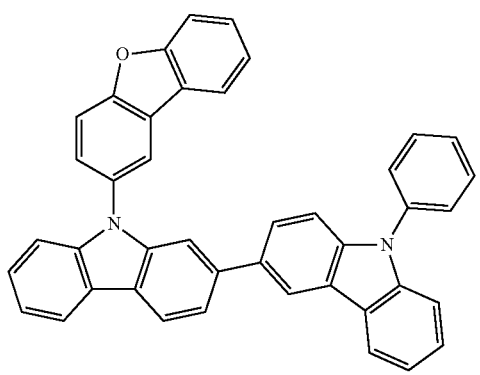
[E-83]
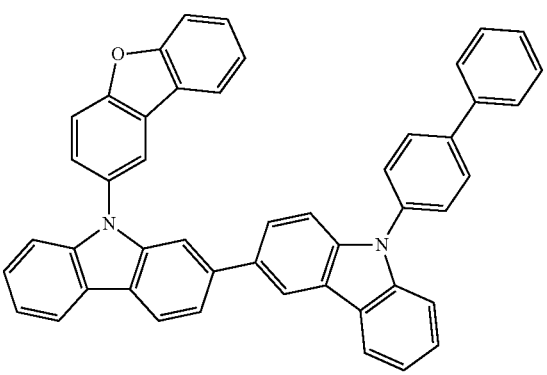

-continued
[E-84]
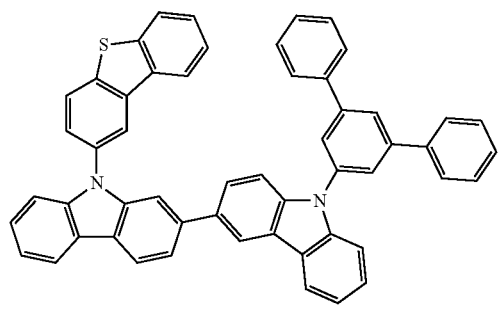
[E-85]
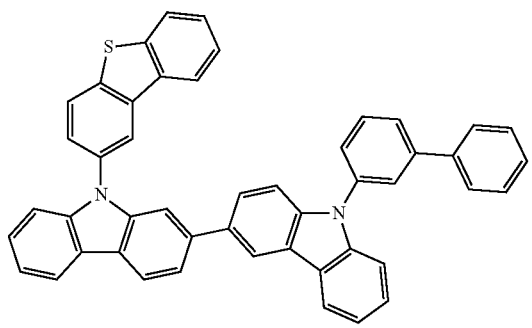
[E-86]
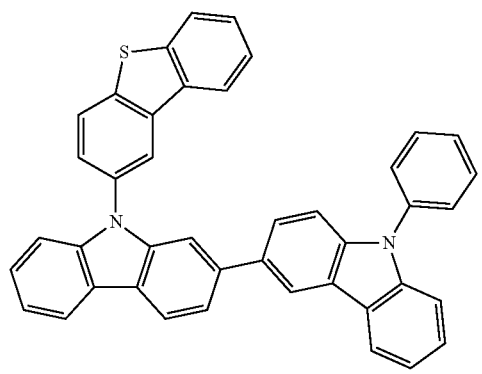
[E-87]
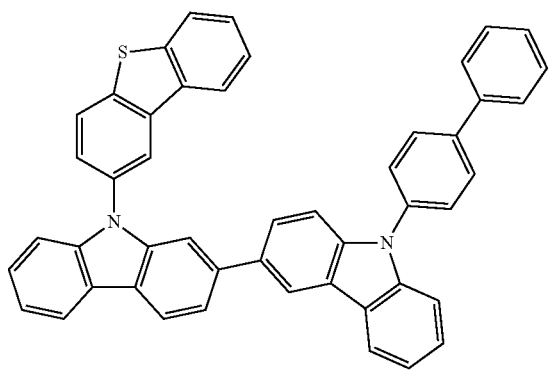
[E-88]
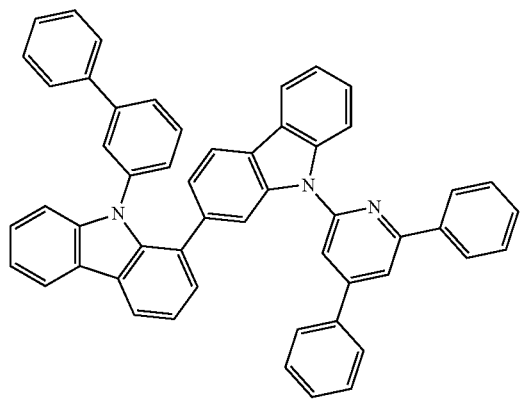
[E-89]
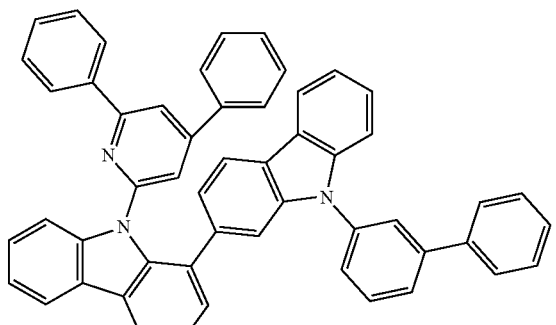
[E-90]
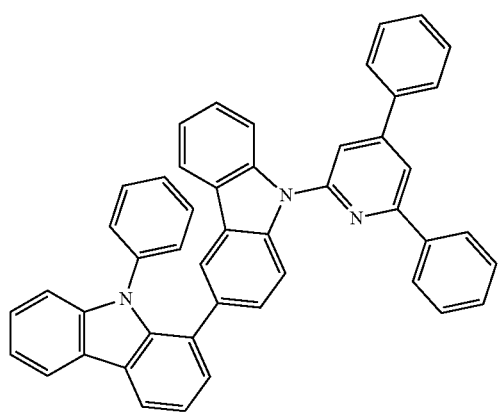
[E-91]
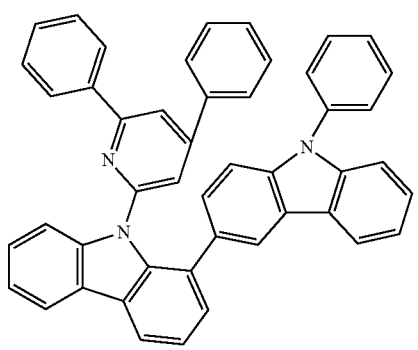

-continued
[E-92]
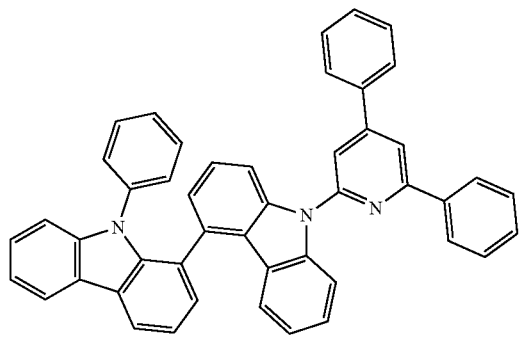
[E-93]
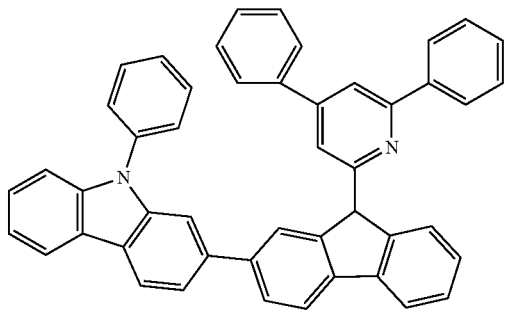
[E-94]
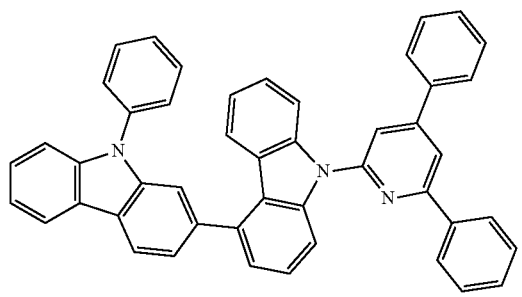
[E-95]
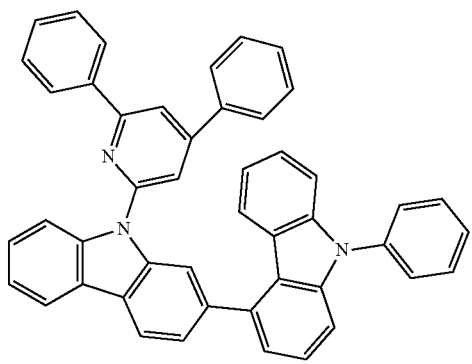
[E-96]
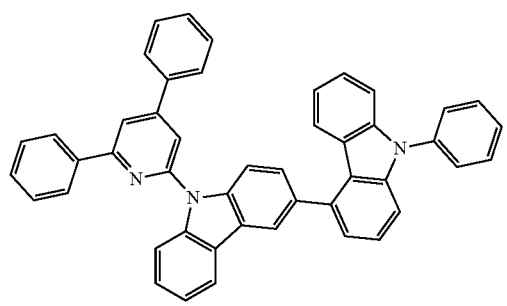
[E-97]
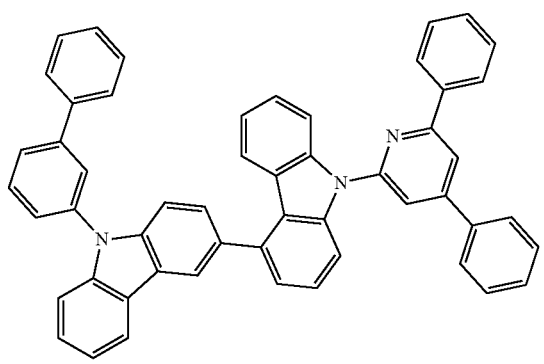

-continued
[E-98]
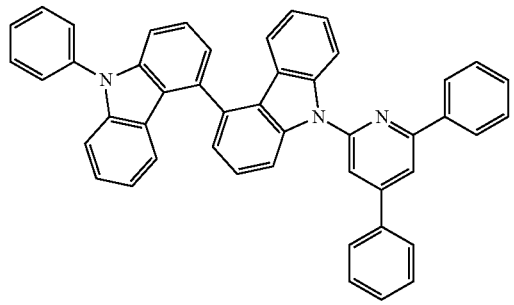
[E-99]
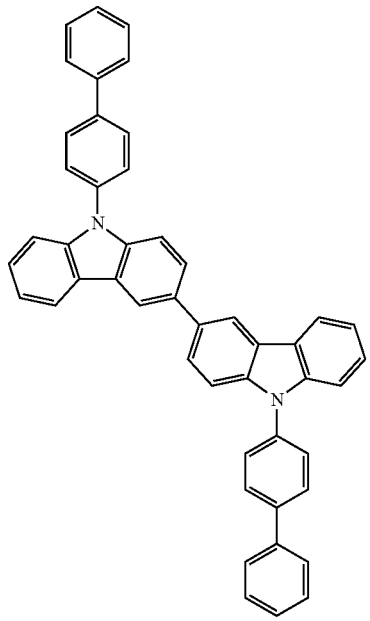
[E-100]
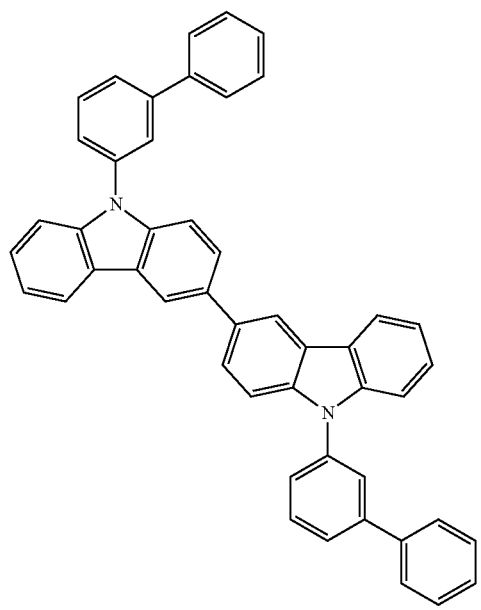
[E-101]
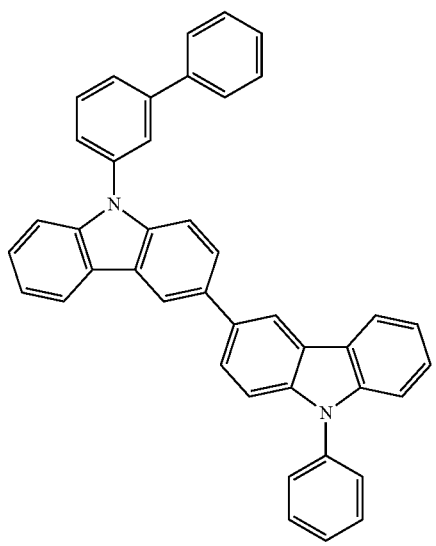

-continued
[E-102]
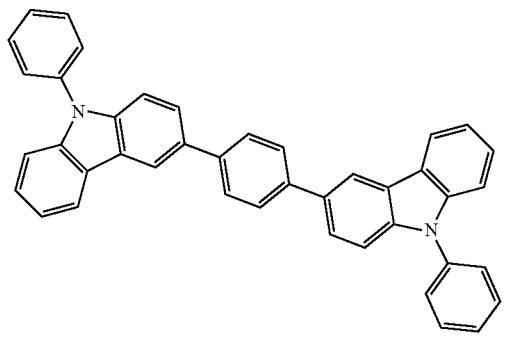
[E-103]
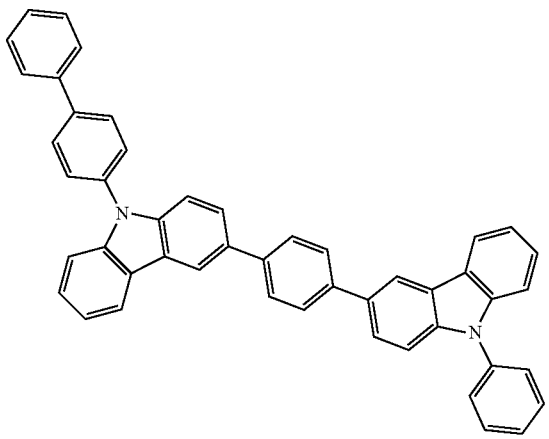
[E-104]
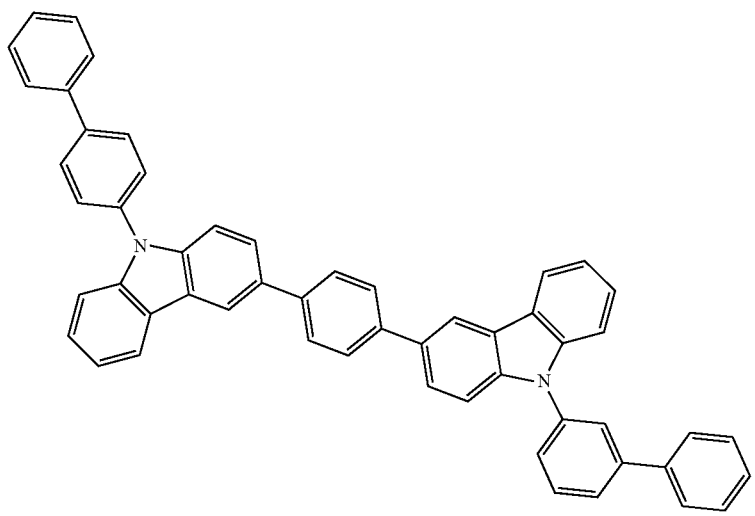
[E-105]
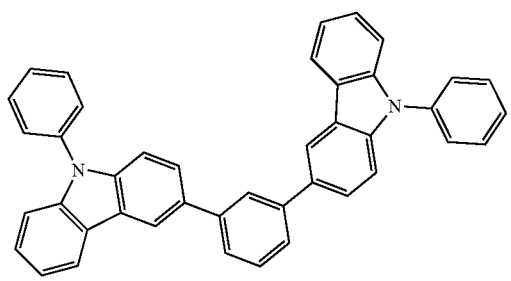
[E-106]
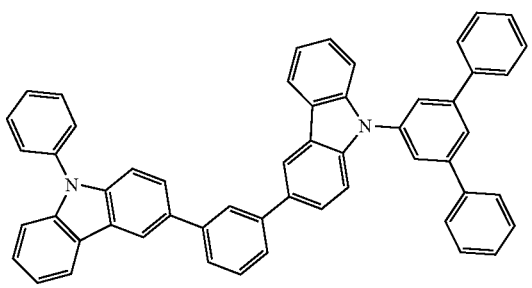

-continued
[E-107]
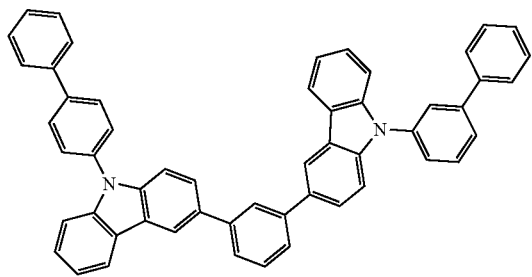
[E-108]
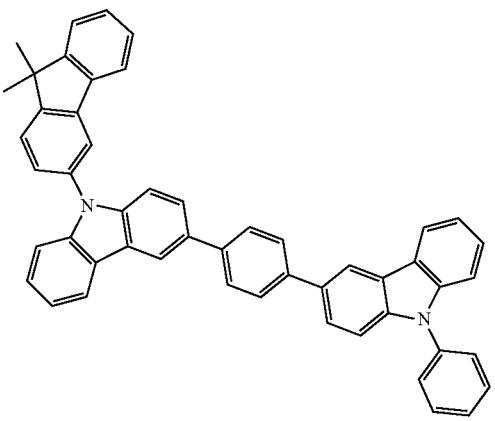
[E-109]
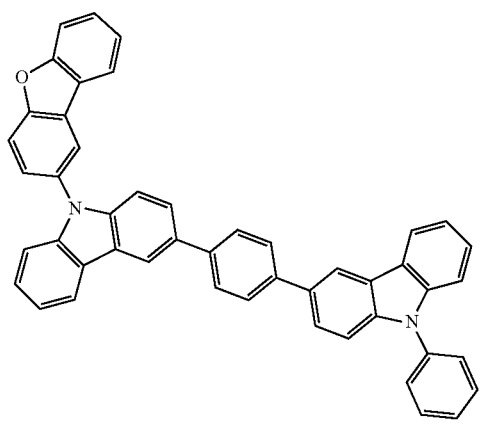
[E-110]
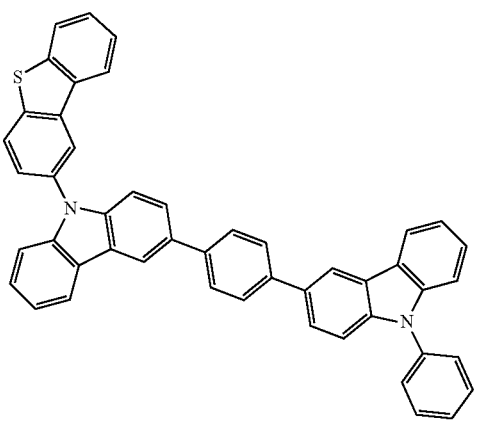
[E-111]
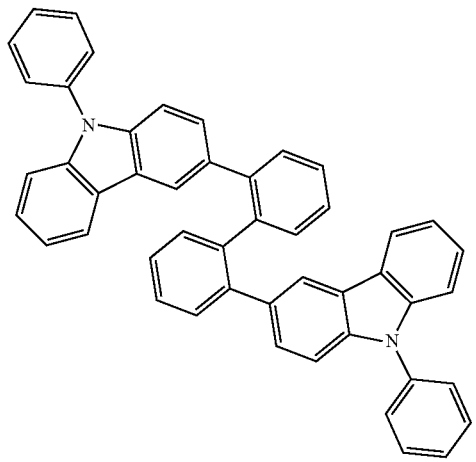
[E-112]
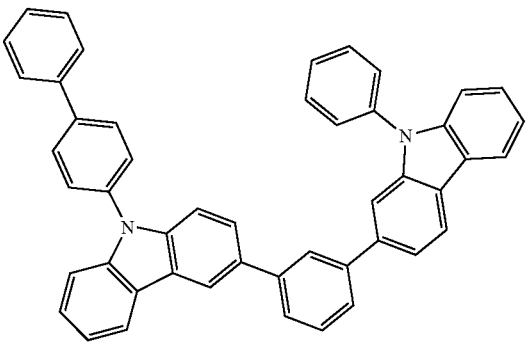

[E-113]
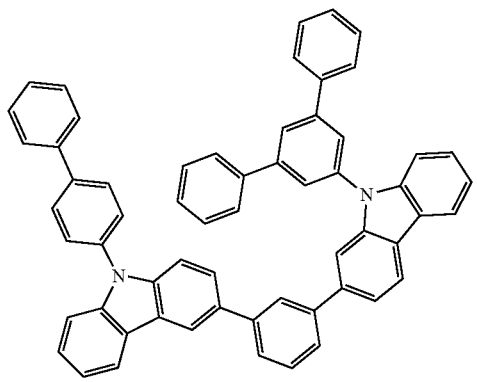
[E-114]
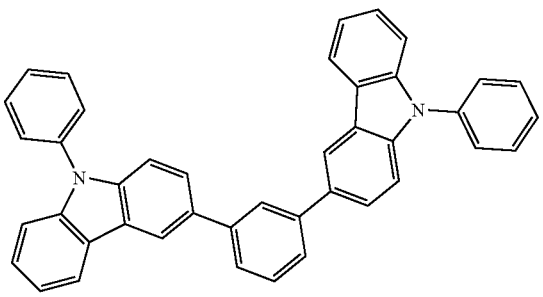
[E-115]
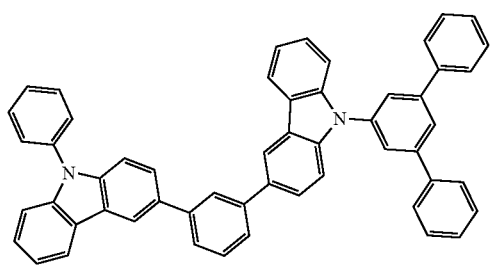
[E-116]
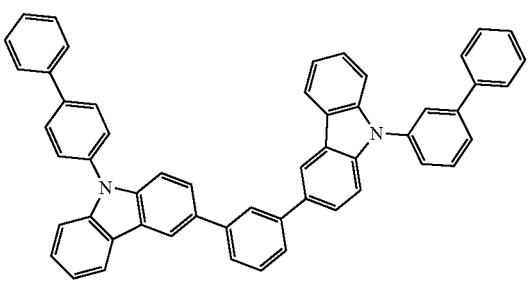
[E-117]
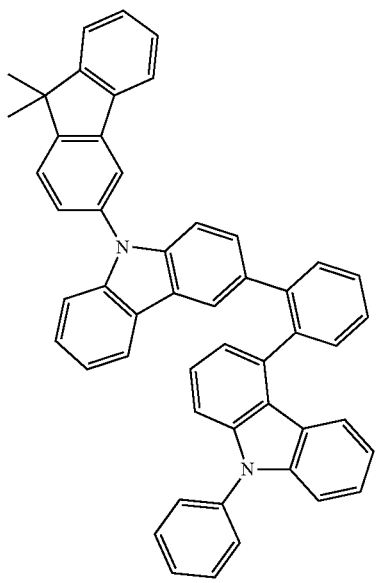
[E-118]
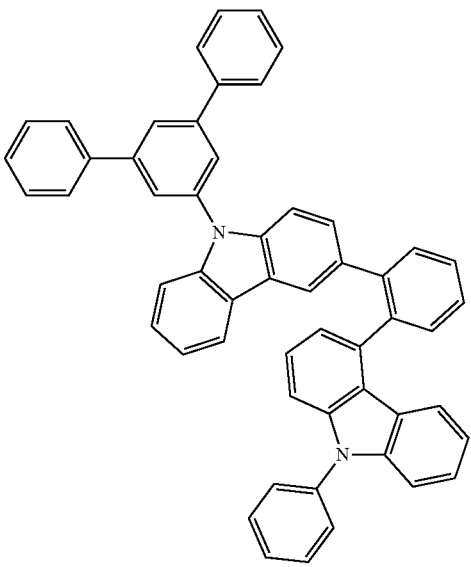

-continued
[E-119]
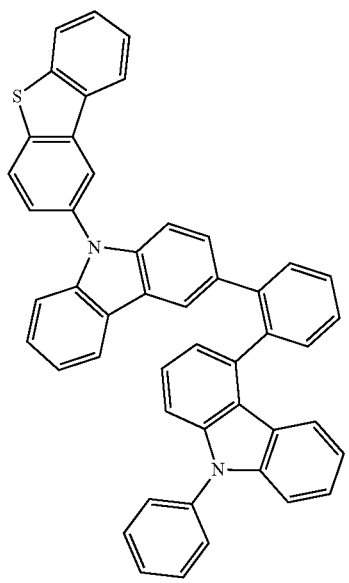
[E-120]
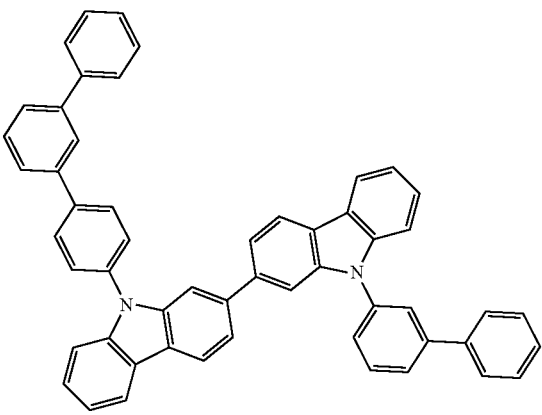
[E-121]
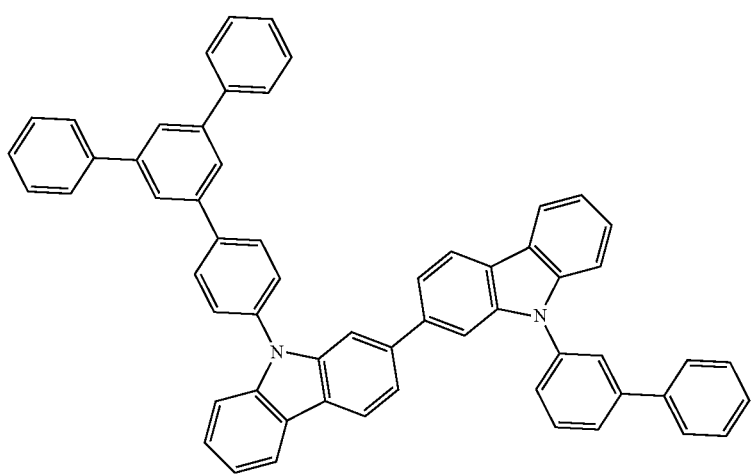

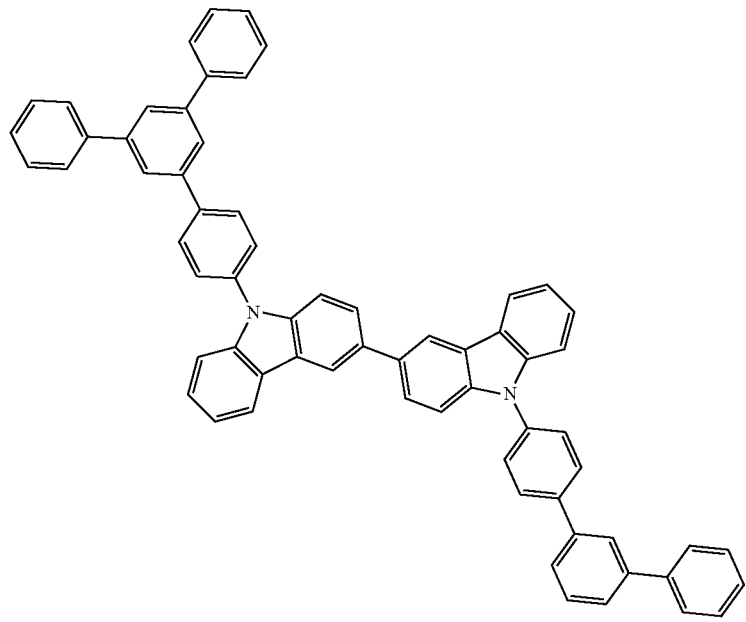
[E-122]
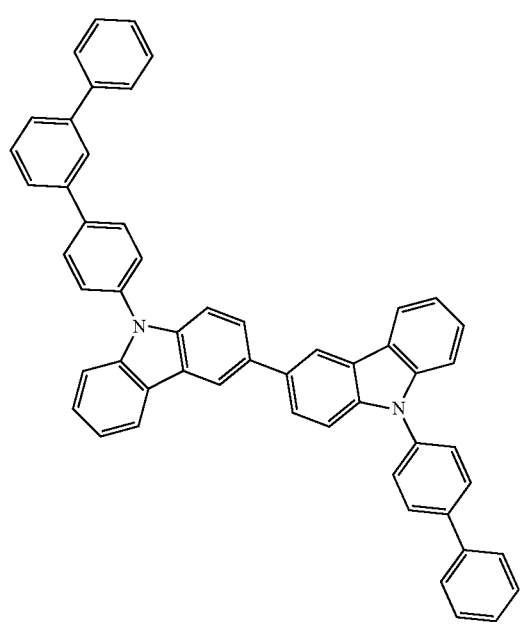
[E-123]

[E-124]
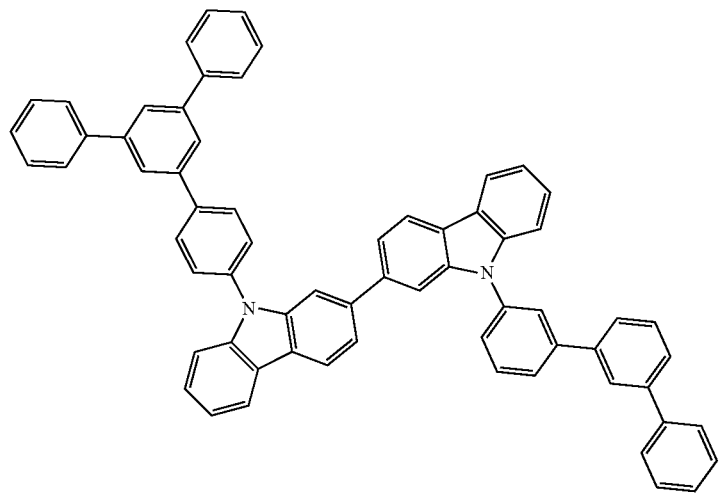
[E-125]
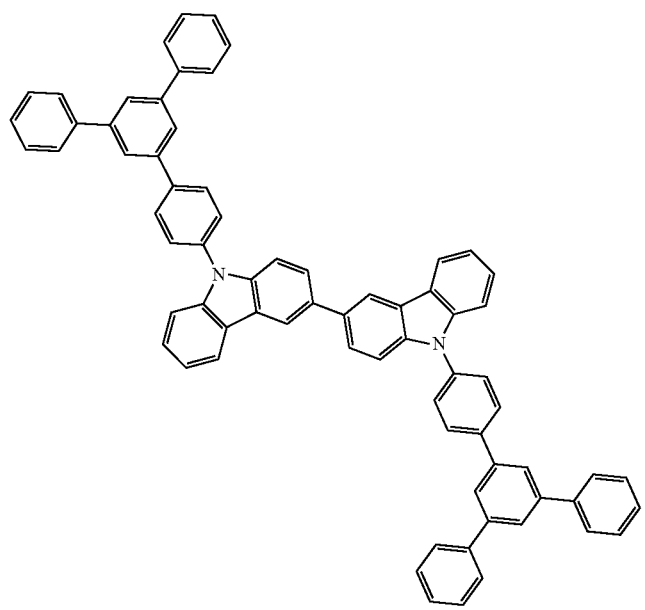
[E-126]
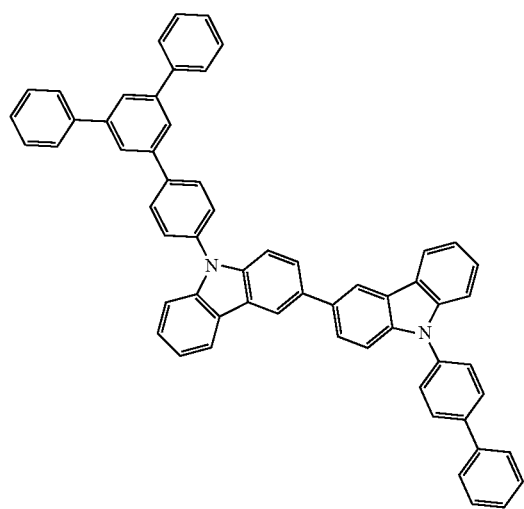
[E-127]
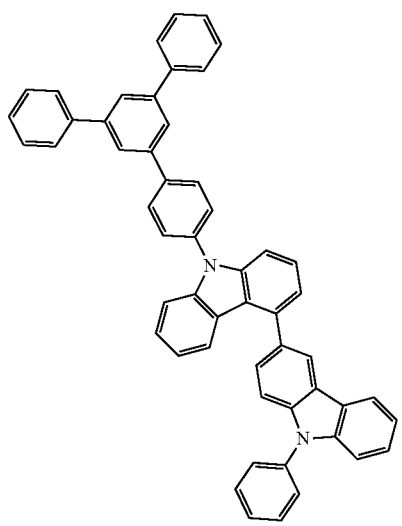

-continued
[E-128]
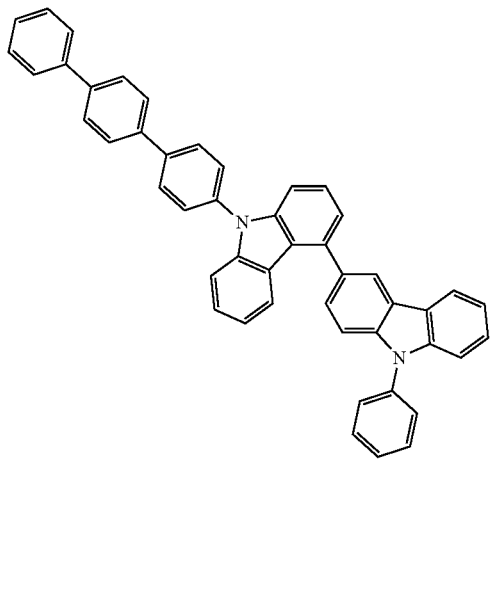
[E-129]
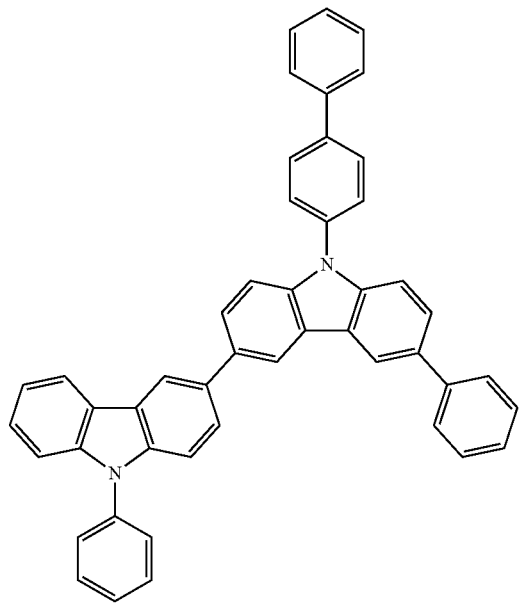
[E-130]
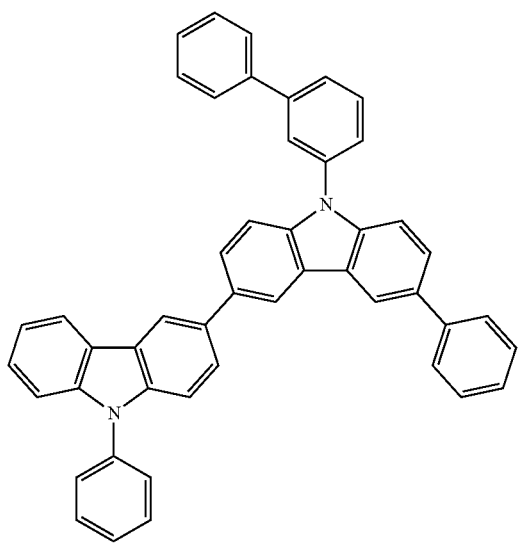
[E-131]
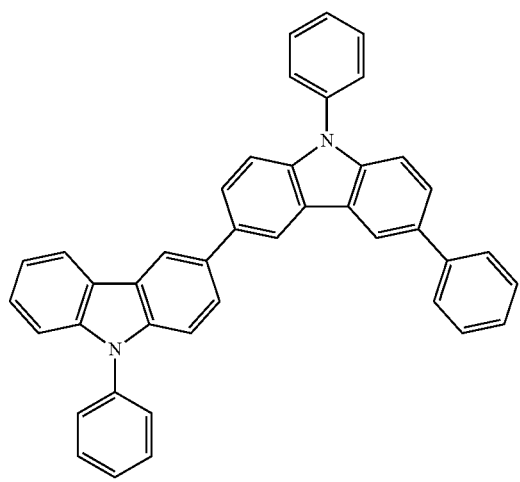

-continued
[E-132]
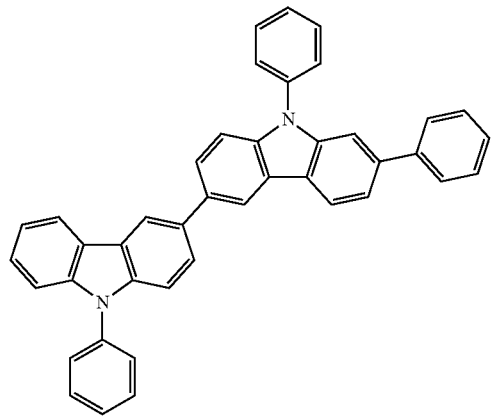
[E-133]
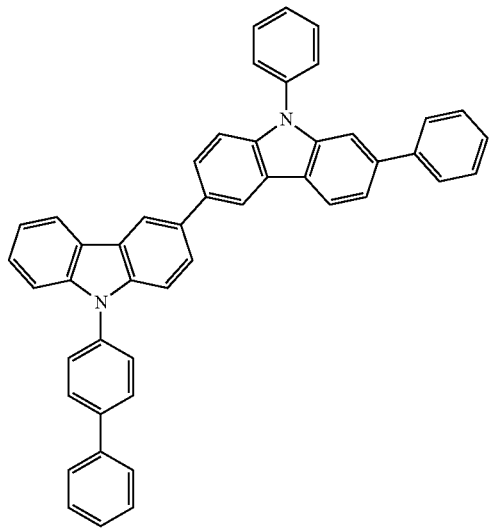
[E-134]
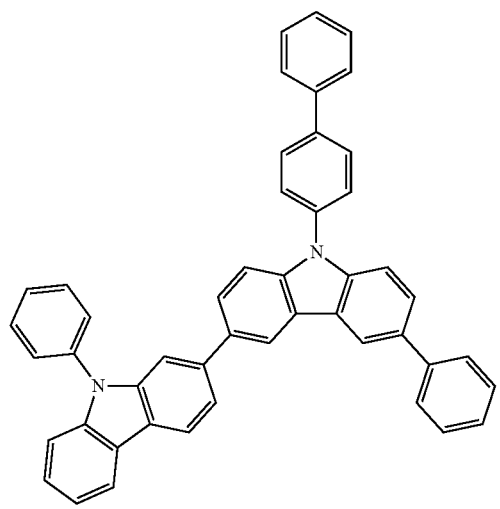
[E-135]
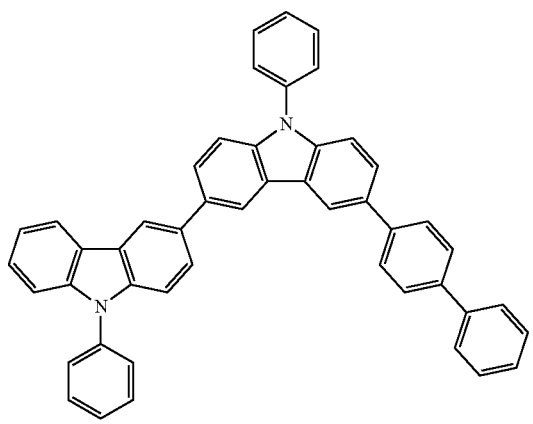
[E-136]
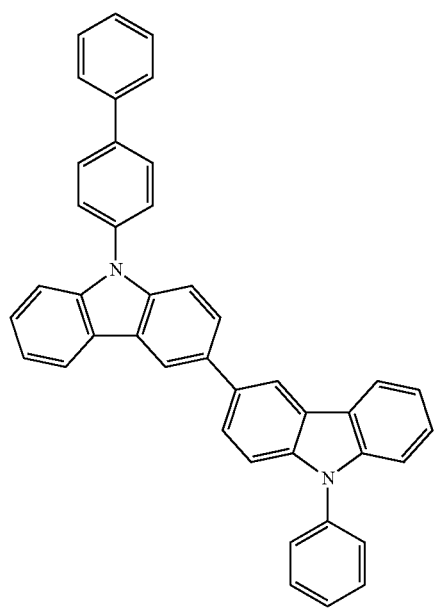
[E-137]
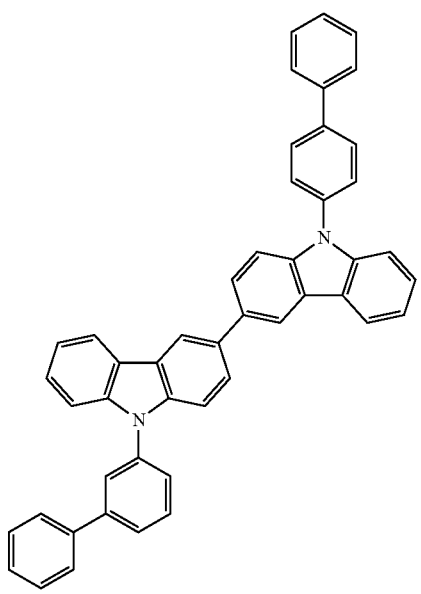

-continued

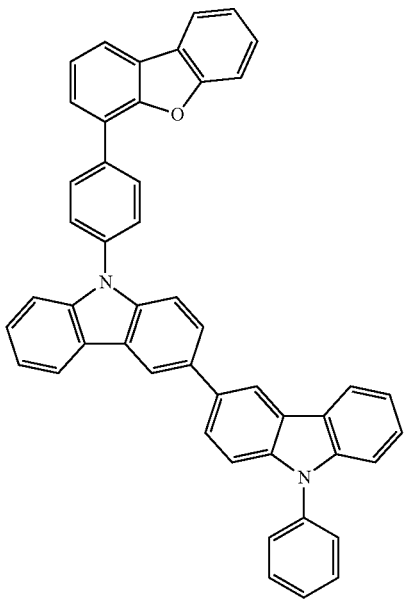
[E-138]

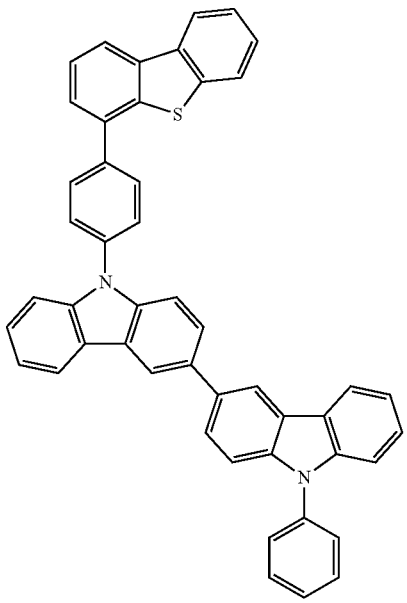
[E-139]

The above compound for an organic optoelectronic device and the second compound may variously be combined to prepare various compositions.

A composition according to an example embodiment of the present invention may include a compound represented by Chemical Formula 1-I, Chemical Formula 1-II, Chemical Formula 1-IV, or Chemical Formula 1-VI as a first host and a compound represented by Chemical Formula C-8 or Chemical Formula C-17 of Group I as a second host.

A composition according to an example embodiment of the present invention may include a compound represented by Chemical Formula 1-1, or Chemical Formula 1-2 as a first host and a compound represented by Chemical Formula C-8 or Chemical Formula C-17 of Group I as a second host.

For example, *-$L^1$-$Z^1$ and *-$L^2$-$Z^2$ of Chemical Formula 2 may be selected from B-1, B-2, B-3, B-16, and B-17 of Group II.

The second compound for an organic optoelectronic device is used with the first compound for an organic optoelectronic device in the light emitting layer and increases charge mobility and stability, and thereby luminous efficiency and life-span characteristics may be improved. In addition, a ratio of the second compound for an organic optoelectronic device and the first compound for an organic optoelectronic device may be adjusted and thereby charge mobility may be controlled.

For example, they may be included in a weight ratio of about 1:9 to 9:1, specifically in a weight ratio of 2:8 to 8:2, 3:7 to 7:3, 4:6 to 6:4, or 5:5, and for example the first compound for an organic optoelectronic device and the second compound for an organic optoelectronic device may be included at 3:7. Within the ranges, efficiency and life-span may be simultaneously improved.

The composition may further include one or more organic compounds in addition to the first compound for an organic optoelectronic device and the second compound for an organic optoelectronic device.

The composition for an organic optoelectronic device may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$L_2MX$         [Chemical Formula Z]

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

Hereinafter, an organic optoelectronic device including the compound for an organic optoelectronic device or the composition for an organic optoelectronic device is described.

An organic optoelectronic device according to another embodiment includes an anode and a cathode facing each other and at least one organic layer disposed between the anode and the cathode, wherein the organic layer includes the compound for an organic optoelectronic device or the composition for an organic optoelectronic device.

For example, the organic layer may include a light emitting layer and the light emitting layer may include the compound for an organic optoelectronic device or the composition for an organic optoelectronic device of the present invention.

Specifically, the compound for an organic optoelectronic device or the composition for an organic optoelectronic device may be included as a host, for example a green host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectronic device or the composition for an organic optoelectronic device.

The auxiliary layer may further include an electron transport auxiliary layer that is adjacent to the light emitting layer and the electron transport auxiliary layer may include the compound for an organic optoelectronic device or the composition for an organic optoelectronic device.

In an example embodiment of the present invention, the compound for an organic optoelectronic device included in the electron transport auxiliary layer may be represented by Chemical Formula 1-VI.

In another example embodiment of the present invention, the compound for an organic optoelectronic device included in the electron transport auxiliary layer may be represented by Chemical Formula 1-1 or Chemical Formula 1-2.

The organic optoelectronic device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectronic device is described referring to drawings.

FIGS. 1 and 2 are cross-sectional views of an organic light emitting diode according to an embodiment.

Referring to FIG. 1, an organic light emitting diode 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto. The cathode 110 may be made of a conductor having a small work function to help electron injection, and may be for example made of a metal, a metal oxide and/or a conductive polymer. The cathode 110 may be for example a metal or an alloy thereof such as magnesium, calcium, sodium, potassium, titanium, indium, yttrium, lithium, gadolinium, aluminum, silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes a light emitting layer 130 including the compound for an organic optoelectronic device or the composition for an organic optoelectronic device.

FIG. 2 is a cross-sectional view showing an organic light emitting diode according to another embodiment.

Referring to FIG. 2, an organic light emitting diode 200 further include a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for an organic optoelectronic device or the composition for an organic optoelectronic device of the present invention may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there in no particular comment or were synthesized by known methods.

(Preparation of Compound for Organic Optoelectronic Device)

The compound as one specific examples of the present invention was synthesized through the following steps.

(First Compound for Organic Optoelectronic Device)

Synthesis Example 1: Synthesis of Compound A-1

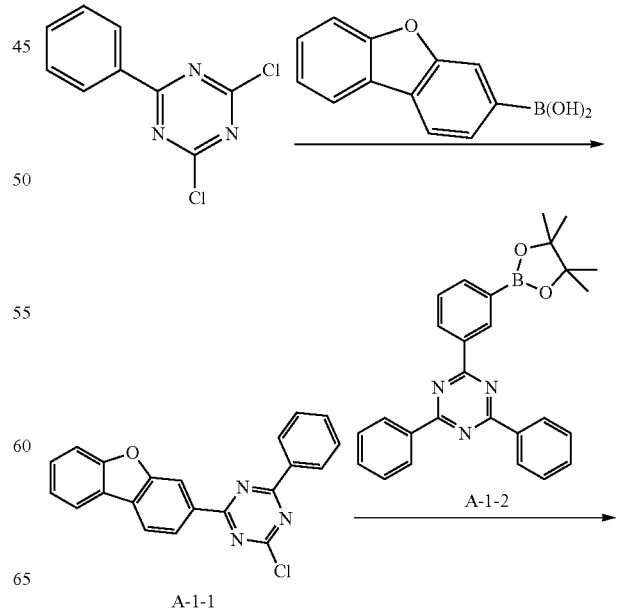

-continued

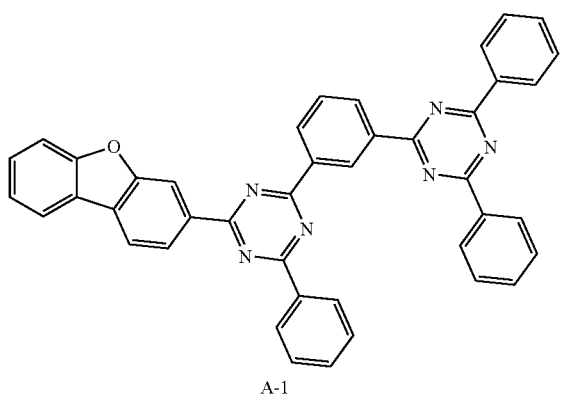

A-1

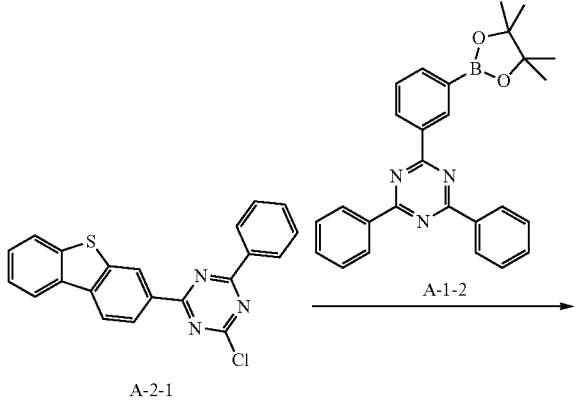

A-2-1

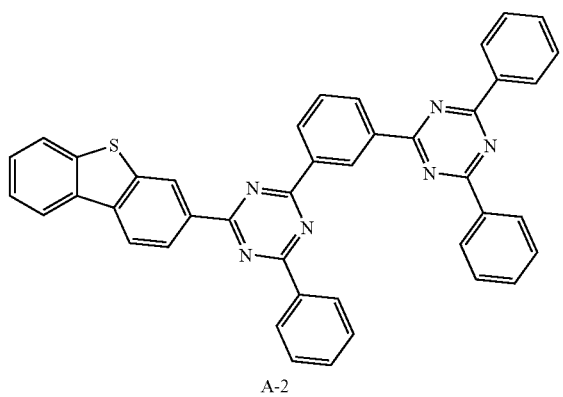

A-2 a) Synthesis of Intermediate A-1-1

22.6 g (100 mmol) of 2,4-dichloro-6-phenyltriazine was added to 100 mL of tetrahydrofuran, 100 mL of toluene, and 100 mL of distilled water in a 500 mL round-bottomed flask, 0.9 equivalents of dibenzofuran-3-boronic acid, 0.03 equivalents of tetrakistriphenylphosphine palladium, 2 equivalents of potassium carbonate were added thereto, and the mixture was heated and refluxed under a nitrogen atmosphere. The reaction solution was cooled down after 6 hours, an aqueous layer was removed, and an organic layer was dried under a reduced pressure. An obtained solid was washed with water and hexane, the solid was recrystallized with 200 mL of toluene to obtain 21.4 g (60% yield) of Intermediate A-1-1.

b) Synthesis of Compound A-1

20 g (55.9 mmol) of synthesized Intermediate A-1-1 was added to 200 mL of tetrahydrofuran and 100 mL of distilled water in a 500 mL round-bottomed flask, 1.1 equivalents of a triazine boronic acid pinacolester compound A-1-2, 0.03 equivalent of tetrakistriphenylphosphine palladium, and 2 equivalents of potassium carbonate were added thereto, and the mixture was heated and refluxed under a nitrogen atmosphere. The reaction solution was cooled down after 18 hours, and precipitated solid was filtered and washed with 500 mL of water. The solid was recrystallized with 500 mL of monochlorobenzene to obtain 26 g of Compound A-1.

LC/MS calculated for: C42H26N6O Exact Mass: 630.2168 found for: 631.22 [M+H]

Synthesis Example 2: Synthesis of Compound A-2

[Reaction Scheme 2]

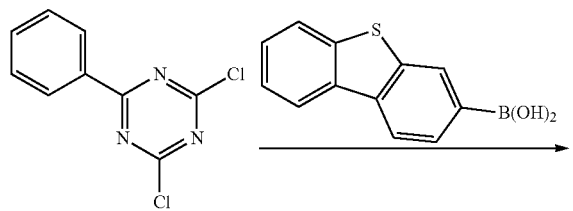

a) Synthesis of Intermediate A-2-1

Intermediate A-2-1 was synthesized according to the same method as a) of Synthesis Example 1 except for using dibenzothiophene 3-boronic acid instead of dibenzofuran 3-boronic acid.

b) Synthesis of Compound A-2

Compound A-2 was synthesized according to the same method as b) of Synthesis Example 1 except for using Intermediate A-2-1 and 1.1 equivalents of Intermediate A-1-2.

LC/MS calculated for: C42H26N6S Exact Mass: 646.1940 found for: 647.20 [M+H]

Synthesis Example 3: Synthesis of Compound A-3

[Reaction Scheme 3]

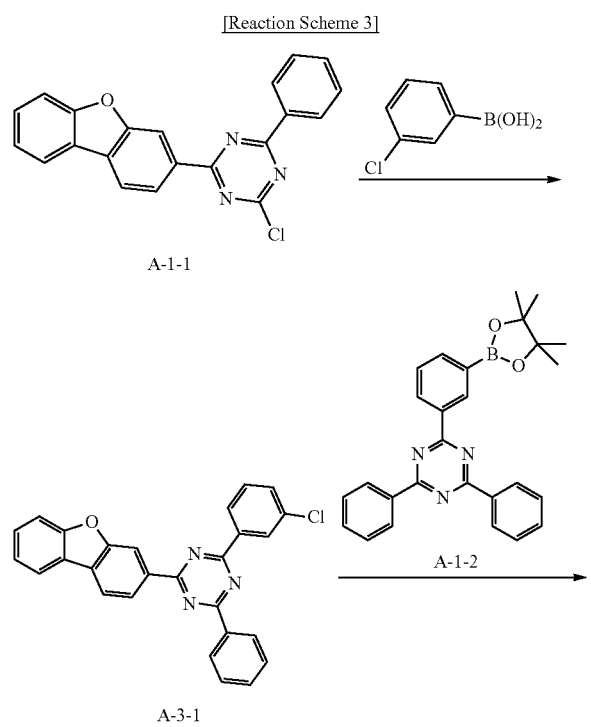

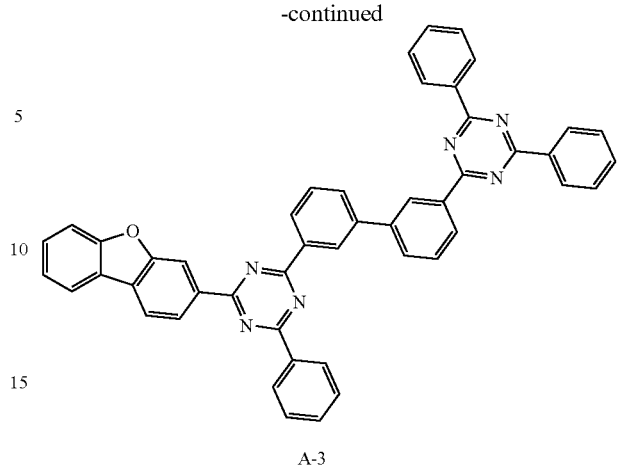

a) Synthesis of Intermediate A-3-1

Intermediate A-3-1 was synthesized according to the same method as b) of Synthesis Example 1 except for using 1 equivalent of Intermediate A-1-1 and 1.1 equivalents of 3-chlorophenylboronic acid.

b) Synthesis of Compound A-3

Compound A-3 was synthesized according to the same method as b) of Synthesis Example 1 except for using Intermediate A-3-1 and 1.1 equivalents of Intermediate A-1-2.

LC/MS calculated for: C48H30N6S Exact Mass: 706.2481 found for: 707.25 [M+H]

Synthesis Example 4: Synthesis of Compound A-10

[Reaction Scheme 4]

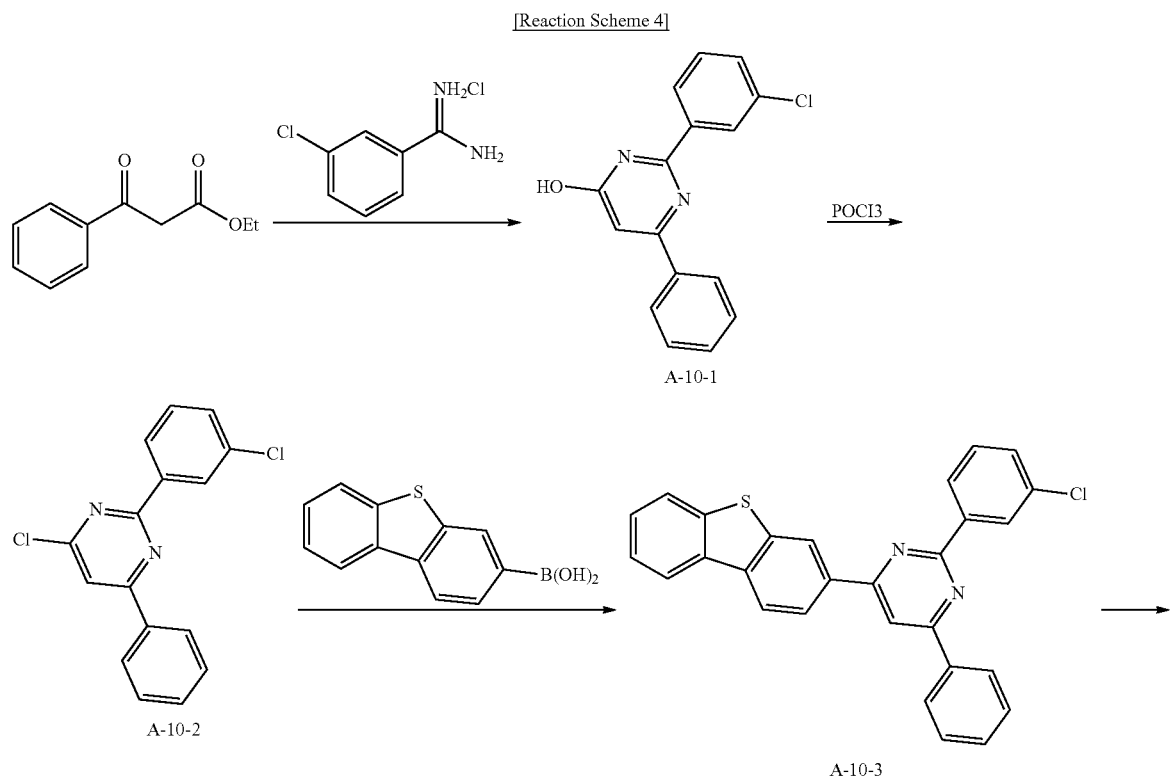

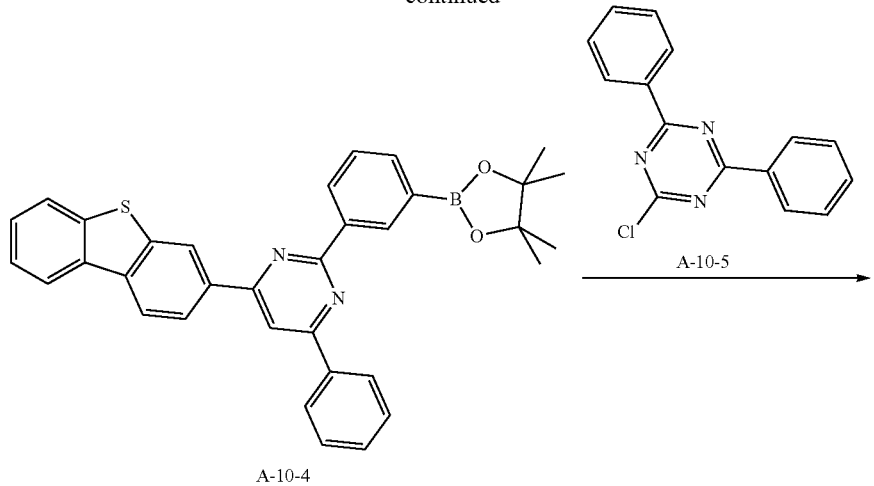

A-10-4

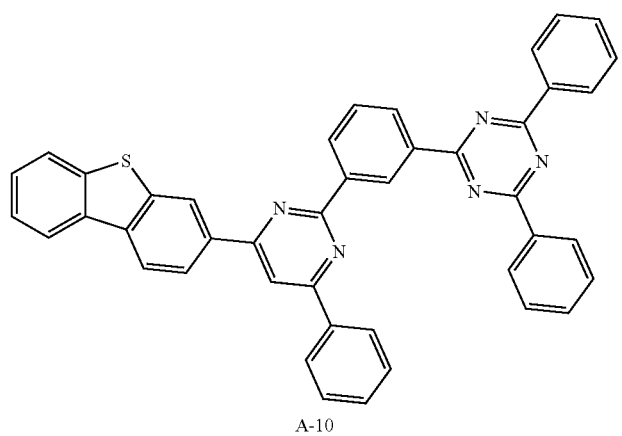

A-10 a) Synthesis of Intermediate A-10-1

1 equivalent of ethylbenzoylacetate and 1 equivalent of 3-chlorophenylamidine-hydrochloride were heated and refluxed with 1 equivalent sodium methoxide in methanol (0.5M). pH of a product was controlled to be about 6 and a obtained solid filtered and washed with a small amount of water. The obtained solid was dried to synthesize Intermediate A-10-1 at a yield of about 50%.

b) Synthesis of Intermediate A-10-2

1 equivalent of Intermediate A-10-1 was reacted for 6 hours by heating it up to 90° C. using 7 equivalents of phosphorus oxychloride. The product was cooled down and was poured in an ice bath to terminate a reaction. The obtained solid was dissolved in dichloromethane and an organic layer was separated by extraction, and was dried under a reduced pressure to synthesize Intermediate A-10-2.

c) Synthesis of Intermediate A-10-3

Intermediate A-10-3 was synthesized according to the same method as b) of Synthesis Example 1 except for using 1 equivalent of Intermediate A-10-2 and 1.1 equivalents of dibenzothiophene-3-boronic acid.

d) Synthesis of Intermediate A-10-4

10 g (20.45 mmol) of The synthesized intermediate A-10-3 was put in 100 mL of DMF in 500 mL round-bottomed flask, 0.05 equivalents of dichlorodiphenyl phosphinoferrocene palladium, 1.2 equivalents of bispinacolato diboron, and 2 equivalents of potassium acetate were added thereto, and the mixture was heated and refluxed under a nitrogen atmosphere for 18 hours. The reaction solution was cooled down and was dripped in 1 L of water to capture a solid. The obtained solid was dissolved in a boiling toluene, treated with activated carbon, and filtered with a silica gel and a filtrate was concentrated. The concentrated solid was stirred with a small amount of hexane and a solid is filtered to obtain Intermediate A-10-4 at a yield of 80%.

e) Synthesis of Compound A-10

Compound A-10 was synthesized according to the same method as b) of Synthesis Example 1 except for using 1 equivalent of Intermediate A-10-4 and 1.1 equivalents of 2-chloro-4,6-diphenyl-1,3,5-triazine A-10-5.

LC/MS calculated for: C43H27N5S Exact Mass: 645.1987 found for: 646.20 [M+H]

Synthesis Example 5: Synthesis of Compound A-49
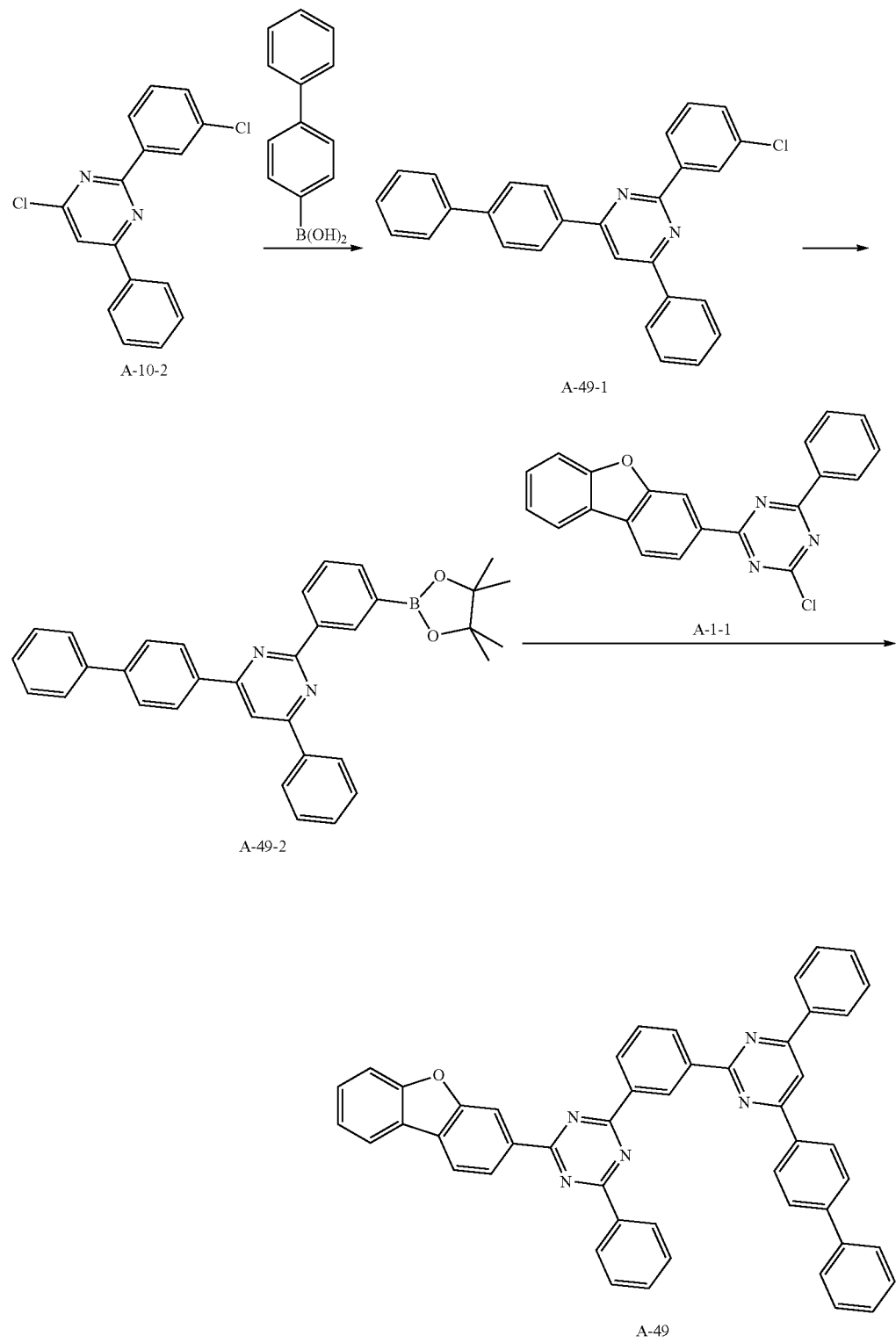

a) Synthesis of Intermediate A-49-1

Intermediate A-49-1 was synthesized according to the same method as b) of Synthesis Example 1 except for using 1 equivalent of Intermediate A-10-2 and 1.1 equivalents of 4-phenylbenzene-boronic acid.

b) Synthesis of Intermediate A-49-2

Intermediate A-49-2 was synthesized according to the same method as d) of Synthesis Example 4 using 1 equivalent of Intermediate A-49-1 c) Synthesis of Compound A-49

Compound A-49 was synthesized according to the same method as b) of Synthesis Example 1 except for using 1 equivalent of Intermediate A-49-2 and 1.1 equivalents of Intermediate A-1-1.

LC/MS calculated for: C49H31N50 Exact Mass: 705.2529 found for: 706.26 [M+H]

Synthesis Example 6: Synthesis of Compound A-51

[Reaction Scheme 6]

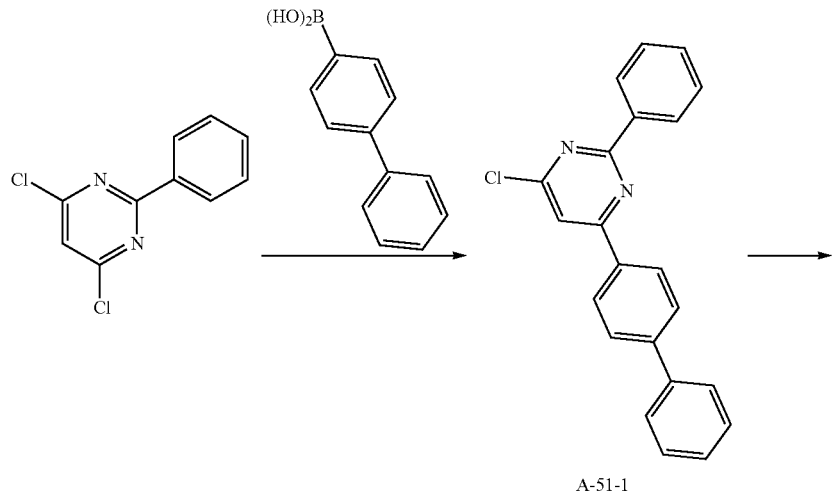

A-51-1

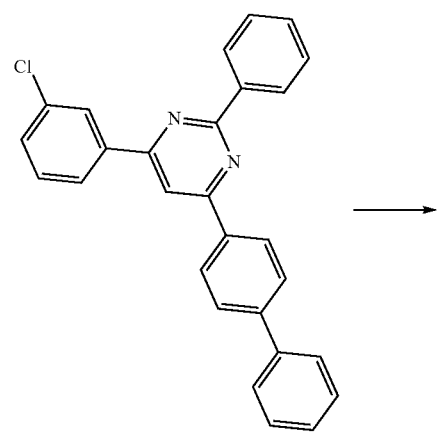

A-51-2

-continued

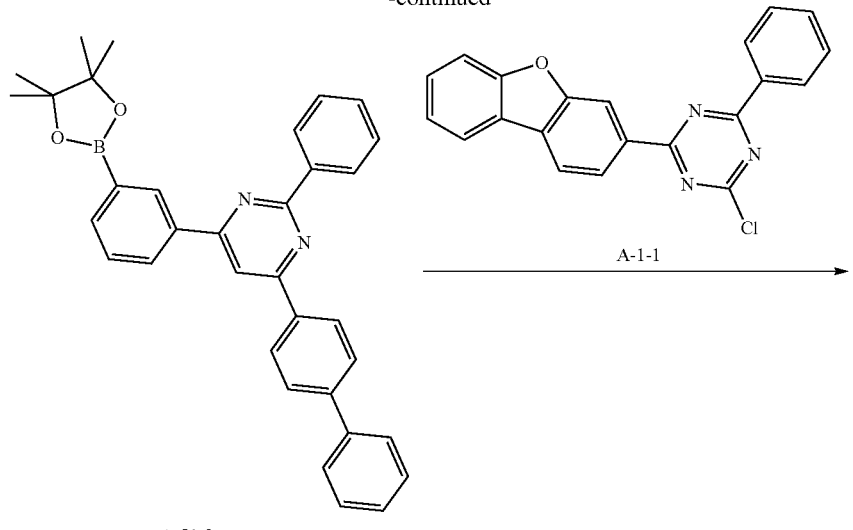

A-51-3     A-1-1

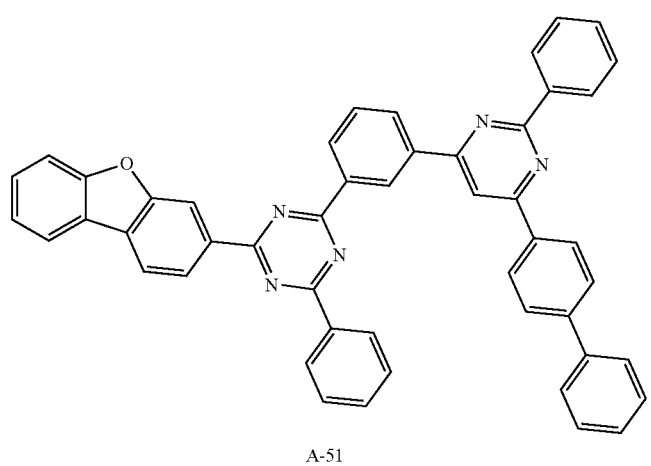

A-51 a) Synthesis of Intermediate A-51-1

Intermediate A-51-1 was synthesized according to the same method as b) of Synthesis Example 1 except for using 1 equivalent of Intermediate, 3,5-dichloro-1-phenyl-2,6-pyrimidine and 1.1 equivalents of 4-phenylbenzene-boronic acid.

b) Synthesis of Intermediate A-51-2

Intermediate A-51-2 was synthesized according to the same method as b) of Synthesis Example 1 except for using 1 equivalent of Intermediate A-51-1 and 1.1 equivalents of 3-chlorophenylboronic acid.

c) Synthesis of Intermediate A-51-3

Intermediate A-51-3 was synthesized according to the same method as d) of Synthesis Example 4 using 1 equivalent of Intermediate A-51-2.

d) Synthesis of Compound A-51

Compound A-51 was synthesized according to the same method as b) of Synthesis Example 1 except for using 1 equivalent of Intermediate A-51-3 and 1.1 equivalents of Intermediate A-1-1.

LC/MS calculated for: C49H31N50 Exact Mass: 705.2529 found for: 706.26 [M+H]

(Synthesis of Second Compound for an Organic Optoelectronic Device)

Synthesis Example 7: Synthesis of Compound E-138

[Reaction Scheme 7]

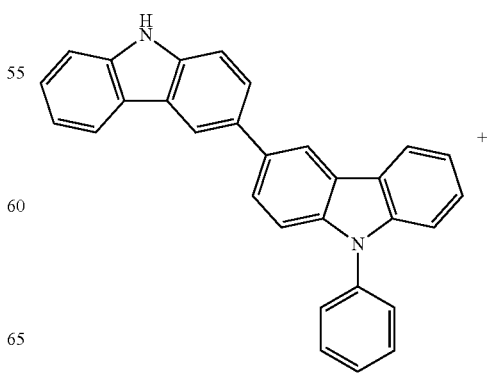

+

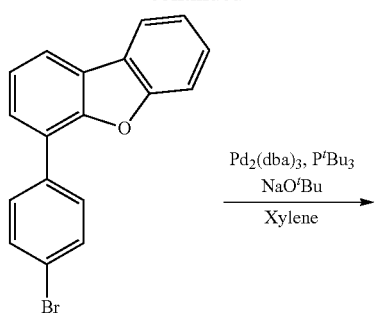

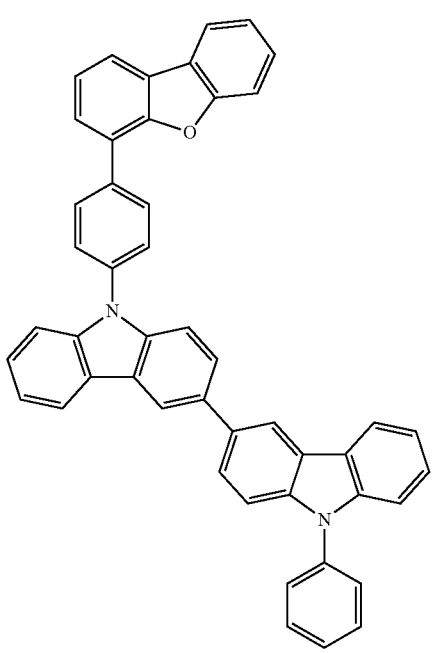

Compound E-138 was synthesized using 1 eq of N-phenyl-3,3-bicarbazole and 1 eq of 4-(4-bromophenyl)dibenzo[b,d]furan.

calcd. C48H30N2O: C, 88.59; H, 4.65; N, 4.30; O, 2.46; found : C, 88.56; H, 4.62; N, 4.20; O, 2.43

Comparative Synthesis Example 1: Synthesis of Comparative Compound 1

[Reaction Scheme 8]

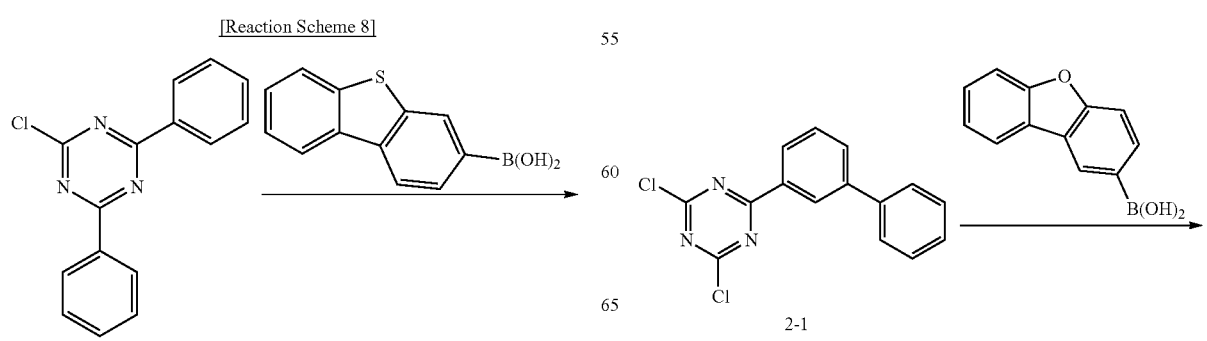

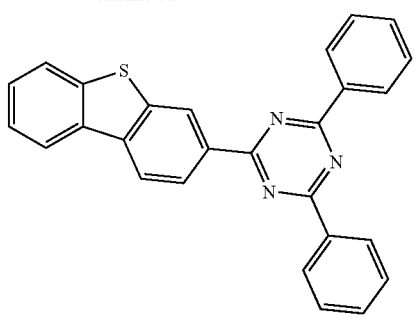

Comparative Example 1 a) Synthesis of Comparative Compound 1

Comparative Compound 1 was synthesized according to the same method as b) of Synthesis Example 1 except for using 2-chloro-4,6-diphenyltriazine and dibenzothiophene-3-boronic acid.

LC/MS calculated for: C27H17N3S Exact Mass: 415.1143 found for 416.11 [M+H]

Comparative Synthesis Example 2: Synthesis of Comparative Compound 2

[Reaction Scheme 9]

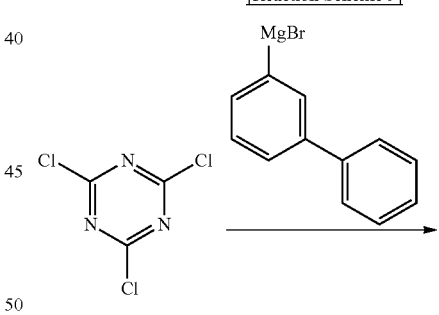

2-1

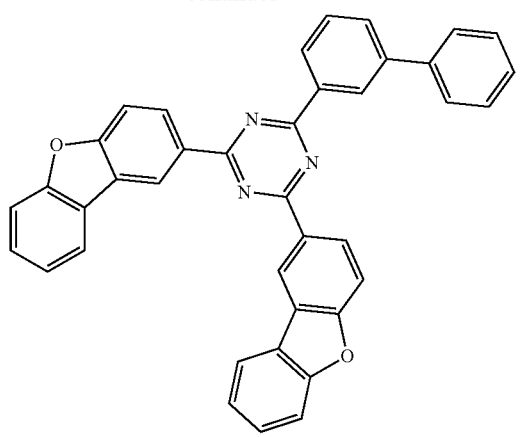

Comparative Example 2

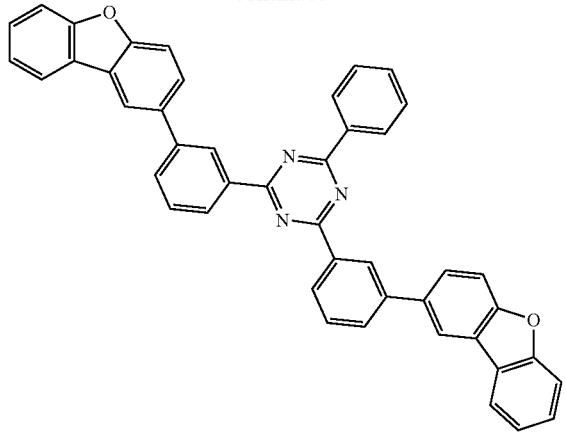

Comparative Example 3 a) Synthesis of Intermediate 2-1

15 g (81.34 mmol) of cyanuric chloride was dissolved in 200 mL of anhydrous tetrahydrofuran in a 500 mL round-bottomed flask, 1 equivalent of 3-biphenyl magnesium bromide solution (0.5 M tetrahydrofuran) was added in a dropwise fashion at 0° C. under a nitrogen atmosphere and the temperature was slowly increased up to room temperature. The mixture was stirred at room temperature for 1 hour and the reaction solution was put in 500 mL of ice water to separate layers. An organic layer was separated, treated with anhydrous magnesium sulfate and concentrated. The concentrated residue was recrystallized with tetrahydrofuran and methanol to obtain 17.2 g of Intermediate 2-1.

b) Synthesis of Comparative Compound 2

Comparative Compound 2 was synthesized according to the same method as b) of Synthesis Example 1 except for using Intermediate 2-1 and dibenzofuran-2-boronic acid.

LC/MS calculated for: C39H23N3O Exact Mass: 565.1790 found for 566.18 [M+H]

Comparative Synthesis Example 3: Synthesis of Comparative Compound 3 a) Synthesis of Comparative Compound 3

Comparative Compound 3 was synthesized according to the same method as b) of Synthesis Example 1 except for using 2,4-dichloro-6-phenyl-1,3,5-triazine and dibenzofuran-2-yl-3-phenylboronic acid (3-1).

LC/MS calculated for: C39H23N3O Exact Mass: 565.1790 found for 566.18 [M+H]

Comparative Synthesis Example 4: Synthesis of Comparative Compound 4

[Reaction Scheme 11]

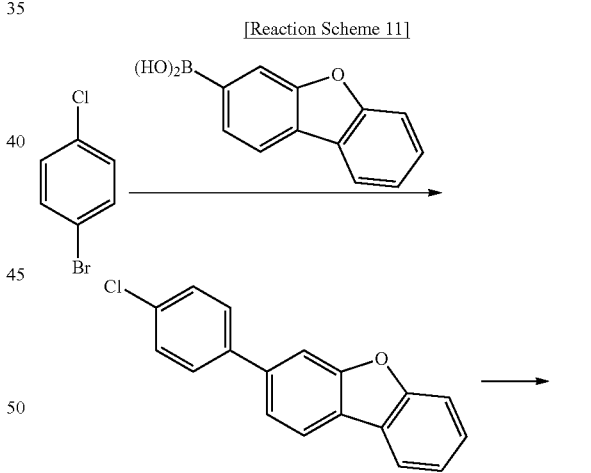

4-1

[Reaction Scheme 10]

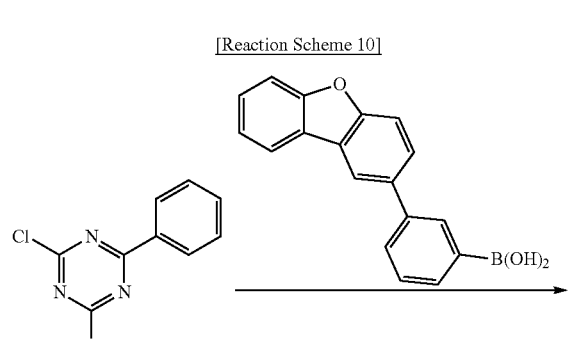

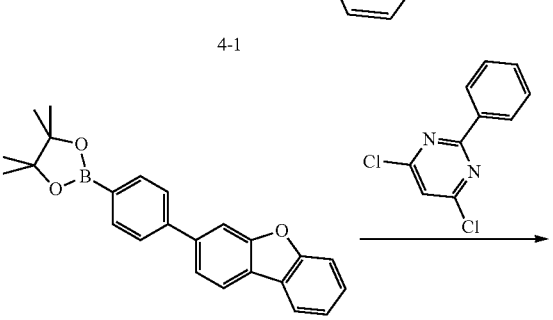

4-2

-continued

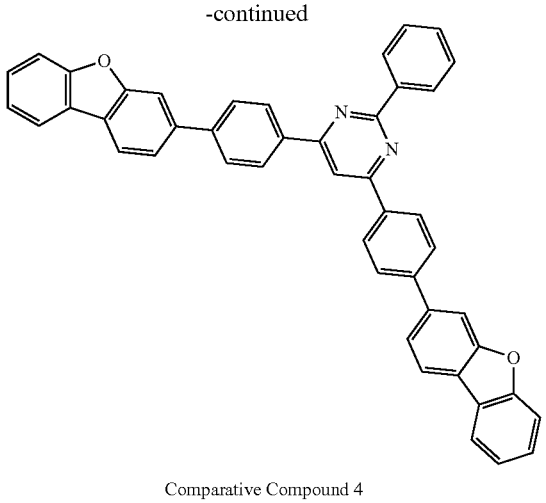

Comparative Compound 4 a) Synthesis of Intermediate 4-1

Intermediate 4-1 was synthesized according to the same method as b) of Synthesis Example 1 except for using 1-bromo-4-chlorobenzene and dibenzofuran-3-boronic acid.

b) Synthesis of Intermediate 4-2

Intermediate 4-2 was synthesized by performing a reaction under the same condition as d) of Synthesis Example 4 using Intermediate 4-1.

c) Synthesis of Comparative Compound 4

Comparative Compound 4 was synthesized according to the same method as b) of Synthesis Example 1 except for using Intermediate 4-2 and 4,6-dichloro-2-phenyl-1,3-pyrimidine.

LC/MS calculated for: C46H28N2O2 Exact Mass: 640.2151 found for 641.22 [M+H]

(Manufacture of Organic Light Emitting Diode)

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 400 Å-thick light emitting layer was formed on the hole transport layer by vacuum-depositing Compound A-1 of Synthesis Example 1 and Compound E-130 simultaneously as hosts and 10 wt % of tris(2-phenylpyridine)iridium (III) [Ir(ppy)$_3$] as a dopant. Herein, Compound A-1 and Compound E-130 were used in a 7:3 ratio and their ratios of the following examples were separately described. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically a structure of ITO/Compound A 700 Å/Compound B 50 Å/Compound C 1020 Å/EML[Compound A-1:E-130:Ir (ppy)$_3$=27 wt %: 63 wt %10 wt %] 400 Å/Compound D: Liq 300 Å/Liq 15 Å/Al 1200 Å.

Compound A: N4,N4'-diphenyl-N4,N4'-bis(9-phenyl-9H-carbazol-3-yl)biphenyl-4,4'-diamine, Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine, and Compound D: 8-(4-(4,6-di(naphthalen-2-yl)-1,3,5-triazin-2-yl)phenyl)quinolone.

Example 2 and Example 3

Diodes according to Example 2 and Example 3 were manufactured according to the same method as Example 1 by using Compound A-1 and Compound A-2 alone respectively as shown in Table 1.

Example 4 to Example 11

Diodes according to Example 4 to Example 11 were manufactured according to the same method as Example 1 by using the first host and the second host respectively as shown in Tables 2 and 3.

Comparative Example 1 and Comparative Example 2

Diodes according to Comparative Example 1 and Comparative Example 2 were manufactured according to the same method as Example 1 by using Comparative Compound 1 and Comparative Compound 2 alone respectively as shown in Table 1.

Comparative Example 3 to Comparative Example 6

Diodes according to Comparative Example 3 to Comparative Example 6 were manufactured according to the same method as Example 1 by using Comparative Compound 1 to Comparative Compound 4 respectively instead of Compound A-1 as shown in Tables 2 and 3.

Evaluation 1

Luminous efficiency and life-span characteristics of each of the organic light emitting diodes according to Examples 1 to 11 and Comparative Examples 1 to 6 were evaluated. Specific measurement methods are as follows, and the results are shown in Table 1 to Table 3.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

T97 life-spans of the organic light emitting diodes according to Examples 1 to 12 and Comparative Example 1 to Comparative Example 7 were measured as a time when their luminance decreased down to 90% relative to the initial luminance (cd/m$^2$) after emitting light with 5000 cd/m$^2$ as the initial luminance (cd/m$^2$) and measuring their luminance decrease depending on a time with a Polanonix life-span measurement system.

TABLE 1

Single Host Device

| | Host | Color | Efficiency Cd/A | Driving (Vd) |
|---|---|---|---|---|
| Example 2 | Compound A-1 | green | 42 | 3.5 |
| Example 3 | Compound A-2 | green | 39 | 3.5 |
| Comparative Example 1 | Comparative Compound 1 | green | 32 | 3.7 |
| Comparative Example 2 | Comparative Compound 2 | green | 28 | 4.0 |

Referring to Table 1, in a case of a single host, when comparing Example 2 and Example 3 with Comparative Examples 1 and 2, dimers may provide a lower driving voltage despite dibenzofuran linked with triazine at the same position No. 3.

TABLE 2

Mixed Host Device Effect - structure including a triazinyl group

| | First host | Second host | First host:Second host ratio | Color | Efficiency Cd/A | Life-span (T90) | Driving (Vd) |
|---|---|---|---|---|---|---|---|
| Example 1 | Compound A-1 | Compound E-130 | 3:7 | green | 52 | 550 | 3.6 |
| Example 4 | Compound A-1 | Compound E-99 | 3:7 | green | 51 | 600 | 3.4 |
| Example 5 | Compound A-1 | Compound E-137 | 3:7 | green | 51 | 650 | 3.6 |
| Example 6 | Compound A-1 | Compound E-138 | 3:7 | green | 52 | 570 | 3.7 |
| Example 7 | Compound A-2 | Compound E-137 | 3:7 | green | 50 | 470 | 3.7 |
| Example 8 | Compound A-3 | Compound E-137 | 3:7 | green | 50 | 640 | 3.7 |
| Comparative Example 3 | Comparative Compound 1 | Compound E-137 | 3:7 | green | 48 | 360 | 4.0 |
| Comparative Example 4 | Comparative Compound 2 | Compound E-137 | 3:7 | green | 46 | 240 | 4.4 |
| Comparative Example 5 | Comparative Compound 3 | Compound E-137 | 3:7 | green | 46 | 230 | 4.7 |

TABLE 3

Mixed Host Device Effect - structure including a pyrimidinyl group

| | First host | Second host | First host:Second host ratio | Color | Efficiency Cd/A | Life-span (T90) | Driving (Vd) |
|---|---|---|---|---|---|---|---|
| Example 9 | Compound A-10 | Compound E-137 | 3:7 | green | 52 | 590 | 3.6 |
| Example 10 | Compound A-49 | Compound E-137 | 3:7 | green | 51 | 530 | 3.6 |
| Example 11 | Compound A-51 | Compound E-137 | 3:7 | green | 50 | 510 | 3.7 |
| Comparative Example 6 | Comparative Compound 4 | Compound E-137 | 3:7 | green | 52 | 190 | 4.5 |

Referring to Tables 2 and 3, examples using the first host and the second host according to the present invention showed improved life-span and lowered driving compared with comparative example using a mixed host of the same second host or compounds of comparative examples when a linking position of dibenzofuran linked with triazine is No. 3 with a structural specialty and/or a dimer with another triazine is designed.

These effects were equally obtained in a pyrimidine core as well as in a triazine core. Accordingly, from the corresponding diode data, when dibenzofuran or dibenzothiophene is directly linked with a ET core group, life-spans of diodes of the corresponding materials are improved through effective SUMO expansion and ring fusion effects and a driving voltage may be lowered through a dimer structure.

Example 12 (Electron Transport Auxiliary Layer)

ITO (indium tin oxide) was coated to be 1500 Å thick on a glass substrate, and the coated glass was ultrasonic wave-washed with a distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. Then, a 200 Å-thick light emitting layer was formed thereon by vacuum-depositing BH113 and BD370 (Manufacturer: SFC Inc.) as a blue fluorescent luminescent host and a dopant in a dopant concentration of 5 wt %. On the light emitting layer, Compound A-1 was vacuum-deposited to form a 50 Å-thick electron transport auxiliary layer. On the electron transport auxiliary layer, a 300 Å-thick electron transport layer was formed by vacuum-depositing Compound D and Liq simultaneously in a weight ratio of 1:1, and on the electron transport layer, a cathode was formed by sequentially vacuum-depositing Liq to be 15 Å thick and Al to be 1200 Å thick, manufacturing an organic light emitting diode. The organic light emitting diode had a structure of 5 organic thin film layers and specifically ITO/Compound A 700 Å/Compound B 50 Å/Compound C (1020 Å)/EML [BH113:BD370=95:5(wt:wt)] 200 Å/Compound A-1 50 Å/Compound D:Liq 300 Å=1:1/Liq 15 Å/Al 1200 Å.

(Compounds A, B, C, and D are the same as compounds used in Example 1.)

Example 13 and Example 14

Each of organic light emitting diodes according to Example 13 and Example 14 were manufactured according to the same method as Example 12 except for using Compound A-2 and Compound A-3 respectively.

Comparative Example 7

An organic light emitting diode was manufactured according to the same method as Example 12 except for using Comparative Compound 1.

Evaluation 2

Current density change, luminance change, and luminous efficiency depending on a voltage of each organic light emitting diode according to Examples 12 to 14 and Comparative Example 7 were measured.

Specific measurement methods are the same as in Evaluation 1, a method of measuring life-span is as follows, and the results are shown in Table 4.

[Measurement of Life-Span]

T97 life-spans of the organic light emitting diodes according to Examples 12 to Example 14 and Comparative Example 7 were measured as a time when their luminance decreased down to 97% relative to the initial luminance (cd/m²) after emitting light with 750 cd/m² as the initial luminance (cd/m²) and measuring their luminance decrease depending on a time with a Polanonix life-span measurement system.

TABLE 4

| Devices | Electron transport auxiliary layer | Luminous efficiency (cd/A) | Color coordinate (x, y) | T97(h) @750 nit |
|---|---|---|---|---|
| Example 12 | Compound A-1 | 6.2 | (0.132, 0.149) | 95 |
| Example 13 | Compound A-2 | 6.1 | (0.131, 0.148) | 85 |
| Example 14 | Compound A-3 | 6.4 | (0.132, 0.150) | 110 |
| Comparative Example 7 | Comparative Compound 1 | 5.9 | (0.133, 0.149) | 48 |

Referring to Table 4, the organic light emitting diodes according to Examples 12 to 14 showed simultaneously improved luminous efficiency and life-span characteristics compared with the organic light emitting diode according to Comparative Example 7.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A composition for an organic optoelectronic device, comprising:
   a first compound represented by Chemical Formula 1; and
   a second compound represented by Chemical Formula 2:

[Chemical Formula 1]

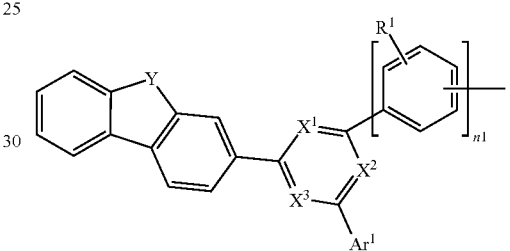

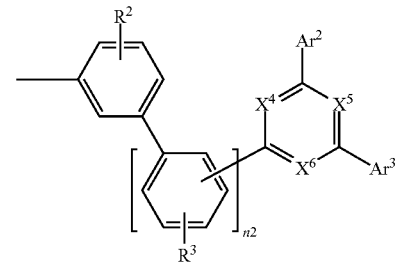

wherein, in Chemical Formula 1, $X^1$ to $X^6$ are independently N or $CR^a$, at least two of $X^1$ to $X^3$ are N, at least two of $X^4$ to $X^6$ are N, Y is O or S, $Ar^1$ to $Ar^3$ are independently a substituted or unsubstituted C6 to C30 aryl group, $R^a$ and $R^1$ to $R^3$ are independently hydrogen, deuterium, a substituted or unsubstituted C1 to C10 alkyl group, a substituted or unsubstituted C6 to C30 aryl group, or a combination thereof, and n1 and n2 are independently one of integers of 0 to 2,

[Chemical Formula 2]

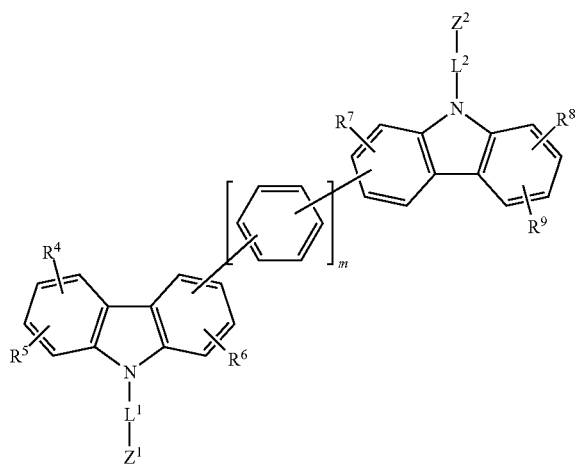

wherein, in Chemical Formula 2, $L^1$ and $L^2$ are independently a single bond, a substituted or unsubstituted C6 to C30 arylene group, a substituted or unsubstituted C2 to C30 heteroarylene group, or a combination thereof, $Z^1$ and $Z^2$ are independently a substituted or unsubstituted C6 to C30 aryl group, a substituted or unsubstituted C2 to C30 heterocyclic group, or a combination thereof, $R^4$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is one of integers of 0 to 2, wherein the "substituted" in Chemical Formulae 1 and 2 refers to replacement of at least one hydrogen by deuterium, a C1 to C4 alkyl group, a C6 to C18 aryl group, or a C2 to C30 heteroaryl group.

2. The composition for an organic optoelectronic device of claim 1, wherein the first compound represented by Chemical Formula 1 is represented by one of Chemical Formula 1-I, Chemical Formula 1-II, Chemical Formula 1-III, Chemical Formula 1-IV, Chemical Formula 1-V, and Chemical Formula 1-VI:

[Chemical Formula 1-I]

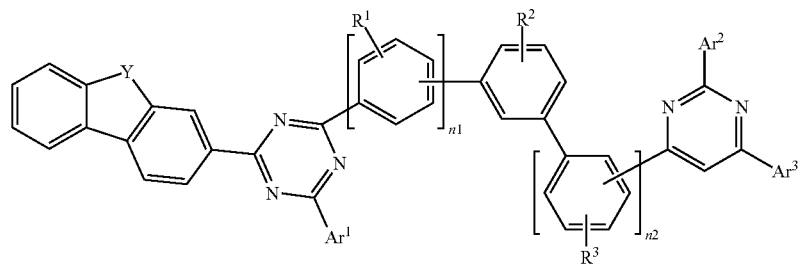

[Chemical Formula 1-II]

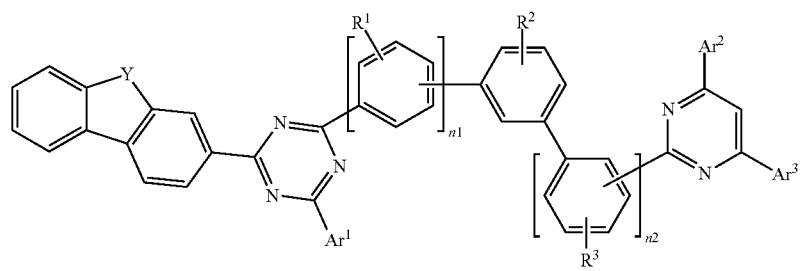

[Chemical Formula 1-III]

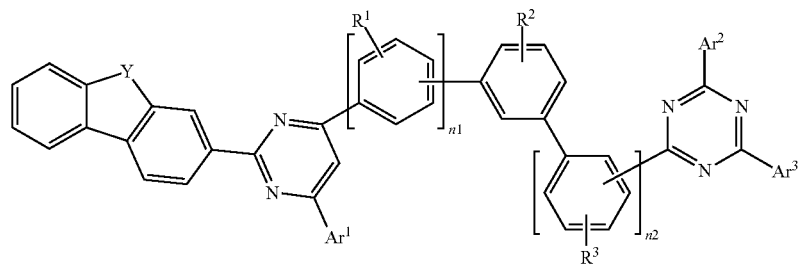

-continued

[Chemical Formula 1-IV]

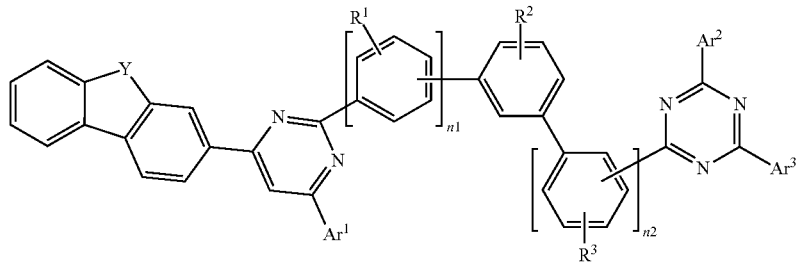

[Chemical Formula 1-V]

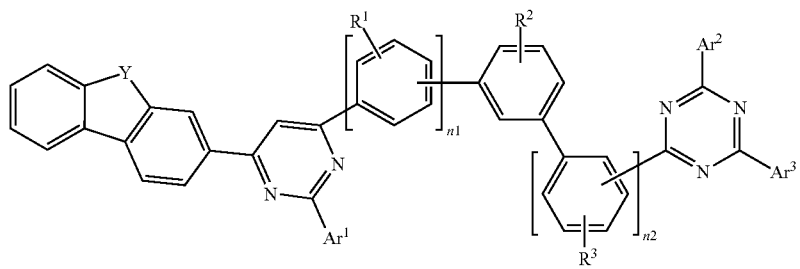

[Chemical Formula 1-VI]

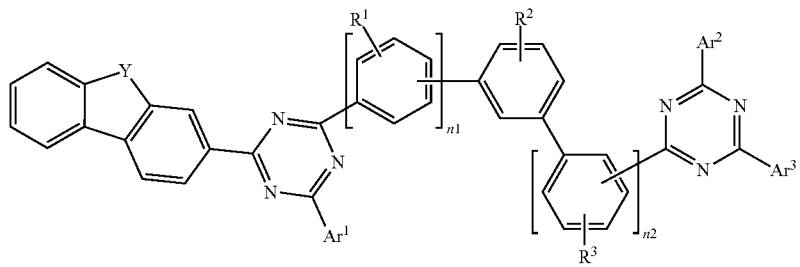

wherein, in Chemical Formula 1-I, Chemical Formula 1-II, Chemical Formula 1-III, Chemical Formula 1-IV, Chemical Formula 1-V, and Chemical Formula 1-VI, Y is O or S, $Ar^1$ to $Ar^3$ are independently a substituted or unsubstituted C6 to C30 aryl group, $R^1$ to $R^3$ are independently hydrogen, deuterium, a substituted or unsubstituted C1 to C10 alkyl group, a substituted or unsubstituted C6 to C30 aryl group, or a combination thereof, and n1 and n2 are independently one of integers of 0 to 2.

3. The composition for an organic optoelectronic device of claim 1, wherein the first compound represented by Chemical Formula 1 is represented by one of Chemical Formulae 1-1 to 1-3:

[Chemical Formula 1-1]

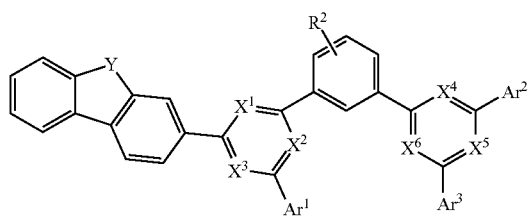

[Chemical Formula 1-2]

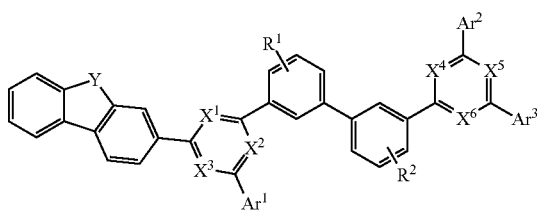

-continued

[Chemical Formula 1-3]

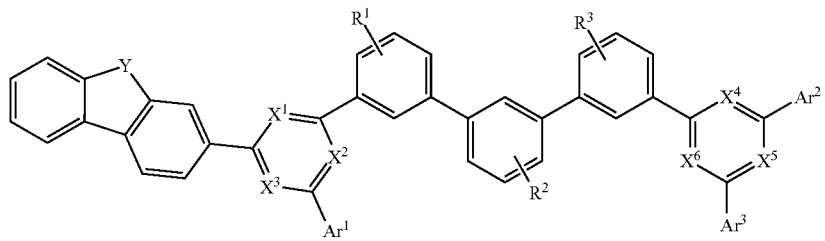

wherein, in Chemical Formulae 1-1 to 1-3,
$X^1$ to $X^6$ are independently N or CH,
at least two of $X^1$ to $X^3$ are N,
at least two of $X^4$ to $X^6$ are N,
Y is O or S,
$Ar^1$ to $Ar^3$ are independently a substituted or unsubstituted C6 to C30 aryl group,
$R^1$ to $R^3$ are independently hydrogen, deuterium, a substituted or unsubstituted C1 to C10 alkyl group, a substituted or unsubstituted C6 to C30 aryl group, or a combination thereof, and
n1 and n2 are independently one of integers of 0 to 2.

4. The composition for an organic optoelectronic device of claim 1, wherein the $Ar^1$ to $Ar^3$ of Chemical Formula 1 are independently a substituted or unsubstituted phenyl group, a substituted or unsubstituted biphenyl group, a substituted or unsubstituted terphenyl group, a substituted or unsubstituted naphthyl group, or a substituted or unsubstituted fluorenyl group.

5. The composition for an organic optoelectronic device of claim 1, wherein the $R^1$ to $R^3$ of Chemical Formula 1 are independently hydrogen, deuterium, a methyl group, an ethyl group, a n-propyl group, an iso-propyl group, a substituted or unsubstituted phenyl group, or a substituted or unsubstituted naphthyl group.

6. The composition for an organic optoelectronic device of claim 1, wherein the first compound represented by Chemical Formula 1 is selected from compounds of Group 1:

[Group 1]

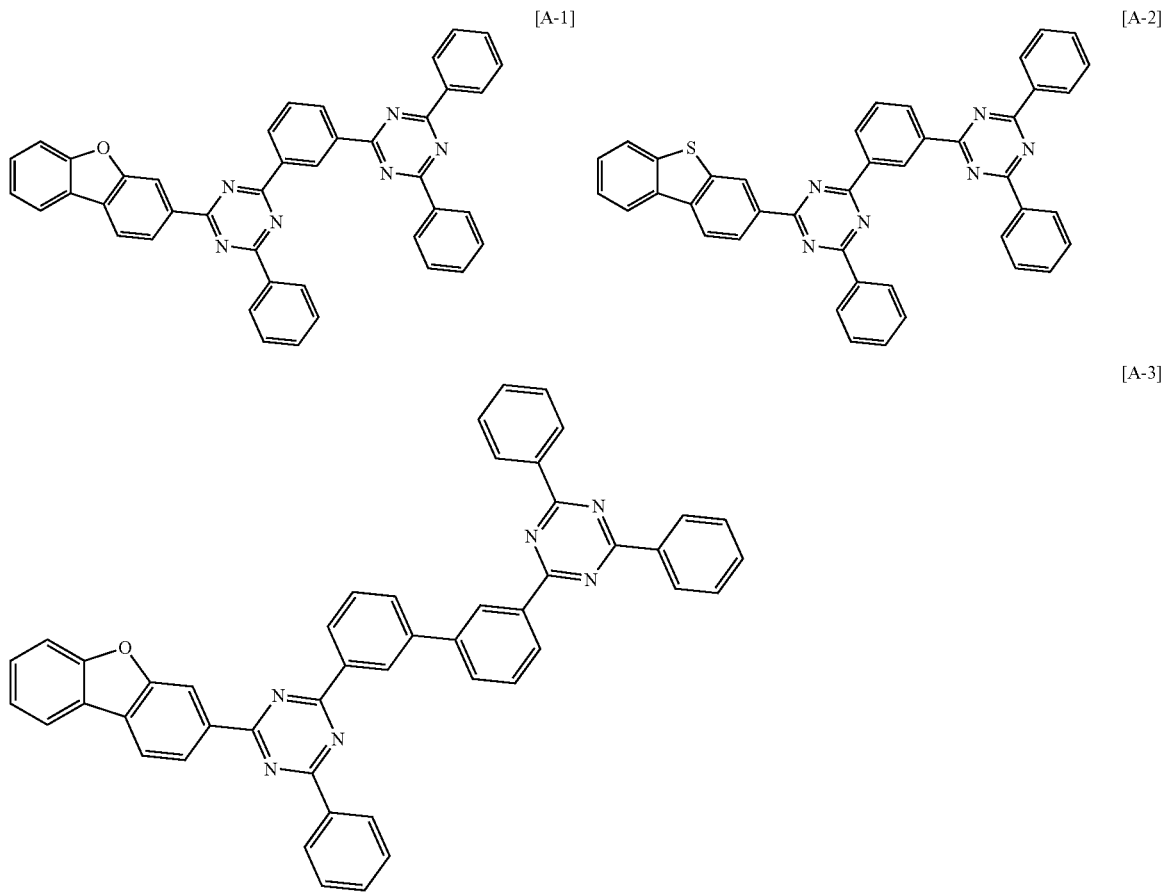

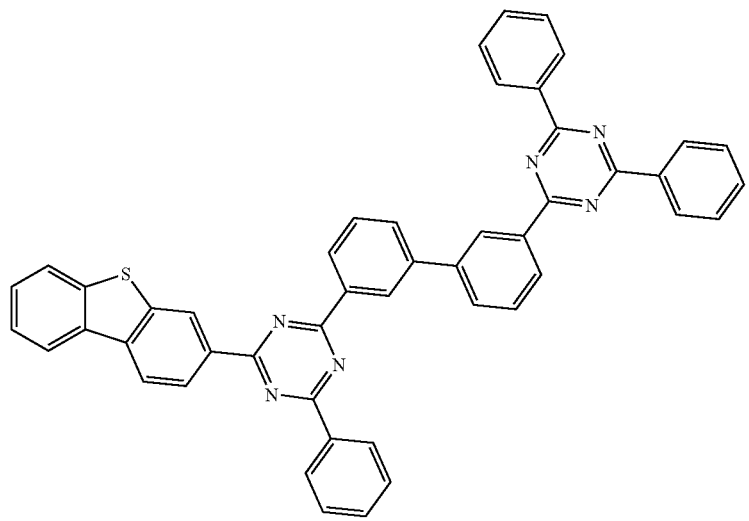
[A-4]
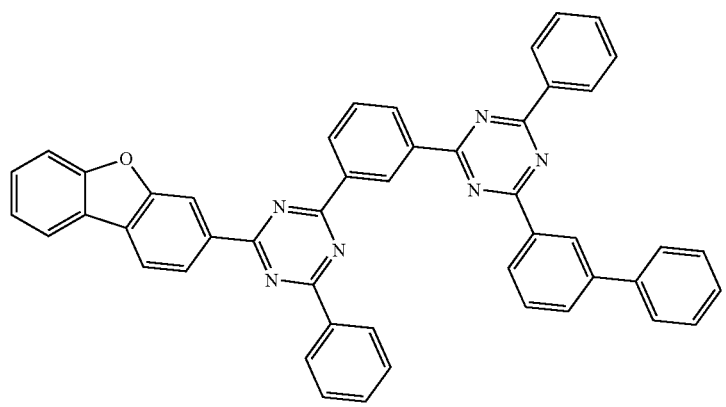
[A-5]
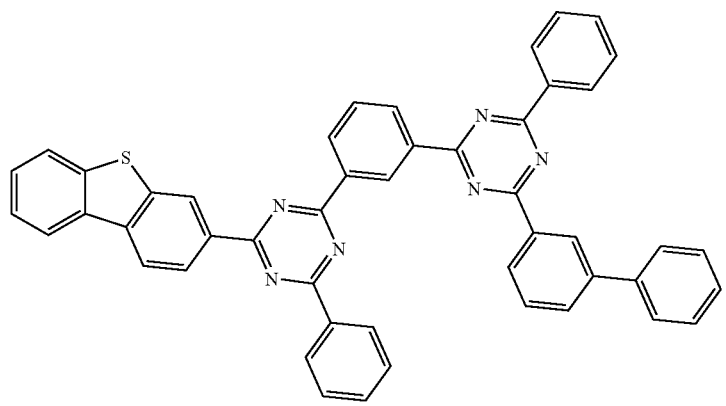
[A-6]

-continued
[A-7]
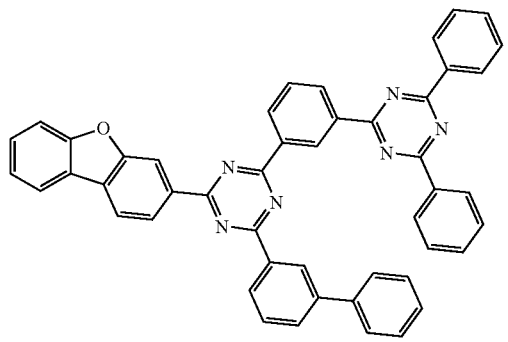
[A-8]
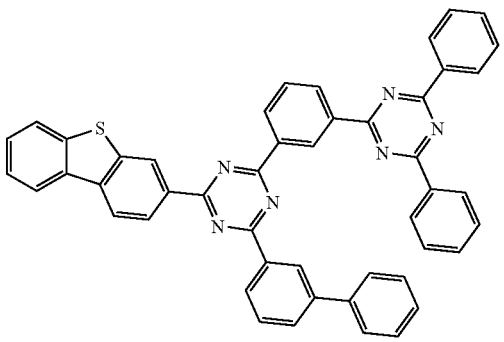
[A-9]
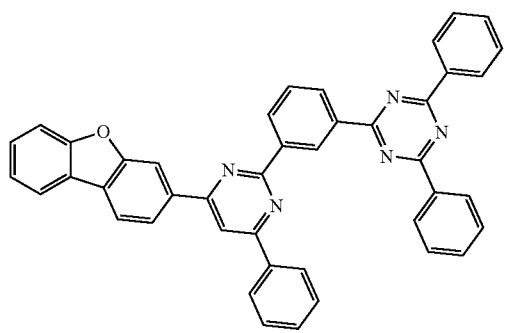
[A-10]
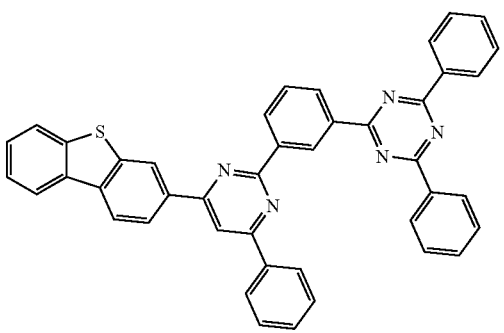
[A-11]
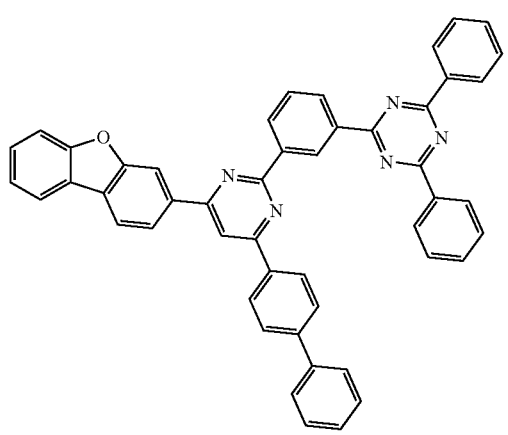
[A-12]
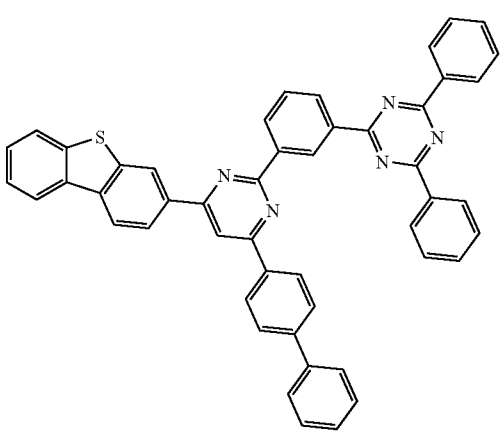
[A-13]
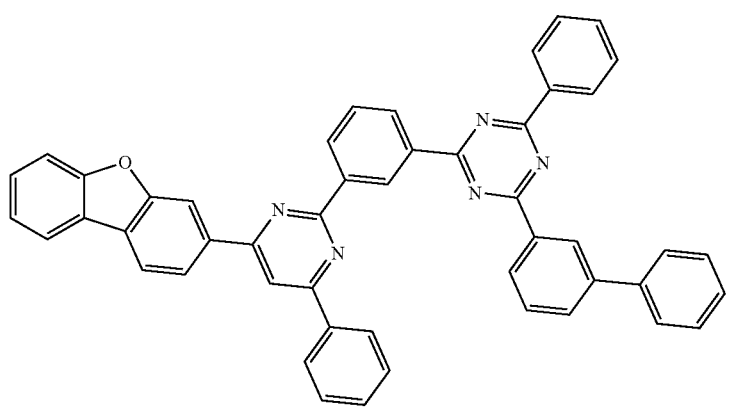

[A-14]
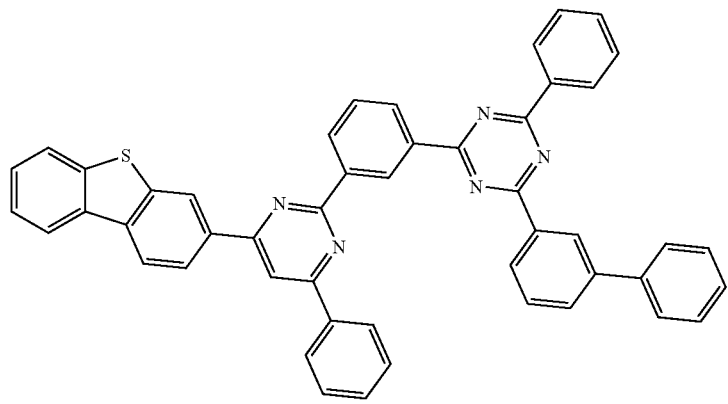
[A-15]
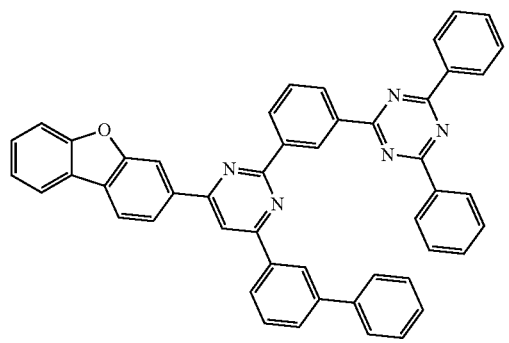
[A-16]
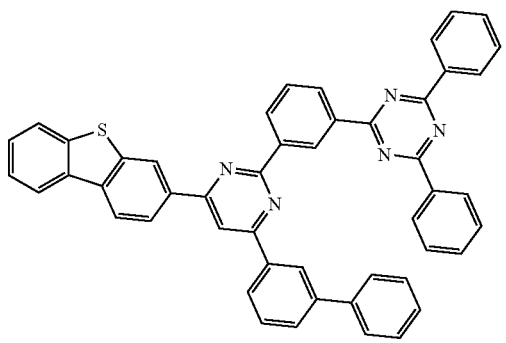
[A-17]
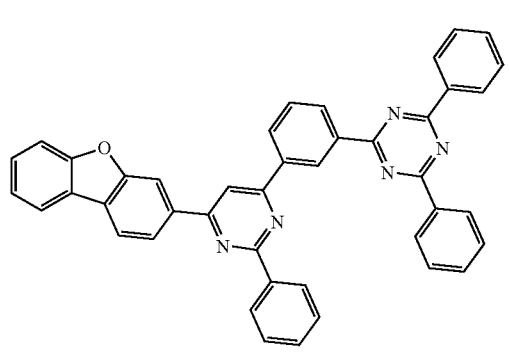
[A-18]
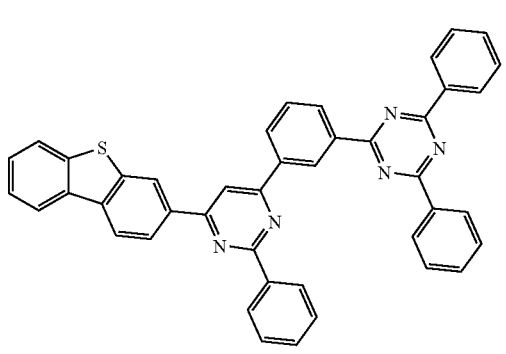
[A-19]
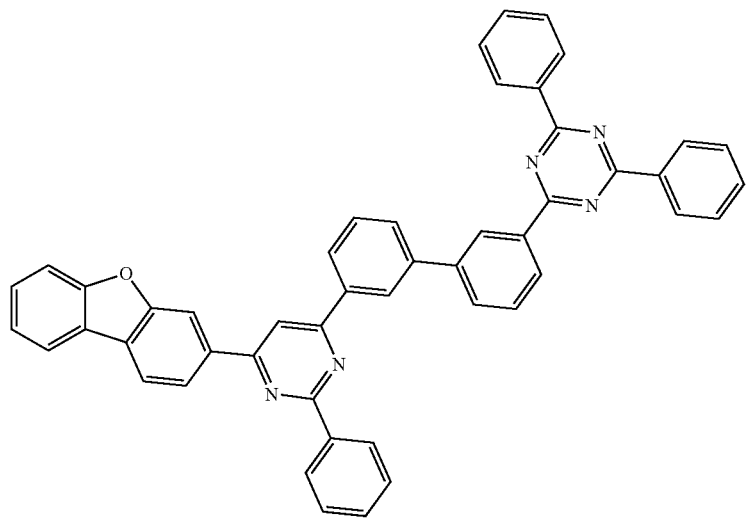

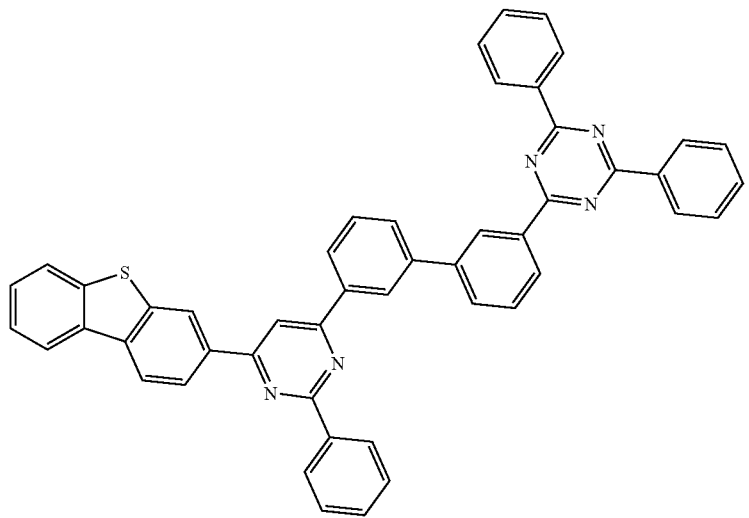
[A-20]
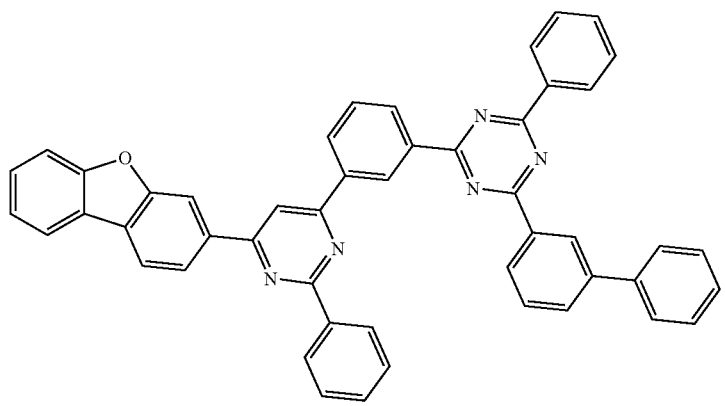
[A-21]
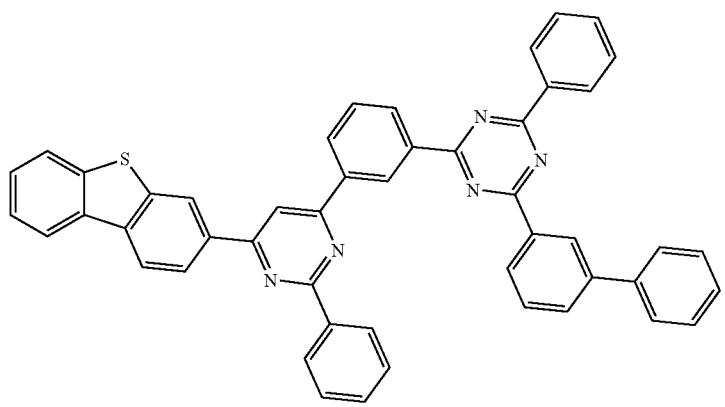
[A-22]

-continued
[A-23]
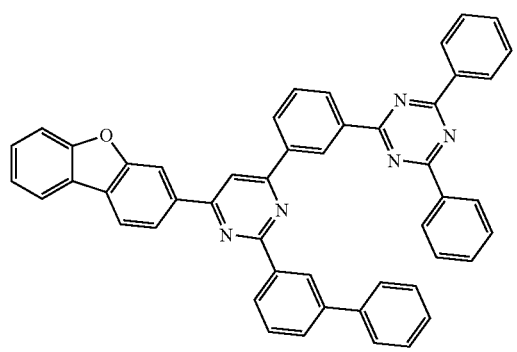
[A-24]
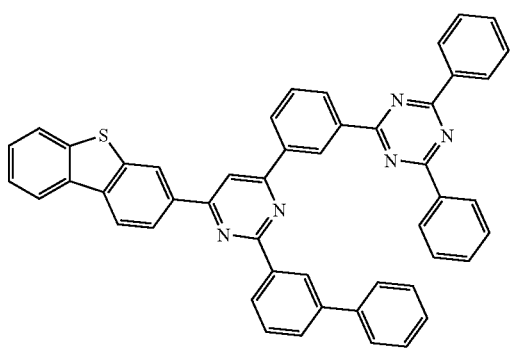
[A-25]
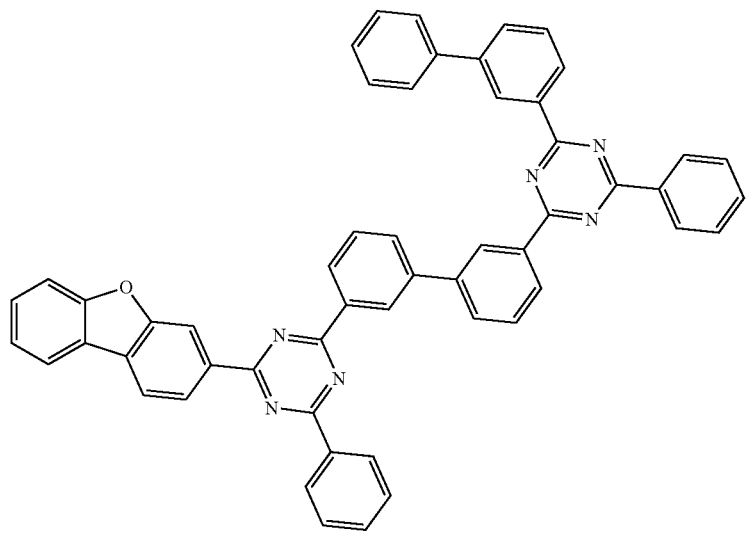
[A-26]
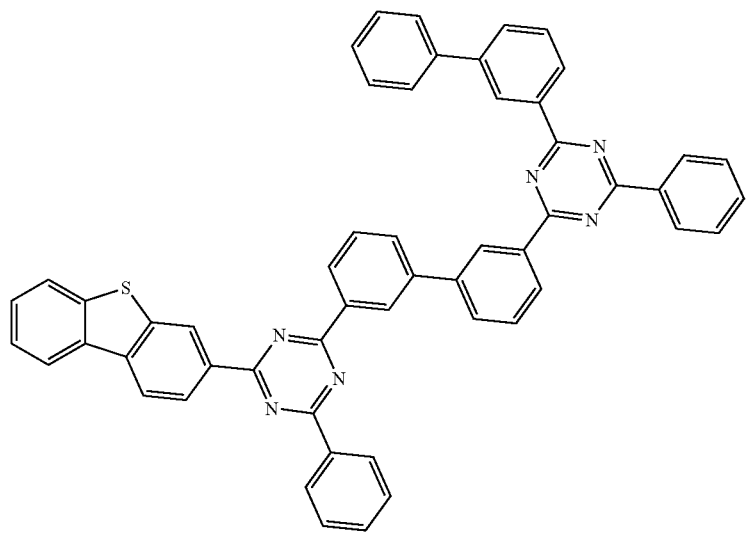

-continued
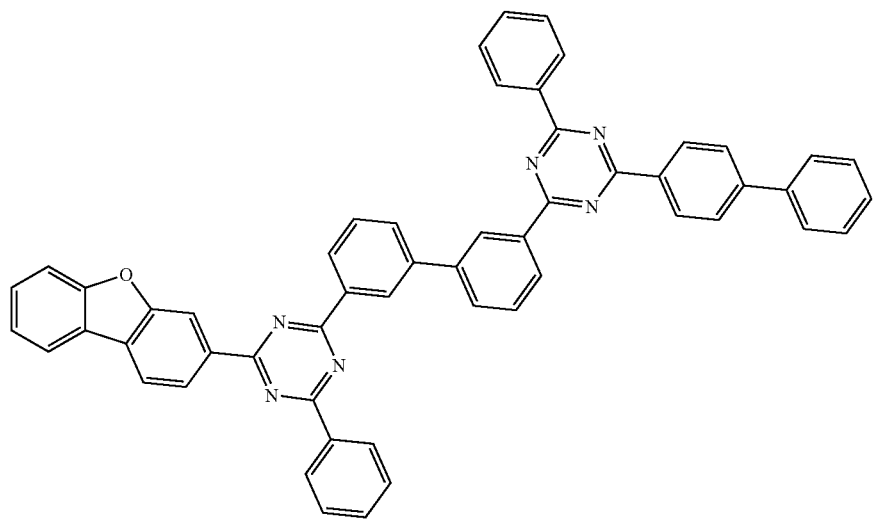
[A-27]
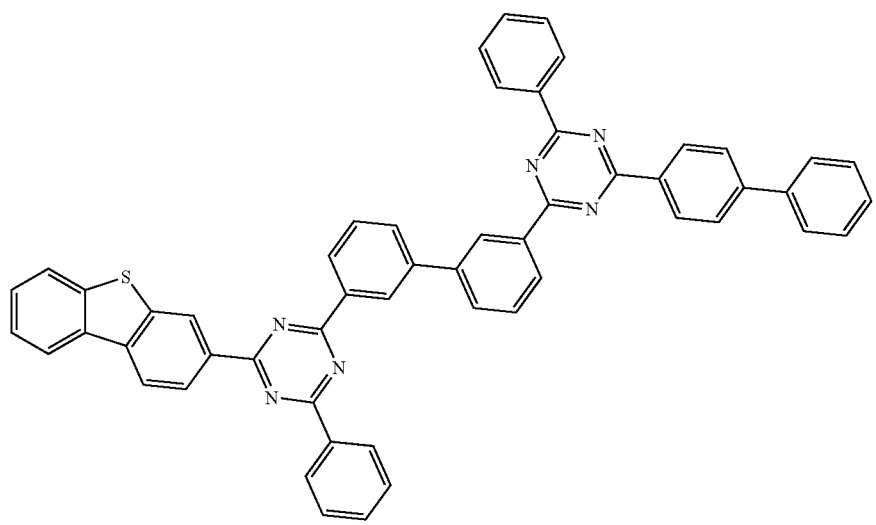
[A-28]
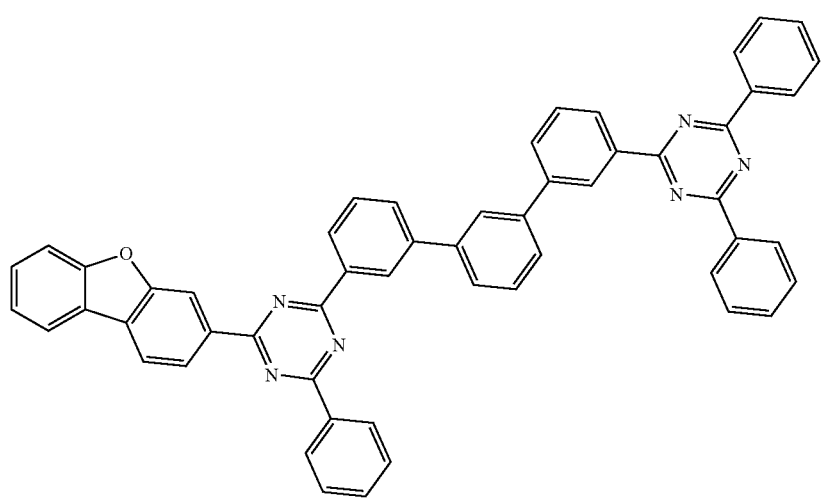
[A-29]

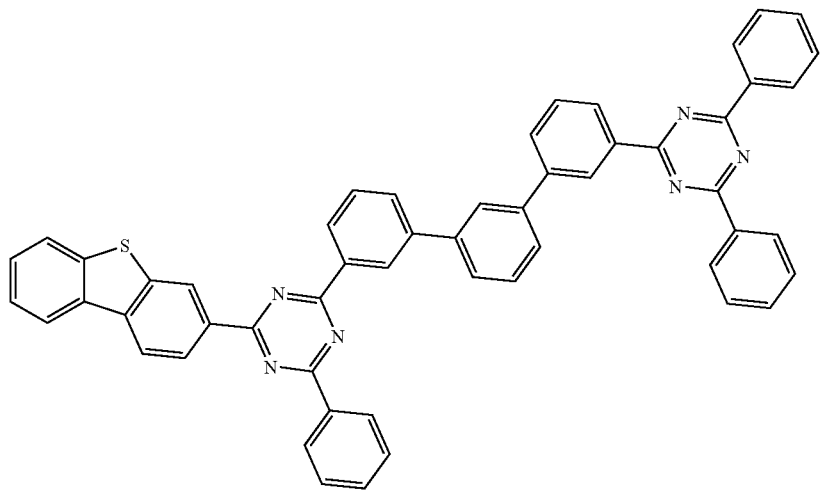
[A-30]
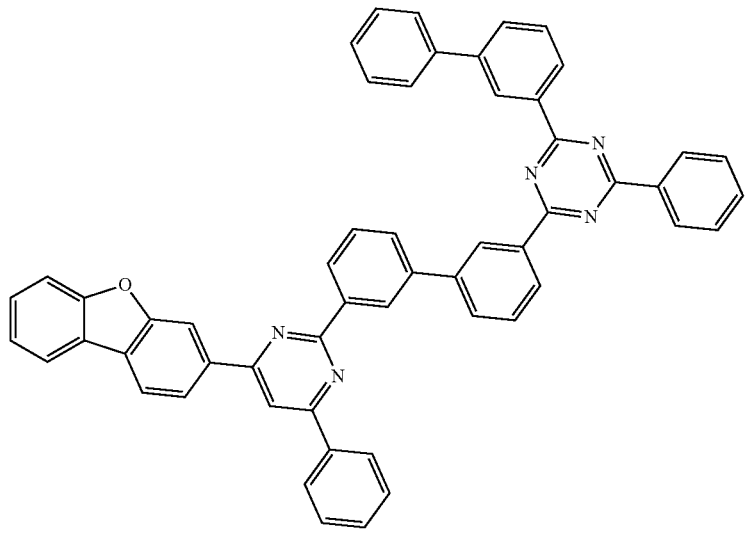
[A-31]
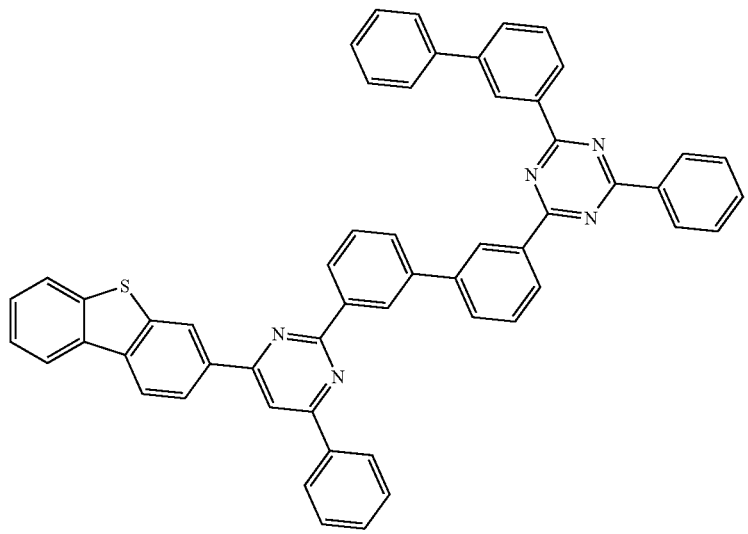
[A-32]

-continued
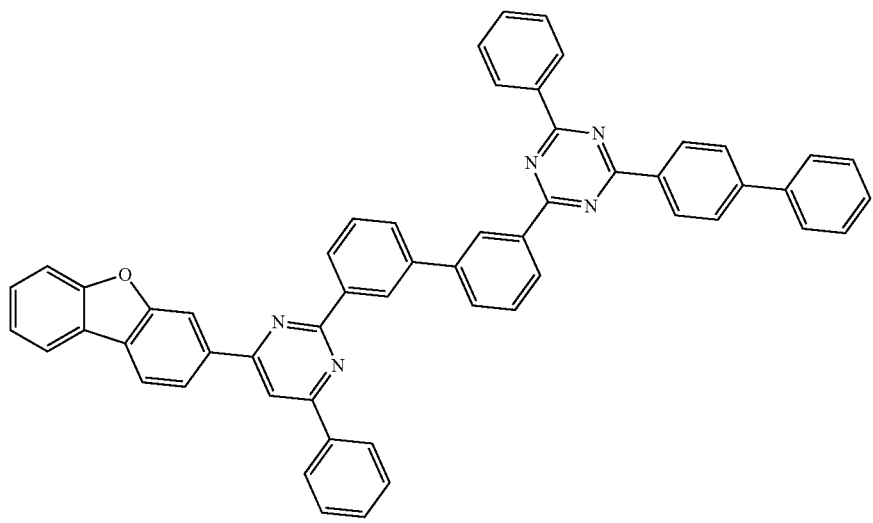
[A-33]
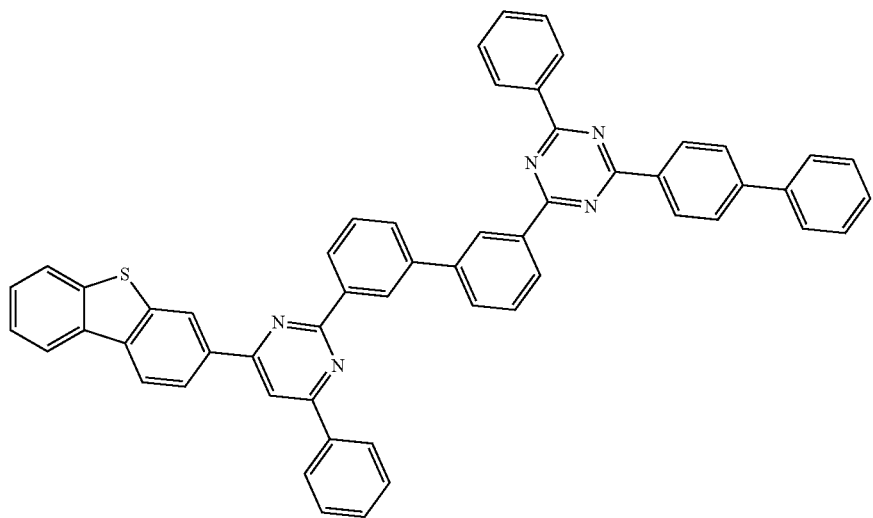
[A-34]
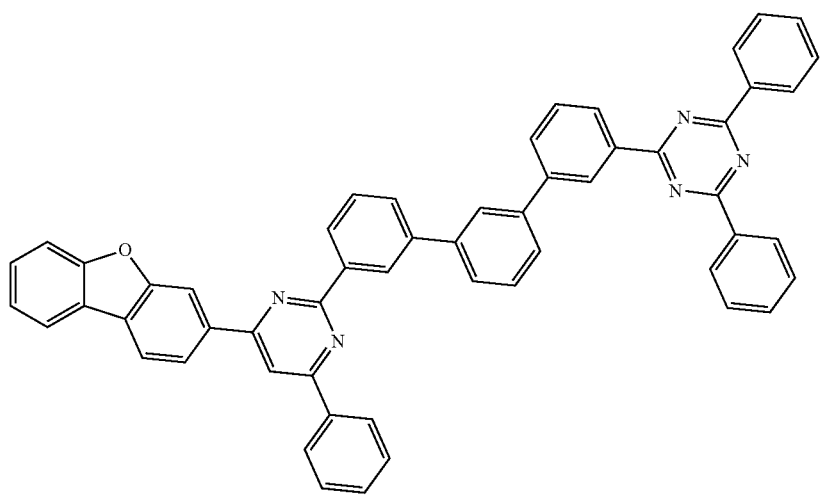
[A-35]

-continued
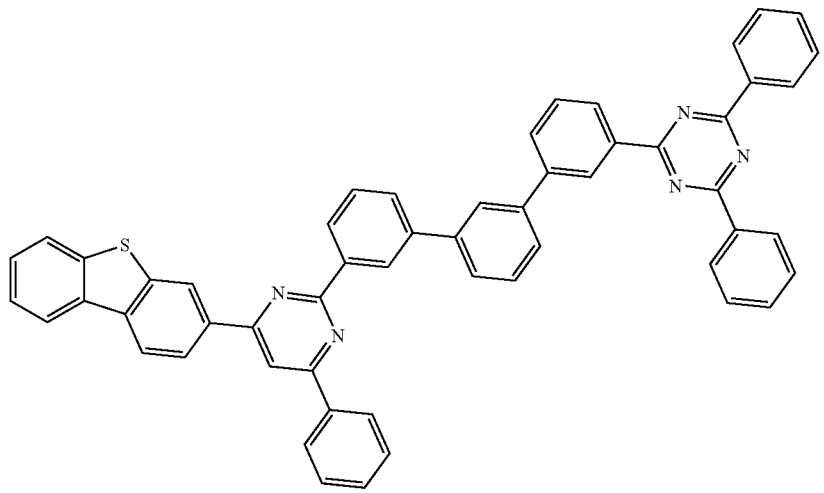
[A-36]
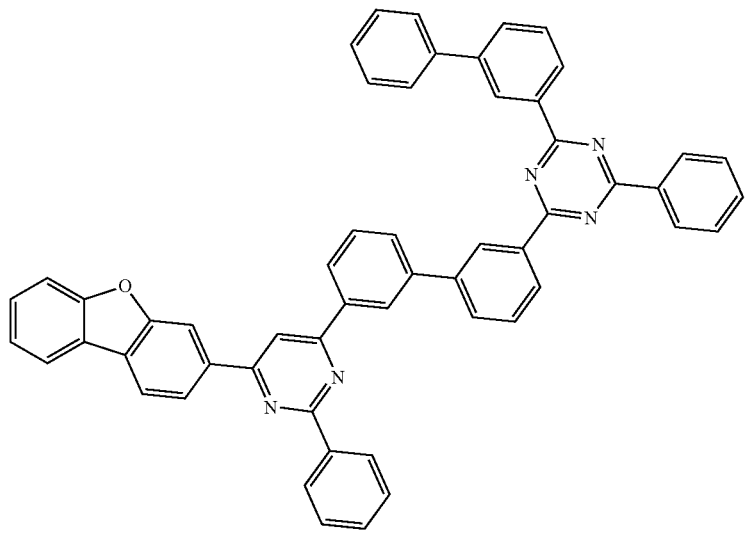
[A-37]
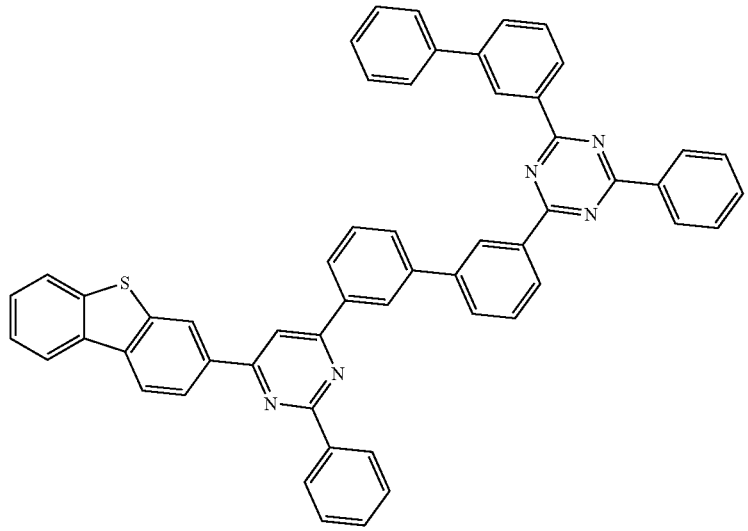
[A-38]

-continued
[A-39]
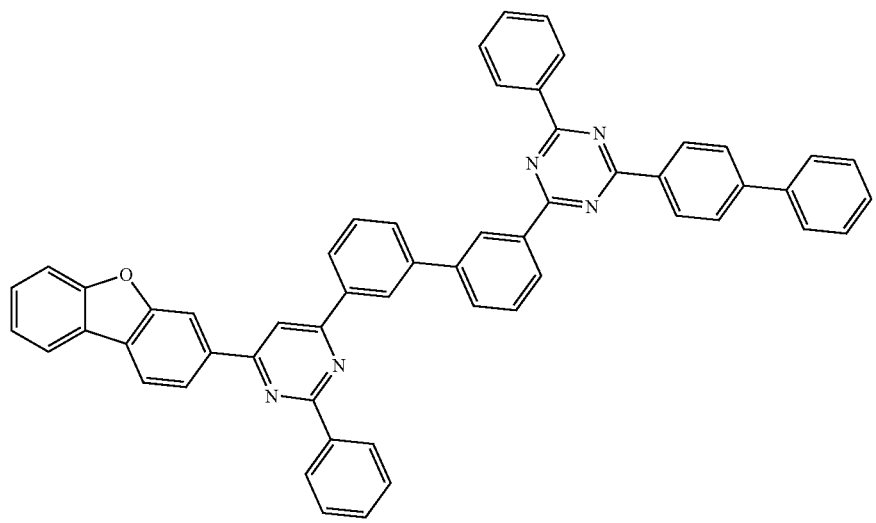
[A-40]
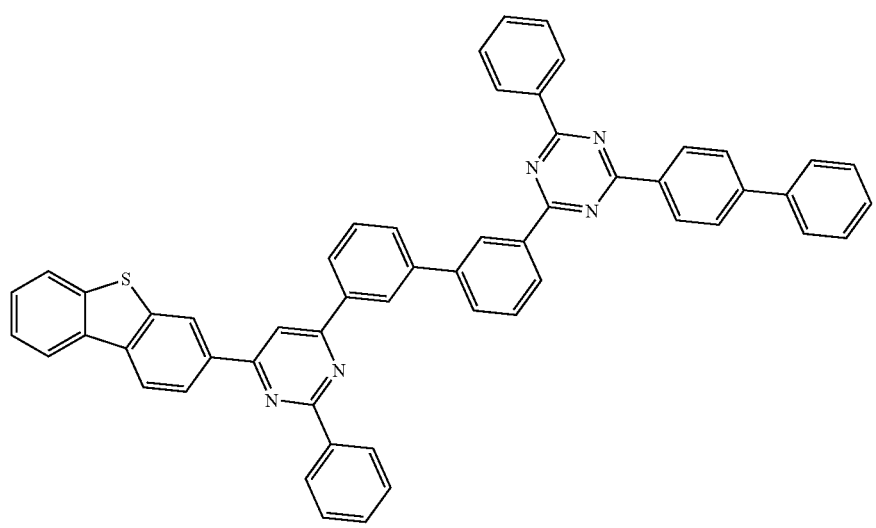
[A-41]
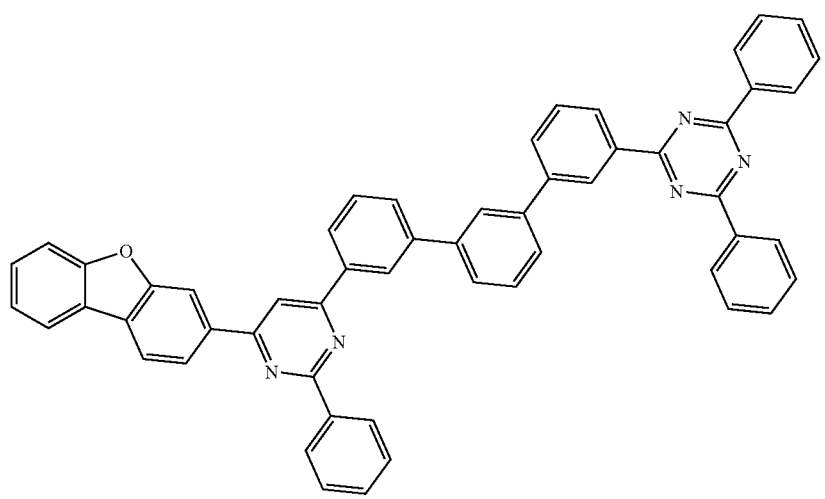

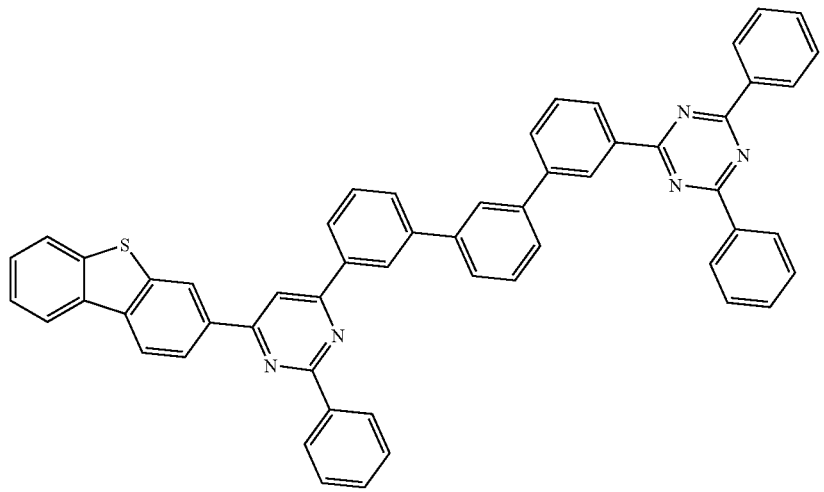
[A-42]
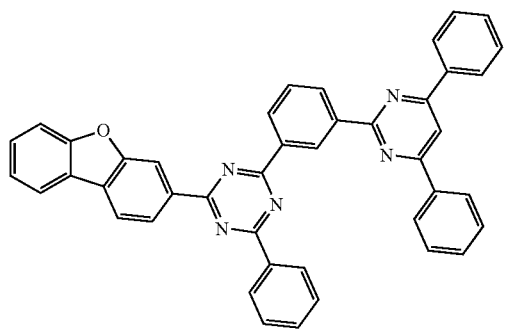
[A-43]
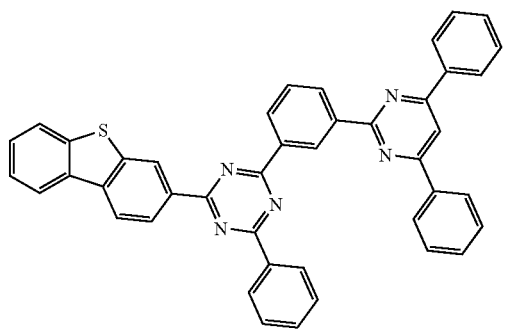
[A-44]
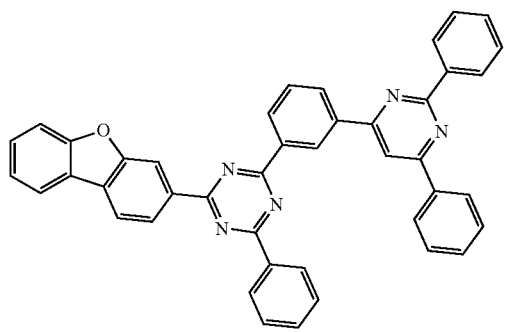
[A-45]
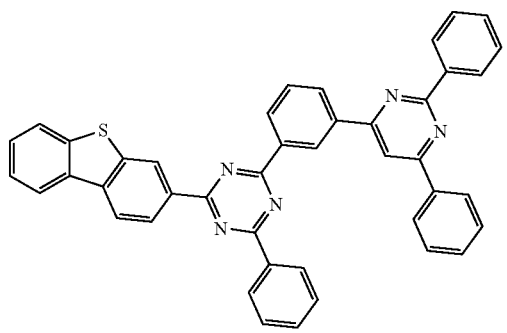
[A-46]
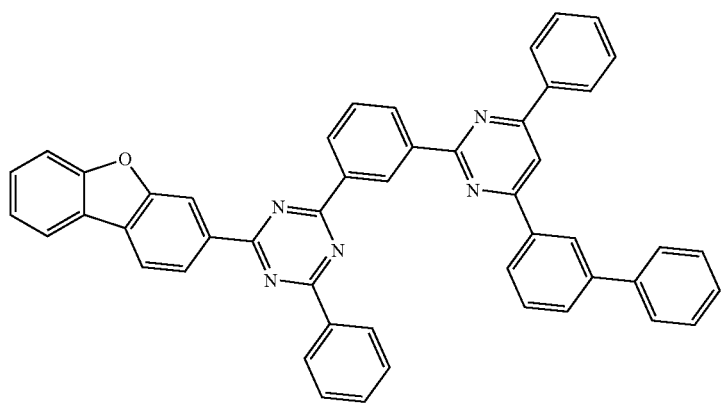
[A-47]

[A-48]
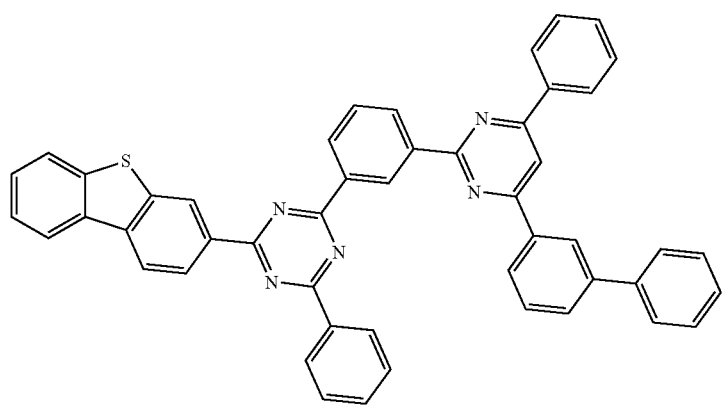
[A-49]
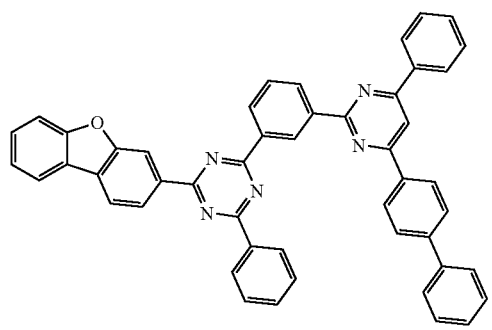
[A-50]
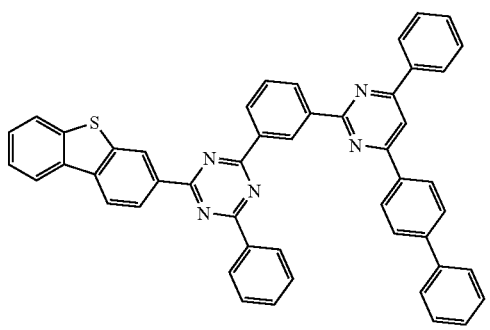
[A-51]
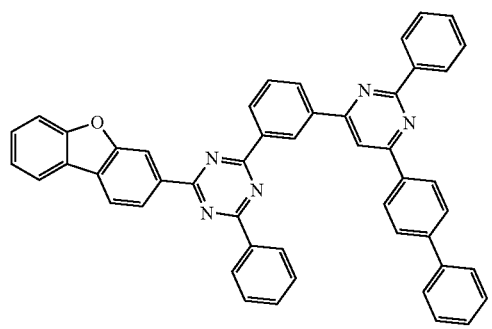
[A-52]
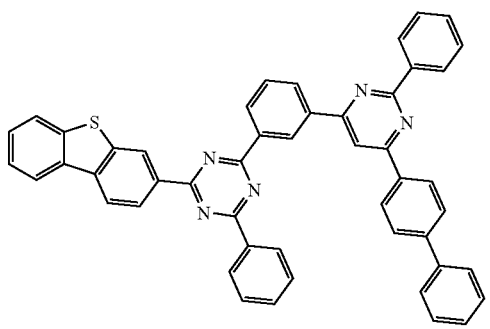
[A-53]
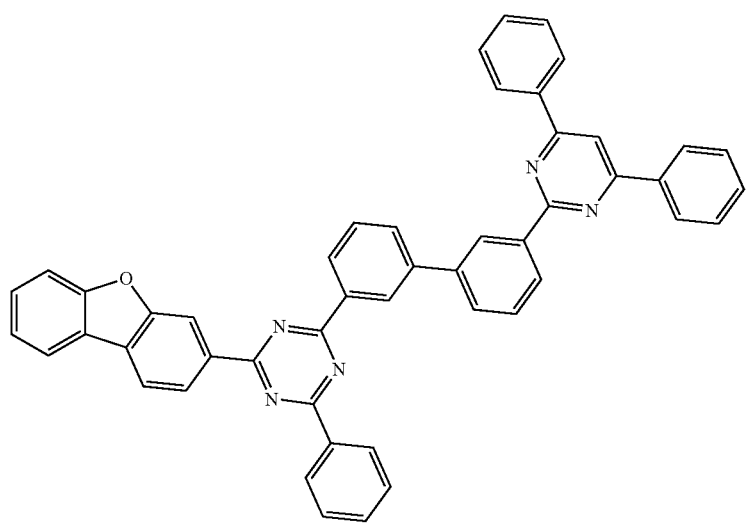

-continued
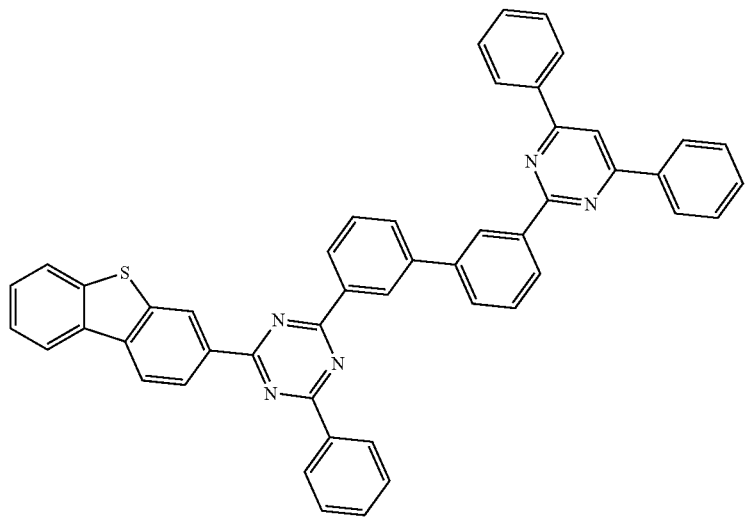
[A-54]
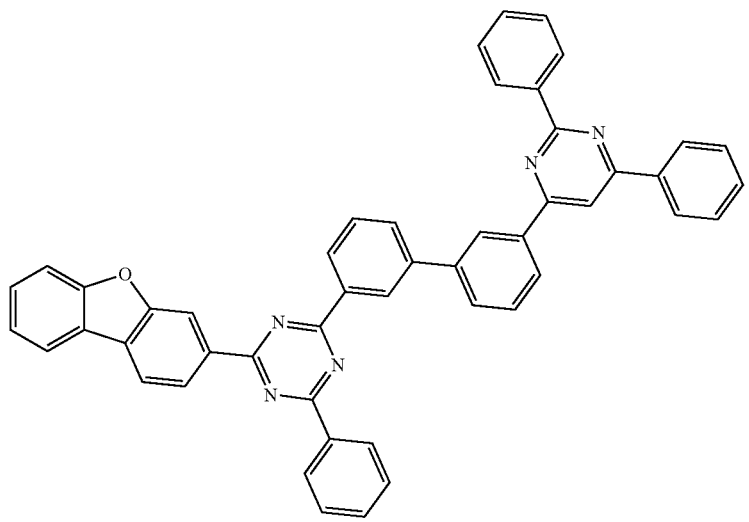
[A-55]
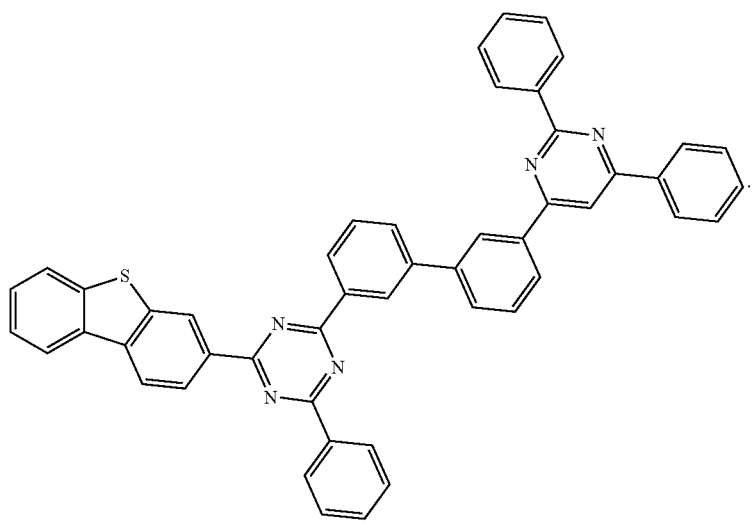
[A-56]

7. The composition for an organic optoelectronic device of claim 1, wherein the $Z^1$ and $Z^2$ of Chemical Formula 2 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylene group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

8. The composition for an organic optoelectronic device of claim 1, wherein Chemical Formula 2 has one of structures of Group I and the *-$L^1$-$Z^1$ and *-$L^2$-$Z^2$ of Chemical Formula 2 are independently one of substituents of Group II:

[Group I]

C-1
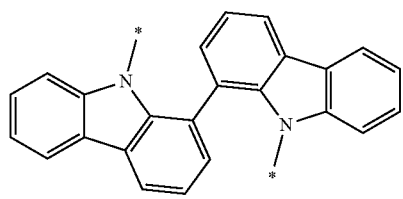

C-2
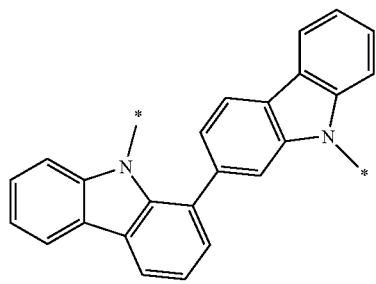

C-3
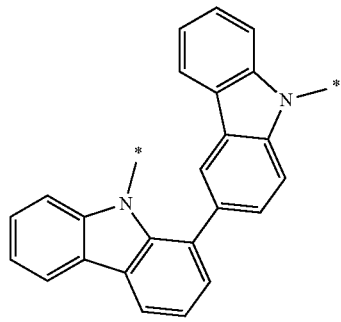

C-4
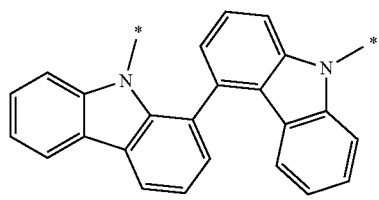

-continued

C-5
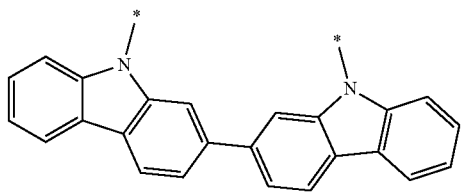

C-6
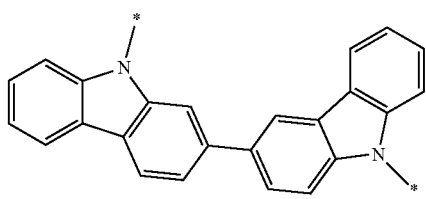

C-7
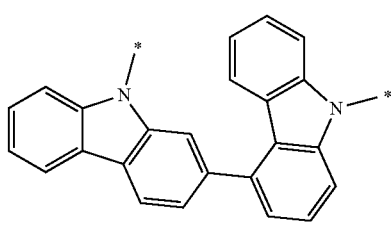

C-8
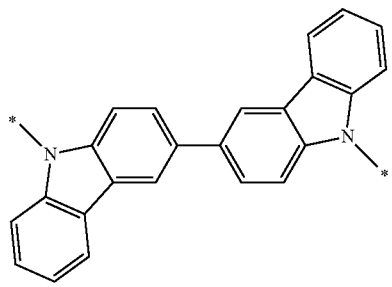

C-9
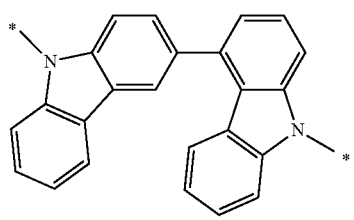

C-10
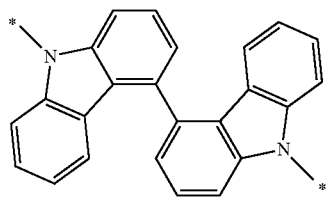

-continued
C-11
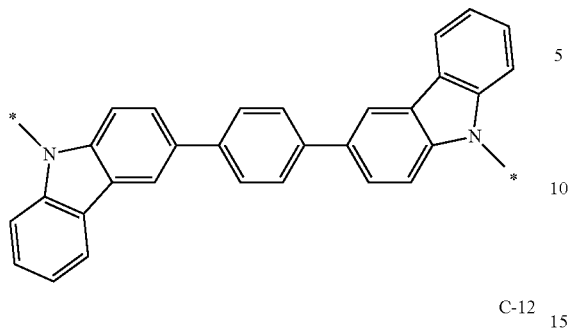
C-12
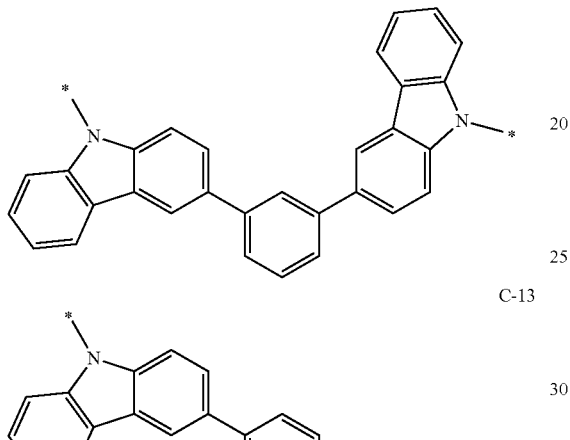
C-13
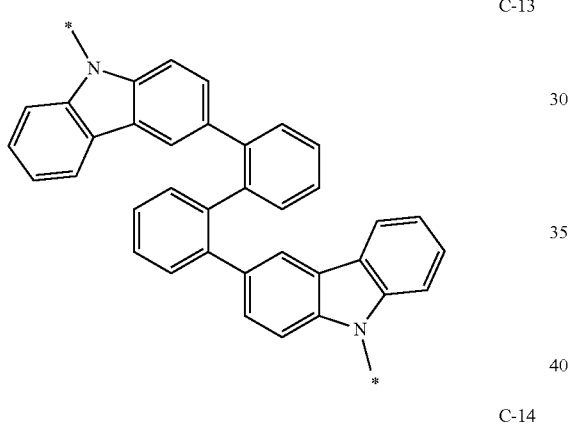
C-14
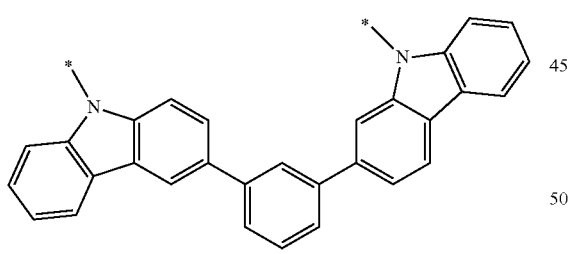
C-15
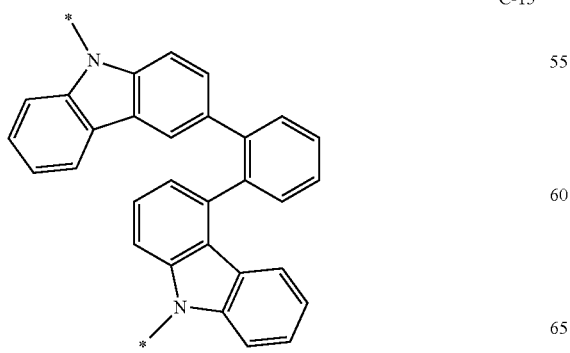
-continued
C-16
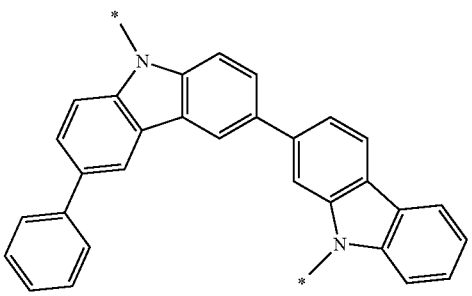
C-17
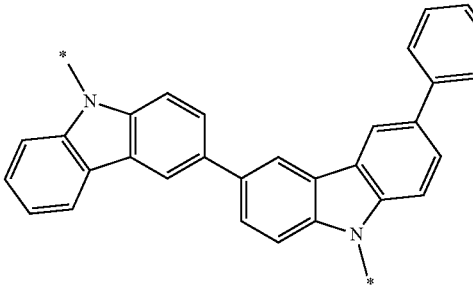
C-18
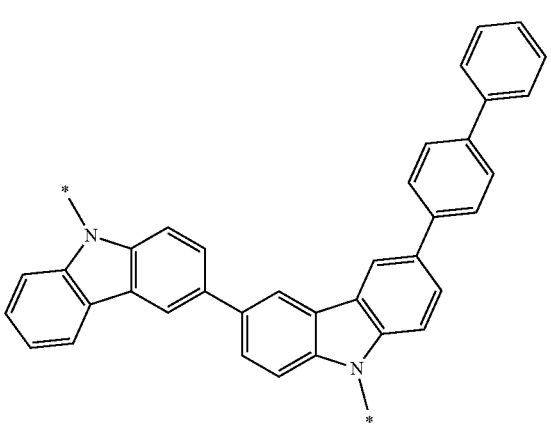
[Group II]
B-1
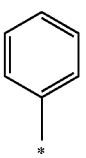

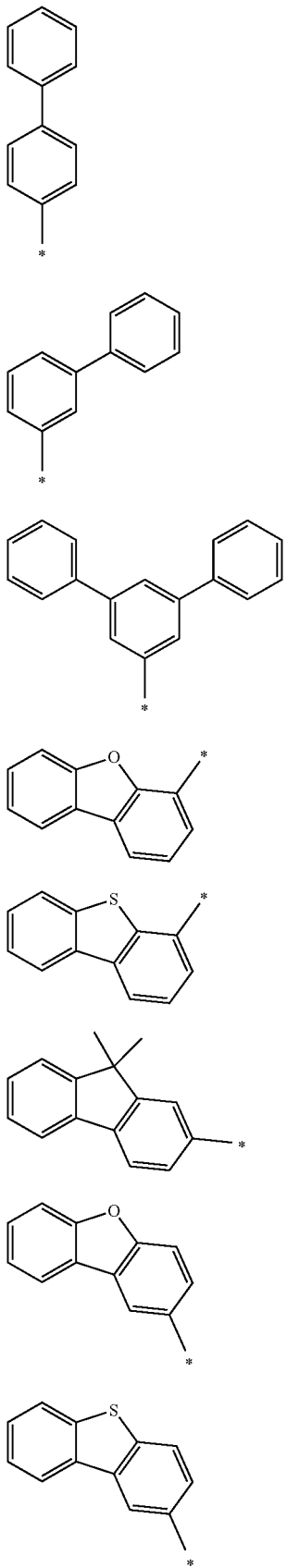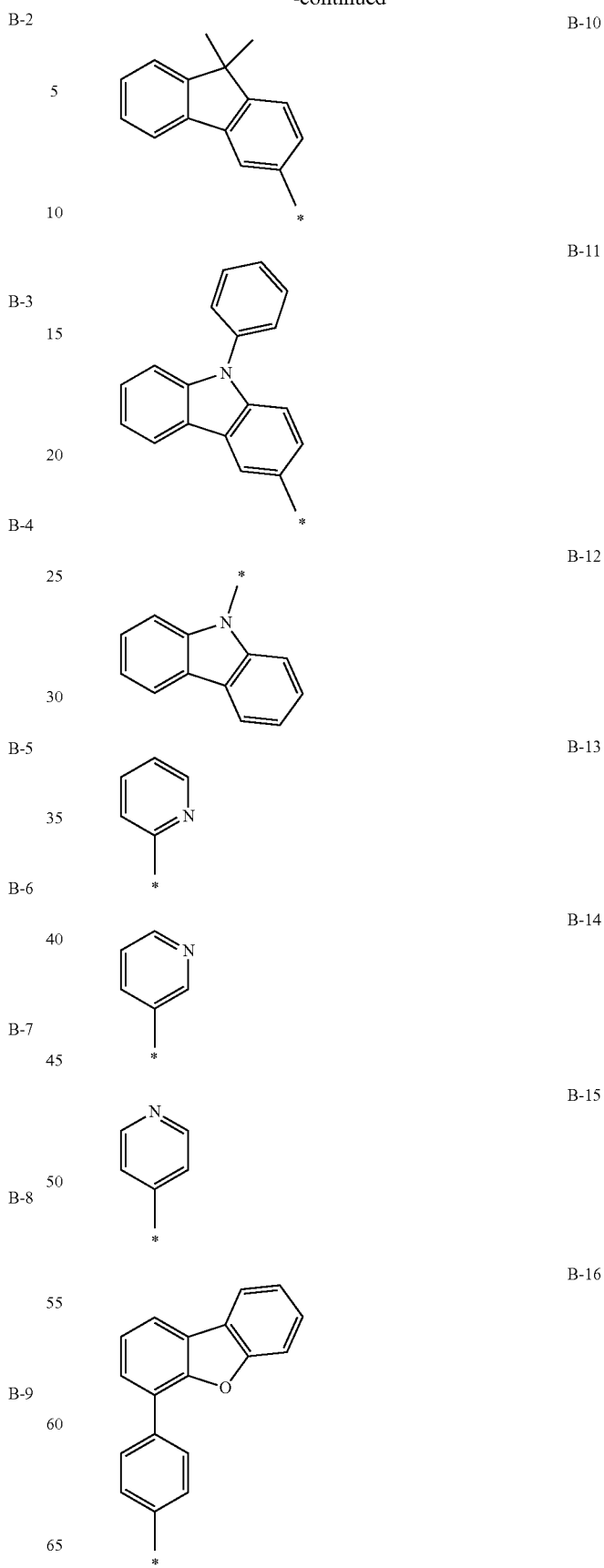

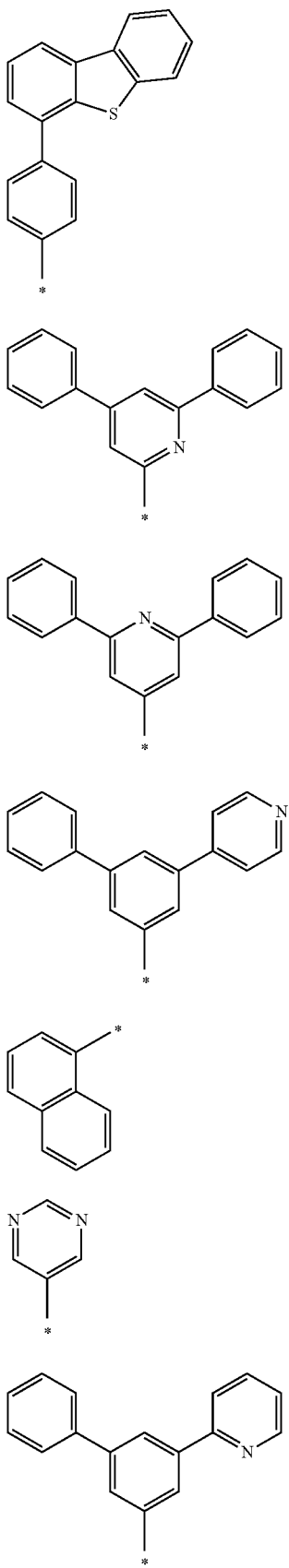
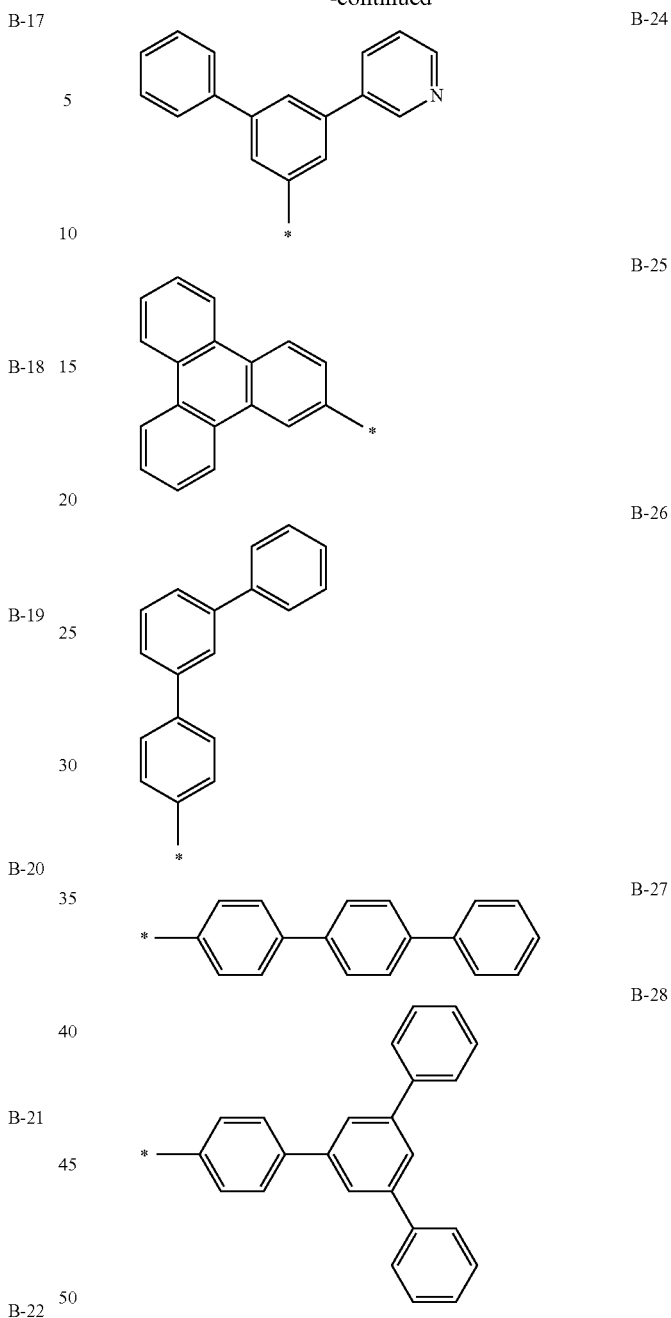

wherein, in Groups I and II, * is a linking point.

9. The composition for an organic optoelectronic device of claim 8, wherein Chemical Formula 2 has one of structures C-8 or C 17 of Group I, and
the *-$L^1$-$Z^1$ and *-$L^2$-$Z^2$ of Chemical Formula 2 are independently one of substituents B-1, B-2, B-3, B-16, and B-17 of Group II.

10. An organic optoelectronic device, comprising
an anode and a cathode facing each other, and
at least one organic layer disposed between the anode and the cathode,
wherein the organic layer includes the composition for an organic optoelectronic device of claim 1.

11. The organic optoelectronic device of claim 10, wherein the organic layer includes a light emitting layer, and the light emitting layer includes the composition for an organic optoelectronic device.

12. The organic optoelectronic device of claim 11, wherein the composition for an organic optoelectronic device is included as a host of the light emitting layer.

13. The organic optoelectronic device of claim 12, wherein
- the organic layer includes at least one auxiliary layer selected from a hole injection layer, a hole transport layer, an electron blocking layer, an electron transport layer, an electron injection layer, and a hole blocking layer,
- the auxiliary layer further includes an electron transport auxiliary layer that is adjacent to the light emitting layer, and
- the electron transport auxiliary layer includes the composition for an organic optoelectronic device.

14. A display device comprising the organic optoelectronic device of claim 10.

* * * * *